(12) United States Patent
Gu et al.

(10) Patent No.: US 9,567,300 B2
(45) Date of Patent: Feb. 14, 2017

(54) HEXAHYDROPENTALENO DERIVATIVES, PREPARATION METHOD AND USE IN MEDICINE THEREOF

(71) Applicant: SUNSHINE LAKE PHARMA CO., LTD., Dongguan, Guangdong (CN)

(72) Inventors: Zheng Gu, Dongguan (CN); Guanpeng Qiu, Dongguan (CN); Wuyong Wu, Dongguan (CN); Panpan Kang, Dongguan (CN); Zongyuan Zhang, Dongguan (CN); Gang Chen, Dongguan (CN); Chengsheng Lan, Dongguan (CN); Yonggang Wei, Dongguan (CN); Jiaping Wen, Dongguan (CN); Guozhi Zhu, Dongguan (CN); Yonghua Lu, Dongguan (CN); Heran Wang, Dongguan (CN); Yincai Wang, Dongguan (CN); Mingyun Yuan, Dongguan (CN); Kangzhi Ye, Dongguan (CN); Guizhuan Su, Dongguan (CN); PengCho Tang, Dongguan (CN)

(73) Assignee: SUNSHINE LAKE PHARMA CO., LTD., Dongguan, Guangdong (CN)

( * ) Notice: Subject to any disclaimer, the term of this patent is extended or adjusted under 35 U.S.C. 154(b) by 69 days.

(21) Appl. No.: 14/378,975

(22) PCT Filed: Jun. 25, 2013

(86) PCT No.: PCT/CN2013/077899
§ 371 (c)(1),
(2) Date: Aug. 15, 2014

(87) PCT Pub. No.: WO2014/000629
PCT Pub. Date: Jan. 3, 2014

(65) Prior Publication Data
US 2015/0299118 A1     Oct. 22, 2015

(30) Foreign Application Priority Data

Jun. 25, 2012  (CN) .......................... 2012 1 0207680
Apr. 3, 2013   (CN) .......................... 2013 1 0116954

(51) Int. Cl.
| C07D 207/16 | (2006.01) |
| A61K 31/40 | (2006.01) |
| C07D 405/12 | (2006.01) |
| C07D 209/52 | (2006.01) |
| A61K 31/403 | (2006.01) |
| C07C 217/52 | (2006.01) |
| A61K 45/06 | (2006.01) |
| C07C 255/47 | (2006.01) |
| C07C 213/02 | (2006.01) |
| C07C 253/30 | (2006.01) |

(Continued)

(52) U.S. Cl.
CPC ............. C07D 207/16 (2013.01); A61K 31/40 (2013.01); A61K 31/403 (2013.01); A61K 31/4025 (2013.01); A61K 45/06 (2013.01); C07C 213/02 (2013.01); C07C 217/52 (2013.01); C07C 249/08 (2013.01); C07C 253/30 (2013.01); C07C 255/47 (2013.01); C07D 209/52 (2013.01); C07D 405/12 (2013.01); C07C 2101/02 (2013.01); C07C 2102/22 (2013.01); C07C 2103/94 (2013.01)

(58) Field of Classification Search
None
See application file for complete search history.

(56) References Cited

U.S. PATENT DOCUMENTS

| 6,110,949 A | 8/2000 | Villhauer |
| 7,332,520 B2 | 2/2008 | Edmondson et al. |

(Continued)

FOREIGN PATENT DOCUMENTS

| CN | 1040978 A | 4/1990 |
| CN | 1236361 A | 11/1999 |

(Continued)

OTHER PUBLICATIONS

CAPLUS printout of CN102188705, published on Sep. 21, 2011.*

(Continued)

*Primary Examiner* — Matthew Coughlin
*Assistant Examiner* — Po-Chih Chen
(74) *Attorney, Agent, or Firm* — Kam W. Law; Squire Patton Boggs (US) LLP

(57) ABSTRACT

The invention relates to hexahydropentaleno derivatives, the preparation method and use in medicine thereof, and in particular to hexahydropentaleno derivatives or stereo-isomers or pharmaceutically acceptable salts thereof as shown in general formula (I), and to the preparation method therefor and pharmaceutical compositions comprising the derivatives, and to the use thereof as a therapeutical agent, especially as a DPP-IV inhibitor. The definition of each substituent in formula (I) is the same as the definition in the description.

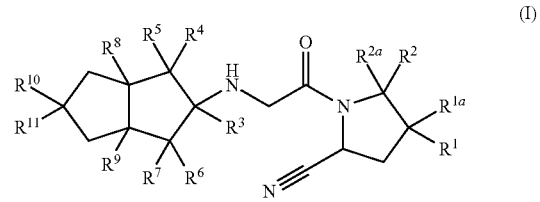

16 Claims, No Drawings

(51) Int. Cl.
*C07C 249/08* (2006.01)
*A61K 31/4025* (2006.01)

(56) References Cited

U.S. PATENT DOCUMENTS

| | | |
|---|---|---|
| 7,345,180 B2 | 3/2008 | Kakigami et al. |
| 7,439,263 B2 | 10/2008 | De Nanteuil et al. |
| 7,674,787 B2 | 3/2010 | Wang et al. |
| 8,063,045 B2 | 11/2011 | Aranyi et al. |
| 8,415,349 B2 | 4/2013 | Tang et al. |
| 2005/0256166 A1 | 11/2005 | Nakai et al. |
| 2008/0300251 A1 | 12/2008 | Sattigeri et al. |
| 2009/0176847 A1 | 7/2009 | Tang et al. |
| 2013/0178500 A1 | 7/2013 | Lu et al. |

FOREIGN PATENT DOCUMENTS

| | | |
|---|---|---|
| CN | 101239937 B2 | 5/2010 |
| CN | 102188705 A | 9/2011 |
| GB | 1125716 A | 8/1968 |
| WO | 2004111041 A | 12/2004 |

OTHER PUBLICATIONS

Hirao et al., Combination Therapy with a Dipeptidyl Peptidase-4 Inhibitor, Sulfonylurea, and Metformin Markedly Improves HbA1c Levels in Japanese Patients with Type 2 Diabetes Mellitus. Japanese Clinical Medicine, 2012, 3, 1-7.*

Gareth D. Probert, et al, The Tandem Insertion of Trimethylsilylcyanide and Alkenes, Alkynes, Isocyanates or Ketons into Zirconacyclo-pentanes and -pentenes, Tetrahedron Letters, vol. 36 No. 23, p. 4113-4116, 1995.

Yoshiji Takemoto, et al, CAN-mediated tandem 5-exo-cyclisation of tertiary aminocyclopropanes: novel accelerative effect of an N-benzyl group for oxidative ring-opening, Chem. Commun., p. 651-652, 1998.

The extended European Search report of EP13809973, Feb. 29, 2016.

Tang et al., Synthesis and Biological Evaluation of Bicyclo[3.3.0]Octane Derivatives as Dipeptidyl Peptidase 4 Inhibitors for the Treatment of Type 2 Diabetes, Bioorg. Med. Chem. Lett., 2010, vol. 20, p. 3521-3525.

* cited by examiner

HEXAHYDROPENTALENO DERIVATIVES, PREPARATION METHOD AND USE IN MEDICINE THEREOF

PRIOR RELATED APPLICATIONS

This is a U.S. national stage application of the International Patent Application No. PCT/CN2013/077899, filed Jun. 25, 2013, which claims priority to Chinese Patent Application Serial No. 201210207680.5, filed on Jun. 25, 2012, entitled "Hexahydropentaleno Derivatives, Preparation Methods And Uses In Medicine", and Chinese Patent Application Serial No. 201310116954.4, filed on Apr. 3, 2013, entitled "Hexahydropentaleno Derivatives, Preparation Methods And Uses In Medicine", all of which are hereby incorporated by reference in their entireties.

FIELD OF THE INVENTION

This invention relates to novel hexahydropentaleno derivatives, preparation methods thereof, and pharmaceutical compositions comprising the derivatives, and their uses as therapeutic agents, particularly as dipeptidyl peptidase IV inhibitors.

BACKGROUND OF THE INVENTION

Diabetes refers to a disease process derived from multiple causative factors. Generally speaking, there are two types of diabetes: type I and type II. Type I diabetes, also known as insulin-dependent diabetes mellitus (IDDM), is characterized by loss of pancreatic β-cells which are damaged in the process of autoimmunity. Type II diabetes, also known as non insulin dependent diabetic mellitus (NIDDM), which is more common and a long-term and progressive metabolic disease, is characterized by hyperglycemia, hyperlipidemia and insulin resistance. The typical symptoms of type II diabetes comprise polyuria, polydipsia and bulimia.

Incretin plays an important role in regulating blood sugar balance in normal and pathological states. Glucagon-like peptide-1 (GLP-1) and glucose-dependent insulinotropic polypeptide are two incretins released from intestine after food intake and have influence on insulin secretion. GLP-1 reduces hyperglycemia by promoting insulin secretion and reducing glucagon secretion in a glucose-dependent way. Meanwhile, GLP-1 can slow gastric emptying, suppress appetites, increase satiety and promote weight loss. In animal studies, GLP-1 is of nutritional function on β-cells, which increases the likelihood of improving disease's symptoms by increasing the density and function of β-cells. Recently, researches indicated that GLP-1 is beneficial to cardiovascular system. The finding is very important because cardiovascular complication is one of the leading causes of death in diabetic patients. In short, GLP-1 has many benefits which make a lot of differences compared to existing therapeutic agents. However, GLP-1 is not used clinically because it could be degraded quickly by serine proteinase such as dipeptidyl peptidase-IV (DPP-IV) distributed widely in vivo and loses activity. Therefore, researchers have focused on developing GLP-1 analogues which are long lasting and resistant to peptidase degradation, and are dipeptidyl peptidase-IV inhibitors.

X-Proline dipeptide can be removed from N-terminus of polypeptide by dipeptidyl peptidase-IV which is an exopeptidase of glycoprotein and serine in the cell membrane. DPP-IV is widely distributed all over the body tissues comprising endothelial cells of intestine and intestinal mucosal vessel. DPP-IV is expressed in T-cells of cardiovascular system, which is equated with T cell activation marker CD26. The data of a model of the cardiovascular system indicate that DPP-IV has a potential coactivated effect during T cell activation process. In addition, DPP-IV also shows degradation of polypeptide of immunomodulator, endocrine and nerve.

DPP-IV inhibitors could increase the level of GLP-1 which is undegraded and has biological activity, and provide alternative therapies for type II diabetes. In addition, DPP-IV inhibitors are effective orally compared with incretin analogues. Glucose control could be improved by inhibiting the activity of DPP-IV. The advantage of DPP-IV inhibitors is that the release of insulin may be increased. Meanwhile, the DPP-IV inhibitors would not increase the risk of hypoglycemia. However, DPP-IV is as a member of the exopeptidase family, there are needs for DPP-IV inhibitors having high selectivity in inhibiting only the activity of DPP-IV and having no effect on other DPPs.

SUMMARY OF THE INVENTION

Accordingly, the technical problems to be solved by the present invention are to provide novel hexahydropentaleno derivatives, which could be used as DPP-IV inhibitors.

In one aspect, provided herein is a compound having Formula (I), or a stereoisomer, a geometric isomer, a tautomer, a racemate, an N-oxide, a hydrate, a solvate, a metabolite, a pharmaceutically acceptable salt or a prodrug thereof,

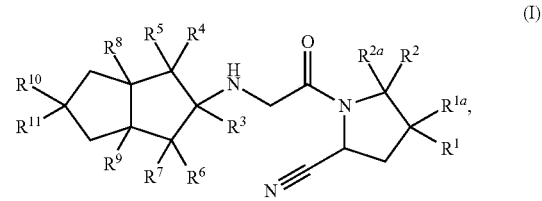

wherein each of $R^1$ and $R^{1a}$ is independently H, F, Cl or $C_{1-4}$ alkyl; each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-6 membered ring; each of $R^1$ and $R^{2a}$ is H, wherein the 3-6 membered ring optionally contains one or more heteroatoms independently selected from N, O and S, and wherein the 3-6 membered ring is optionally substituted with one or more substituents independently selected from H, $C_{1-4}$ alkyl, aryl, heteroaryl, haloalkyl, haloalkoxy, hydroxy, amino, alkyamino, $R^{14}C(=O)NH—$, $R^{14}R^{15}NC(=O)—$, cyano, alkoxy, aryloxy, aminoalkyl, hydroxyalkyl, heterocyclyl, carboxy, $—C(=O)O—C_{1-4}$ alkyl, F, Cl, Br and I, or $R^1$ and $R^{1a}$, together with the carbon atom to which they are attached, form a 3-6 membered ring, and $R^2$ and $R^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from $C_{1-4}$ alkyl, aryl, heteroaryl, haloalkyl, haloalkoxy, hydroxy, amino, alkylamino, $R^{14}C(O)NH—$, $R^{14}R^{15}NC(=O)—$, cyano, alkoxy, aryloxy, aminoalkyl, hydroxyalkyl, heterocyclyl, carboxy, —C(=O)O—C$_{1-4}$ alkyl, F, Cl, Br and I;

wherein R$^3$ is C$_{1-4}$ alkyl; each of R$^4$, R$^5$, R$^6$ and R$^7$ is independently H, hydroxy, C$_{1-4}$ alkyl, cycloalkyl or heterocyclyl, and wherein optionally each of the C$_{1-4}$ alkyl, cycloalkyl and heterocyclyl is substituted with one or more substituents independently selected from H, C$_{1-4}$ alkyl, F, Cl, Br, I, aryl, hydroxy, nitro, cyano, amino, C$_{1-3}$ alkylamino, R$^{14}$C(=O)NH—, alkoxy, aryloxy, heterocyclyl, carboxy and —C(=O)O—C$_{1-4}$ alkyl, or R$^3$ is H; R$^4$ and R$^5$, together with the carbon atom to which they are attached, form a 3-8 membered ring; and R$^6$ and R$^7$, together with the carbon atom to which they are attached, form a 3-8 membered ring, wherein each of the 3-8 membered rings optionally and independently contains one or more heteroatoms independently selected from N, O and S, and wherein each of the 3-8 membered rings is optionally and independently substituted with one or more substituents independently selected from H, C$_{1-4}$ alkyl, aryl, heteroaryl, haloalkyl, haloalkoxy, hydroxy, amino, alkylamino, R$^{14}$C(O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, F, Cl, Br, I and —NR$^{12}$R$^{13}$, or R$^3$ is H; R$^4$ and R$^5$, together with the carbon atom to which they are attached form a 3-8 membered ring, wherein the 3-8 membered ring optionally contains one or more heteroatoms independently selected from N, O and S, and wherein the 3-8 membered ring is optionally substituted with one or more substituents independently selected from H, C$_{1-4}$ alkyl, aryl, heteroaryl, haloalkyl, haloalkoxy, hydroxy, amino, alkylamino, R$^{14}$C(=O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, F, Cl, Br, I and —NR$^{12}$R$^{13}$; each of R$^6$ and R$^7$ is independently H, hydroxy, C$_{1-4}$ alkyl, cycloalkyl or heterocyclyl, wherein each of the C$_{1-4}$ alkyl, cycloalkyl and heterocyclyl is optionally substituted with one or more substituents independently selected from H, C$_{1-4}$ alkyl, F, Cl, Br, I, aryl, hydroxy, nitro, cyano, amino, C$_{1-3}$ alkylamino, R$^{14}$C(=O)NH—, alkoxy, aryloxy, heterocyclyl, carboxy and —C(=O)O—C$_{1-4}$ alkyl, or R$^3$ is H; R$^6$ and R$^7$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C$_{1-4}$ alkyl, aryl, heteroaryl, haloalkyl, haloalkoxy, hydroxy, amino, alkylamino, R$^{14}$C(=O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, F, Cl, Br, I and —NR$^{12}$R$^{13}$; each of R$^4$ and R$^5$ is independently H, hydroxy, C$_{1-4}$ alkyl, cycloalkyl or heterocyclyl, wherein each of the C$_{1-4}$ alkyl, cycloalkyl and heterocyclyl is optionally substituted with one or more substituents independently selected from H, C$_{1-4}$ alkyl, F, Cl, Br, I, aryl, hydroxy, nitro, cyano, amino, C$_{1-3}$ alkylamino, R$^{14}$C(=O)NH—, alkoxy, aryloxy, heterocyclyl, carboxy and —C(=O)O—C$_{1-4}$ alkyl;

wherein each of R$^8$ and R$^9$ is independently H or methyl;

wherein each of R$^{10}$ and R$^{11}$ is independently H, hydroxy, C$_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_p$O-heteroaryl, alkenyl, alkynyl, cyano, —OR$^{14}$, —(CH$_2$)$_p$C(=O)OR$^{14}$, —(CH$_2$)$_p$OC(=O)R$^{14}$, —(CH$_2$)$_p$C(=O)NR$^{14}$R$^{15}$, —(CH$_2$)$_p$OC(=O)NR$^{14}$R$^{15}$, —C(=O)R$^{14}$, —N(R$^{14}$)C(=O)R$^{15}$, —N(R$^{15}$)C(=O)OR$^{15}$, —OC(=O)OR$^{14}$, —OC(=O)NR$^{14}$R$^{15}$ or —NR$^{14}$R$^{15}$, and wherein each of the C$_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_r$O-heteroaryl, alkenyl and alkynyl is optionally substituted with one or more substituents independently selected from H, C$_{1-6}$ alkyl, aryl, heteroaryl, haloalkyl, haloalkoxy, hydroxy, amino, alkylamino, R$^{14}$C(=O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, halogen and —NR$^{12}$R$^{13}$, or R$^{10}$ and R$^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, R$^{14}$C(=O)NH—, R$^{14}$R$^{15}$NC(=O)—, cyano, aminoalkyl, hydroxyalkyl, heterocyclyl, trifluoromethyl, carboxy, —C(=O)O—C$_{1-4}$ alkyl and —NR$^{12}$R$^{13}$;

wherein each R$^{12}$, R$^{13}$, R$^{14}$ and R$^{15}$ is independently H, C$_{1-6}$ alkyl, —(CH$_2$)$_p$—C$_{3-6}$ cycloalkyl, aryl, heteroaryl or heterocyclyl, and wherein each of the C$_{1-6}$ alkyl, —(CH$_2$)$_p$—C$_{3-6}$ cycloalkyl, aryl, heteroaryl and heterocyclyl is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, heterocycloalkoxy, trifluoromethyl, carboxy, —C(=O)O—C$_{1-4}$ alkyl and —NR$^{12'}$R$^{13'}$, or R$^{12}$ and R$^{13}$, together with the nitrogen atom to which they are attached, form a 3-8 membered heterocyclic ring; R$^{14}$ and R$^{15}$, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —C(=O)O—C$_{1-4}$ alkyl;

wherein each of R$^{12'}$ and R$^{13'}$ is independently H, C$_{1-4}$ alkyl, cycloalkyl, heterocyclyl, aryl or heteroaryl;

wherein r is 1, 2, 3 or 4; and wherein p is 0, 1, 2, 3 or 4.

In some embodiments, provided herein is a compound having Formula (IA) or a stereoisomer, a geometric isomer, a tautomer, a racemate, an N-oxide, a hydrate, a solvate, a metabolite, a pharmaceutically acceptable salt or a prodrug thereof,

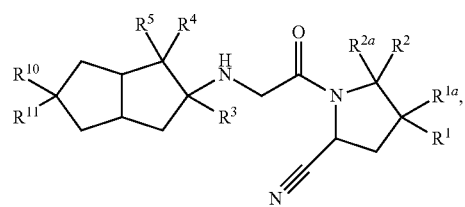

(IA)

wherein each of $R^1$ and $R^{1a}$ is independently H, F, Cl or $C_{1-4}$ alkyl; each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-6 membered ring; each of $R^1$ and $R^{2a}$ is H, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkyamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $—C(=O)O—C_{1-4}$ alkyl, F, Cl, Br and I; or $R^1$ and $R^{1a}$, together with the carbon atom to which they are attached, form a 3-6 membered ring, and $R^2$ and $R^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $—C(=O)O—C_{1-4}$ alkyl, F, Cl, Br and I;

wherein $R^3$ is $C_{1-4}$ alkyl; each of $R^4$ and $R^5$ is independently H, hydroxy, $C_{1-4}$ alkyl, $C_{3-6}$ cycloalkyl or $C_{2-5}$ heterocyclyl, and wherein each of the $C_{1-4}$ alkyl, $C_{3-6}$ cycloalkyl and $C_{2-5}$ heterocyclyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C(=O)NH—$, $C_{1-3}$ alkoxy, $C_{6-10}$ aryloxy, $C_{2-5}$ heterocyclyl, carboxy and $—C(=O)O—C_{1-4}$ alkyl, or $R^3$ is H; $R^4$ and $R^5$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $—C(=O)O—C_{1-4}$ alkyl, F, Cl, Br, I and $—NR^{12}R^{13}$;

wherein each of $R^{10}$ and $R^{11}$ is independently H, hydroxy, $C_{1-6}$ alkyl, $C_{3-6}$ cycloalkyl, $C_{2-5}$ heterocyclyl, $C_{6-10}$ aryl, $C_{1-9}$ heteroaryl, $—(CH_2)_r—C_{6-10}$ aryl, $—(CH_2)_rO—C_{6-10}$ aryl, $—(CH_2)_r—C_{1-9}$ heteroaryl, $—(CH_2)_rO—C_{1-9}$ heteroaryl, $C_{2-4}$ alkenyl, $C_{2-4}$ alkynyl, cyano, $—OR^{14}$, $—(CH_2)_pC(=O)OR^{14}$, $—(CH_2)_pOC(=O)R^{14}$, $—(CH_2)_pC(=O)NR^{14}R^{15}$, $—(CH_2)_pOC(=O)NR^{14}R^{15}$, $—C(=O)R^{14}$, $—N(R^{14})C(=O)R^{15}$, $—N(R^{15})C(=O)OR^{15}$, $—OC(=O)OR^{14}$, $—OC(=O)NR^{14}R^{15}$ or $—NR^{14}R^{15}$ and wherein each of the $C_{1-6}$ alkyl, $C_{3-6}$ cycloalkyl, $C_{2-5}$ heterocyclyl, $C_{6-10}$ aryl, $C_{1-9}$ heteroaryl, $—(CH_2)_r—C_{6-10}$ aryl, $—(CH_2)_rO—C_{6-10}$ aryl, $—(CH_2)_r—C_{1-9}$ heteroaryl, $—(CH_2)_rO—C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $—C(=O)O—C_{1-4}$ alkyl, halogen and $—NR^{12}R^{13}$, or $R^{10}$ and $R^{11}$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy, $—C(=O)O—C_{1-4}$ alkyl and $—NR^{12}R^{13}$;

wherein each $R^{12}$, $R^{13}$, $R^{14}$ and $R^{15}$ is independently H, $C_{1-6}$ alkyl, $—(CH_2)_p—C_{3-6}$ cycloalkyl, $C_{6-10}$ aryl, $C_{1-9}$ heteroaryl or $C_{2-5}$ heterocyclyl, and wherein each of the $C_{1-6}$ alkyl, $—(CH_2)_p—C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, $—C(=O)O—C_{1-4}$ alkyl and $—NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and $—C(=O)O—C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and wherein p is 0, 1, 2, 3 or 4.

In other embodiments, each of $R^1$ and $R^{1a}$ is independently H, F, Cl or $C_{1-4}$ alkyl; each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-5 membered carboatomic ring; each of $R^1$ and $R^{2a}$ is H, wherein the 3-5 membered carboatomic ring is optionally substituted with one or more substituents independently selected from H, $C_{1-4}$ alkyl, $C_{1-3}$ haloalkyl, hydroxy, amino, F, Cl, Br and I;

wherein $R^3$ is $C_{1-4}$ alkyl; each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C(=O)NH—$, $C_{1-3}$ alkoxy, $C_{6-10}$ aryloxy, $C_{2-5}$ heterocyclyl, carboxy and $—C(=O)O—C_{1-4}$ alkyl, or $R^3$ is H; $R^4$ and $R^5$, together with the carbon atom to which they are attached, form a 3-5 membered ring, wherein the 3-5 membered ring optionally contains one or more heteroatoms independently selected from N, O and S, and wherein the 3-5 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, $C_{3-6}$ cycloalkyl, $C_{2-5}$ heterocyclyl, —$(CH_2)_r$—$C_{6-10}$ aryl, —$(CH_2)_rO$—$C_{6-10}$ aryl, —$(CH_2)_r$—$C_{1-9}$ heteroaryl, —$(CH_2)_rO$—$C_{1-9}$ heteroaryl, $C_{2-4}$ alkynyl, cyano, —$OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_rO$—$C_{6-10}$ aryl, —$(CH_2)$—$C_{1-9}$ heteroaryl, —$(CH_2)_rO$—$C_{1-9}$ heteroaryl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, halogen and —$NR^{12}R^{13}$, or $R^{10}$ and $R^{11}$, together with the carbon atom to which they are attached, form a 3-5 membered ring, wherein the 3-5 membered ring optionally contains one or more heteroatoms independently selected from N, O and S, and wherein the 3-5 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and wherein p is 0, 1, 2, 3 or 4.

In other embodiments, each of $R^1$ and $R^{1a}$ is independently H, F or $C_{1-4}$ alkyl; each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3 membered unsubstituted carboatomic ring; each of $R^1$ and $R^{2a}$ is H;

wherein $R^3$ is $C_{1-4}$ alkyl; each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br and I, or $R^3$ is H; $R^4$ and $R^5$, together with the carbon atom to which they are attached, form a 3 membered carboatomic ring, wherein the 3 membered carboatomic ring is optionally substituted with one or more substituents independently selected from $C_{1-4}$ alkyl, F, Cl, Br and I;

wherein each of $R^{10}$ and $R^{11}$ is independently H, hydroxy, $C_{1-6}$ alkyl, $C_{2-4}$ alkynyl, cyano, —$OR^{14}$, —$(CH_2)_pOC(=O)R^{14}$, —$(CH_2)_pC(=O)NR^{14}R^{15}$, —$(CH_2)_pOC(=O)NR^{14}R^{15}$ or —$C(=O)R^{14}$, and wherein each of the $C_{1-6}$ alkyl and $C_{2-4}$ alkynyl is optionally substituted with one or more substituents independently selected from H, $C_{1-6}$ alkyl, $C_{6-10}$ aryl, $C_{1-3}$ haloalkyl, hydroxy, amino, $C_{1-3}$ alkylamino, cyano, $C_{1-3}$ alkoxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —$NR^{12}R^{13}$, or $R^{10}$ and $R^{11}$, together with the carbon atom to which they are attached, form a 3-4 membered ring, wherein the 3-4 membered ring optionally contains one or more heteroatoms independently selected from N, O and S, and wherein the 3-4 membered ring is optionally substituted with one or more substituents independently selected from H, $C_{1-4}$ alkyl, F, Cl, Br, I, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-4}$ alkyl or —$(CH_2)_p$—$C_{3-6}$ cycloalkyl, and wherein each of the $C_{1-4}$ alkyl and —$(CH_2)_p$—$C_{3-6}$ cycloalkyl is optionally substituted with one or more substituents independently selected from H, $C_{1-4}$ alkyl, $C_{3-6}$ cycloalkyl, F, Cl, Br, I, hydroxy, amino, $C_{1-3}$ alkylamino, cyano, $C_{1-3}$ aminoalkyl, $C_{1-3}$ hydroxyalkyl, trifluoromethyl, carboxy and —C(=O)O—$C_{1-4}$ alkyl;

wherein r is 1, 2, 3 or 4; and wherein p is 0, 1, 2, 3 or 4.

In some embodiments, provided herein is a pharmaceutically acceptable salt of the compound having Formula (I) or Formula (IA), wherein the pharmaceutically acceptable salt is hydrochloride, sulfate, nitrate, phosphate, metaphosphate, mesilate, ethyl sulfonate, citrate, benzene sulfonate, p-toluene sulfonate, malate, tartrate, succinate, fumarate, acetate, glycollate, hydroxyethyl sulfonate, maleate, lactate, lactobionate, trifluoroacetate or a combination thereof.

In some embodiments, provided herein is a compound having one of structures 1 to 20, or a stereoisomer, a geometric isomer, a tautomer, a racemate, an N-oxide, a hydrate, a solvate, a metabolite, a pharmaceutically acceptable salt or a prodrug thereof:

| Example No. | Structure | Name |
|---|---|---|
| 1 | 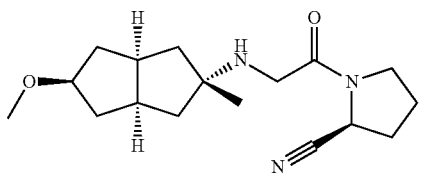 [SMILES: CO[C@@H]1C[C@@H]2C[C@@](C)(NCC(=O)N3CCC[C@H]3C#N)C[C@@H]2C1] | (S)-1-(2-(((2r,3aR,5S,6aS)-5-methoxy-2-methyloctahydropentalen-2-yl)amino)acetyl)pyrrolidine-2-carbonitrile |
| 2 | 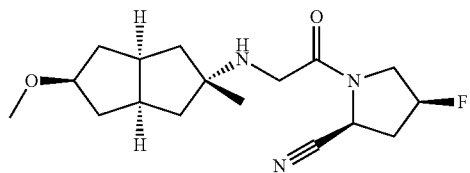 [SMILES: CO[C@@H]1C[C@@H]2C[C@@](C)(NCC(=O)N3C[C@@H](F)C[C@H]3C#N)C[C@@H]2C1] | (2S,4S)-4-fluoro-1-(2-(((2r,3aR,5S,6aS)-5-methoxy-2-methyloctahydropentalen-2-yl)amino)acetyl)pyrrolidine-2-carbonitrile |
| 3 | 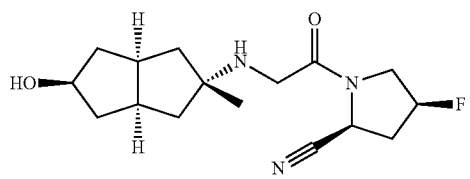 [SMILES: C[C@@]1(NCC(=O)N2C[C@@H](F)C[C@H]2C#N)C[C@H]2C[C@@H](O)C[C@H]2C1] | (2S,4S)-4-fluoro-1-(2-(((2r,3aR,5S,6aS)-5-hydroxy-2-methyloctahydropentalen-2-yl)amino)acetyl)pyrrolidine-2-carbonitrile |
| 4 | 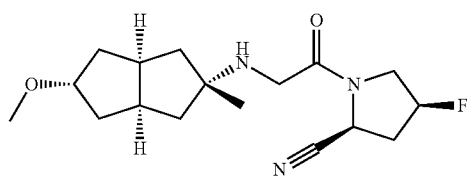 [SMILES: CO[C@H]1C[C@@H]2C[C@@](C)(NCC(=O)N3C[C@@H](F)C[C@H]3C#N)C[C@@H]2C1] | (2S,4S)-4-fluoro-1-(2-(((2r,3aR,5R,6aS)-5-methoxy-2-methyloctahydropentalen-2-yl)amino)acetyl)pyrrolidine-2-carbonitrile |
| 5 | 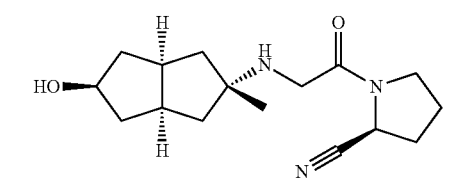 [SMILES: C[C@@]1(NCC(=O)N2CCC[C@H]2C#N)C[C@H]2C[C@@H](O)C[C@H]2C1] | (S)-1-(2-(((2r,3aR,5S,6aS)-5-hydroxy-2-methyloctahydropentalen-2-yl)amino)acetyl)pyrrolidine-2-carbonitrile |
| 6 | 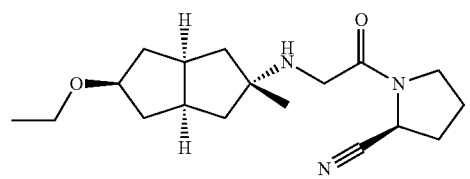 [SMILES: CCO[C@@H]1C[C@@H]2C[C@@](C)(NCC(=O)N3CCC[C@H]3C#N)C[C@@H]2C1] | (S)-1-(2-(((2r,3aR,5S,6aS)-5-ethoxy-2-methyloctahydropentalen-2-yl)amino)acetyl)pyrrolidine-2-carbonitrile |
| 7 | 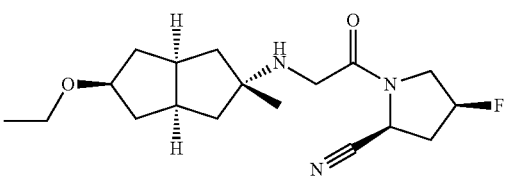 [SMILES: CCO[C@@H]1C[C@@H]2C[C@@](C)(NCC(=O)N3C[C@@H](F)C[C@H]3C#N)C[C@@H]2C1] | (2S,4S)-1-(2-(((2r,3aR,5S,6aS)-5-ethoxy-2-methyloctahydropentalen-2-yl)amino)acetyl)-4-fluoropyrrolidine-2-carbonitrile |
| 8 | 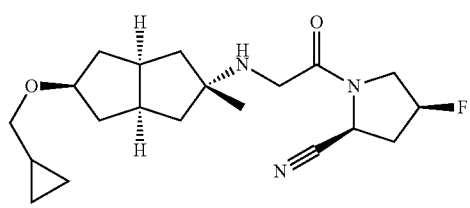 [SMILES: C[C@@]1(NCC(=O)N2C[C@@H](F)C[C@H]2C#N)C[C@H]2C[C@@H](OCC3CC3)C[C@H]2C1] | (2S,4S)-1-(2-(((2r,3aR,5S,6aS)-5-(cyclopropylmethoxy)-2-methyloctahydropentalen-2-yl)amino)acetyl)-4-fluoropyrrolidine-2-carbonitrile |

| Example No. | Structure | Name |
|---|---|---|
| 9 | 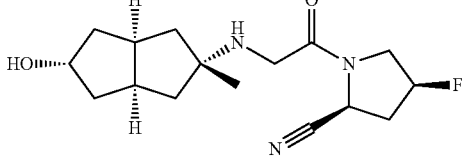 | (2S,4S)-4-fluoro-1-(2-(((2r,3aR,5R,6aS)-5-hydroxy-2-methyloctahydropentalen-2-yl)amino)acetyl)pyrrolidine-2-carbonitrile |
| 10 | 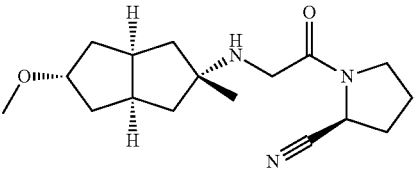 [SMILES: CO[C@H]1C[C@@H]2C[C@@](C)(NCC(=O)N3CCC[C@H]3C#N)C[C@@H]2C1] | (S)-1-(2-(((2r,3aR,5R,6aS)-5-methoxy-2-methyloctahydropentalen-2-yl)amino)acetyl)pyrrolidine-2-carbonitrile |
| 11 | 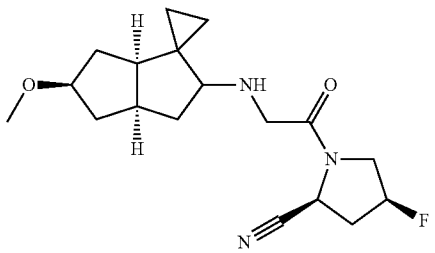 [SMILES: CO[C@@H]1C[C@@H]2CC(NCC(=O)N3C[C@@H](F)C[C@H]3C#N)C3(CC3)[C@@H]2C1] | (2S,4S)-4-fluoro-1-(2-(((3a'S,5'R,6a'R)-5'-methoxyhexahydro-2'H-spiro[cyclopropane-1,1'-pentalen]-2'-yl)amino)acetyl)pyrrolidine-2-carbonitrile |
| 12 | 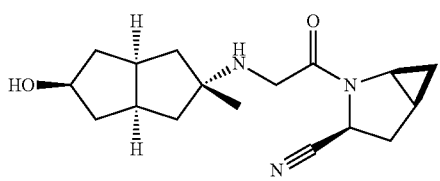 | (1S,3S,5S)-2-(2-(((2r,3aR,5S,6aS)-5-hydroxy-2-methyloctahydropentalen-2-yl)amino)acetyl)-2-azabicyclo[3.1.0]hexane-3-carbonitrile |
| 13 | 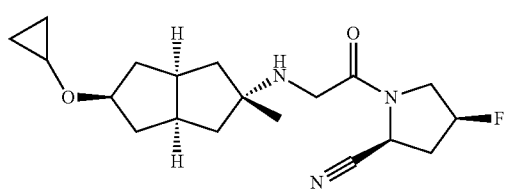 [SMILES: C[C@@]1(NCC(=O)N2C[C@@H](F)C[C@H]2C#N)C[C@H]2C[C@@H](OC3CC3)C[C@H]2C1] | (2S,4S)-1-(2-(((2r,3aR,5S,6aS)-5-cyclopropoxy-2-methyloctahydropentalen-2-yl)amino)acetyl)-4-fluoropyrrolidine-2-carbonitrile |
| 14 | 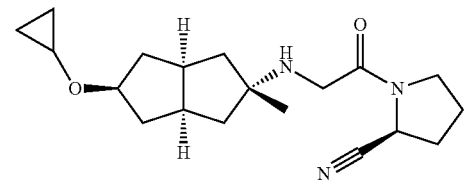 [SMILES: C[C@@]1(NCC(=O)N2CCC[C@H]2C#N)C[C@H]2C[C@@H](OC3CC3)C[C@H]2C1] | (S)-1-(2-(((2r,3aR,5S,6aS)-5-cyclopropoxy-2-methyloctahydropentalen-2-yl)amino)acetyl)pyrrolidine-2-carbonitrile |
| 15 | 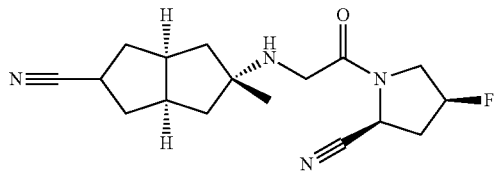 [SMILES: C[C@@]1(NCC(=O)N2C[C@@H](F)C[C@H]2C#N)C[C@H]2CC(C#N)C[C@H]2C1] | (2S,4S)-1-(2-(((2s,3aR,6aS)-5-cyano-2-methyloctahydropentalen-2-yl)amino)acetyl)-4-fluoropyrrolidine-2-carbonitrile |
| 16 | 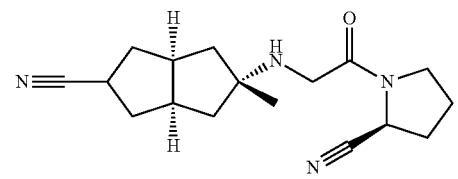 [SMILES: C[C@@]1(NCC(=O)N2CCC[C@H]2C#N)C[C@H]2CC(C#N)C[C@H]2C1] | (2S)-1-(2-(((2s,3aR,6aS)-5-cyano-2-methyloctahydropentalen-2-yl)amino)acetyl)pyrrolidine-2-carbonitrile |

| Example No. | Structure | Name |
|---|---|---|
| 17 | 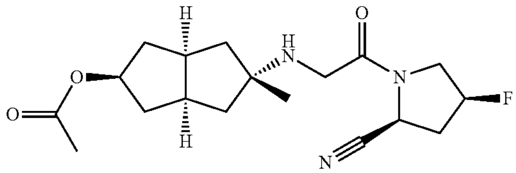 [SMILES: CC(=O)O[C@@H]1C[C@@H]2C[C@@](C)(NCC(=O)N3C[C@@H](F)C[C@H]3C#N)C[C@@H]2C1] | (2S,3aR,5r,6aS)-5-((2-((2S,4S)-2-cyano-4-fluoropyrrolidin-1-yl)-2-oxoethyl)amino)-5-methyloctahydropentalen-2-yl acetate |
| 18 | 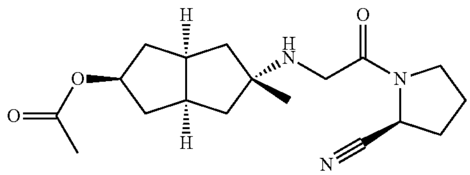 [SMILES: CC(=O)O[C@@H]1C[C@@H]2C[C@@](C)(NCC(=O)N3CCC[C@H]3C#N)C[C@@H]2C1] | (2S,3aR,5r,6aS)-5-((2-((S)-2-cyanopyrrolidin-1-yl)-2-oxoethyl)amino)-5-methyloctahydropentalen-2-yl acetate |
| 19 | 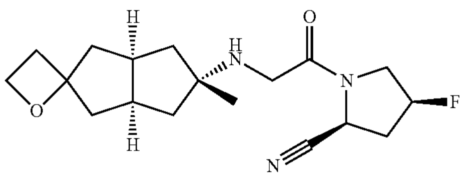 [SMILES: C[C@@]1(NCC(=O)N2C[C@@H](F)C[C@H]2C#N)C[C@H]2CC3(CCO3)C[C@H]2C1] | (2S,4S)-4-fluoro-1-(2-(((3a'R,5'r,6a'S)-5'-methylhexahydro-1'H-spiro[oxetane-2,2'-pentalen]-5'-yl)amino)acetyl)pyrrolidine-2-carbonitrile |
| 20 | 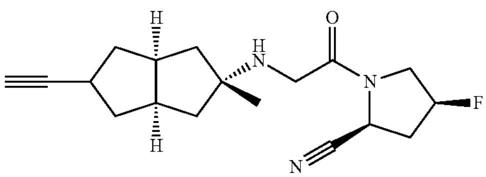 [SMILES: C#CC1C[C@@H]2C[C@@](C)(NCC(=O)N3C[C@@H](F)C[C@H]3C#N)C[C@@H]2C1] | (2S,4S)-1-(2-(((2s,3aR,6aS)-5-ethynyl-2-methyloctahydropentalen-2-yl)amino)acetyl)-4-fluoropyrrolidine-2-carbonitrile |

In other aspect, provided herein is a process for preparing the compound of Formula (IA), comprising the step of reacting a compound of Formula (1-1d) or a stereoisomer thereof with an N-haloacetyl-2-cyano-pyrrolidine derivative having Formula (II) in the presence of a base in a polar solvent to give the compound of Formula (IA);

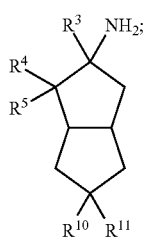

(1-1d)

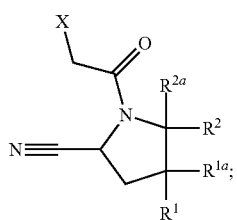

(II)

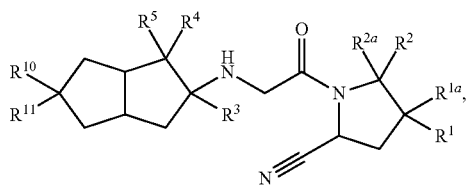

(IA)

wherein each of $R^1$ and $R^{1a}$ is independently H, F, Cl or $C_{1-4}$ alkyl; each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-6 membered ring; each of $R^1$ and $R^{2a}$ is H, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkyamino, $R^{14}C(O)NH-$, $R^{14}R^{15}NC(=O)-$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $-C(=O)O-C_{1-4}$ alkyl, F, Cl, Br and I, or $R^1$ and $R^{1a}$, together with the carbon atom to which they are attached, form a 3-6 membered ring, and $R^2$ and $R^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(O)NH$—, $R^{14}R^{15}NC(=O)$—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br and I;

wherein X is halogen;

wherein $R^3$ is $C_{1-4}$ alkyl; each of $R^4$ and $R^5$ is independently H, hydroxy, $C_{1-4}$ alkyl, $C_{3-6}$ cycloalkyl or $C_{2-5}$ heterocyclyl and wherein each of the $C_{1-4}$ alkyl, $C_{3-6}$ cycloalkyl and $C_{2-5}$ heterocyclyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C(=O)NH$—, $C_{1-3}$ alkoxy, $C_{6-10}$ aryloxy, $C_{2-5}$ heterocyclyl, carboxy and —C(=O)O—$C_{1-4}$ alkyl, or $R^3$ is H; $R^4$ and $R^5$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH$—, $R^{14}R^{15}NC(=O)$—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkenyl, $C_{2-4}$ alkynyl, cyano, —$OR^{14}$, —$(CH_2)_pC(=O)OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$, —$OC(=O)NR^{14}R^{15}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_rO$—$C_{6-10}$ aryl, —$(CH_2)_rO$—$C_{6-10}$ aryl, —$(CH_2)_r$—$C_{1-9}$ heteroaryl, —$(CH_2)_rO$—$C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH$—, $R^{14}R^{15}NC(=O)$—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, halogen and —$NR^{12}R^{13}$, or $R^{10}$ and $R^{11}$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH$—, $R^{14}R^{15}NC(=O)$—, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and wherein p is 0, 1, 2, 3 or 4.

In some embodiments, provided herein is a process for preparing the compound of Formula (IA), wherein the N-haloacetyl-2-cyano-pyrrolidine derivative is N-(2-chloroacetyl)pyrrolidine-2-carbonitrile, N-(2-bromoacetyl)pyrrolidine-2-carbonitrile, N-(2-chloroacetyl)-4-fluoropyrrolidine-2-carbonitrile, N-(2-bromoacetyl)-4-fluoropyrrolidine-2-carbonitrile, N-(2-chloroacetyl)-2-azabicyclo[3.1.0]hexane-3-carbonitrile, N-(2-bromoacetyl)-2-azabicyclo[3.1.0]hexane-3-carbonitrile;

wherein the polar solvent is water, formamide, dimethyl sulfoxide, acetonitrile, N,N-dimmethylformamide, methanol, ethanol, i-propanol or a combination thereof; and wherein the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof.

In some embodiments, provided herein is a process for preparing the compound of Formula (IA), further comprising reacting the compound of Formula (IA) with an acid to give an addition salt thereof, and wherein the addition salt is a hydrochloride, a sulfate, a nitrate, a phosphate, a metaphosphate, a mesilate, a ethyl sulfonate, a citrate, a benzene sulfonate, a p-toluene sulfonate, a malate, a tartrate, a succinate, a fumarate, a acetate, a glycollate, a hydroxyethyl sulfonate, a maleate, a lactate, a lactobionate or a trifluoroacetate.

In other aspect, provided herein is a compound of Formula (1-1d) or a stereoisomer thereof:

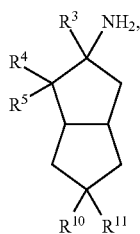

(1-1d)

wherein R³ is C₁₋₄ alkyl; each of R⁴ and R⁵ is independently H, hydroxy, C₁₋₄ alkyl, cycloalkyl or heterocyclyl, and wherein each of the C₁₋₄ alkyl, cycloalkyl and heterocyclyl is optionally substituted with one or more substituents independently selected from H, C₁₋₄ alkyl, F, Cl, Br, I, aryl, hydroxy, nitro, cyano, amino, C₁₋₃ alkylamino, R¹⁴C(═O)NH—, alkoxy, aryloxy, heterocyclyl, carboxy and —C(═O)O—C₁₋₄ alkyl, or R³ is H; R⁴ and R⁵, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C₁₋₄ alkyl, aryl, heteroaryl, haloalkyl, haloalkoxy, hydroxy, amino, alkylamino, R¹⁴C(═O)NH—, R¹⁴R¹⁵NC(═O)—, cyano, alkoxy, aryloxy, aminoalkyl, hydroxyalkyl, heterocyclyl, carboxy, —C(═O)O—C₁₋₄ alkyl, F, Cl, Br, I and —NR¹²R¹³;

wherein each of R¹⁰ and R¹¹ is independently H, hydroxy, C₁₋₆ alkyl, cycloalkyl, heterocyclyl, aryl, heteroaryl, —(CH₂)ᵣ-aryl, —(CH₂)ᵣO-aryl, —(CH₂)ᵣ-heteroaryl, —(CH₂)ᵣO-heteroaryl, alkenyl, alkynyl, cyano, —OR¹⁴, —(CH₂)ₚC(═O)OR¹⁴, —(CH₂)ₚOC(═O)R¹⁴, —(CH₂)ₚC(═O)NR¹⁴R¹⁵, —(CH₂)ₚOC(═O)NR¹⁴R¹⁵, —C(═O)R¹⁴, —N(R¹⁴)C(═O)R¹⁵, —N(R¹⁵)C(═O)OR¹⁵, —OC(═O)OR¹⁴, —OC(═O)NR¹⁴R¹⁵ or —NR¹⁴R¹⁵, and wherein each of the C₁₋₆ alkyl, cycloalkyl, heterocyclyl, aryl, heteroaryl, —(CH₂)ᵣ-aryl, —(CH₂)ᵣO-aryl, —(CH₂)ᵣ-heteroaryl, —(CH₂)ᵣO-heteroaryl, alkenyl and alkynyl is optionally substituted with one or more substituents independently selected from H, C₁₋₆ alkyl, aryl, heteroaryl, haloalkyl, haloalkoxy, hydroxy, amino, alkylamino, R¹⁴C(═O)NH—, R¹⁴R¹⁵NC(═O)—, cyano, alkoxy, aryloxy, aminoalkyl, hydroxyalkyl, heterocyclyl, carboxy, —C(═O)O—C₁₋₄ alkyl, halogen and —NR¹²R¹³, or R¹⁰ and R¹¹, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C₁₋₄ alkyl, cycloalkyl, aryl, heteroaryl, alkoxy, cycloalkoxy, aryloxy, heteroaryloxy, halogen, hydroxy, amino, alkylamino, R¹⁴C(═O)NH—, R¹⁴R¹⁵NC(═O)—, cyano, aminoalkyl, hydroxyalkyl, heterocyclyl, trifluoromethyl, carboxy, —C(═O)O—C₁₋₄ alkyl and —NR¹²R¹³;

wherein each R¹², R¹³, R¹⁴ and R¹⁵ is independently H, C₁₋₆ alkyl, —(CH₂)ₚ—C₃₋₆ cycloalkyl, aryl, heteroaryl or heterocyclyl, and wherein each of the C₁₋₆ alkyl, —(CH₂)ₚ—C₃₋₆ cycloalkyl, aryl, heteroaryl and heterocyclyl is optionally substituted with one or more substituents independently selected from H, C₁₋₄ alkyl, cycloalkyl, aryl, heteroaryl, alkoxy, cycloalkoxy, aryloxy, heteroaryloxy, halogen, hydroxy, amino, alkylamino, R¹⁴C(═O)NH—, R¹⁴R¹⁵NC(═O)—, cyano, aminoalkyl, hydroxyalkyl, heterocyclyl, heterocycloalkoxy, trifluoromethyl, carboxy, —C(═O)O—C₁₋₄ alkyl and —NR¹²ᵗR¹³ᵗ, or R¹² and R¹³, together with the nitrogen atom to which they are attached, form a 3-8 membered heterocyclic ring, and R¹⁴ and R¹⁵, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, C₁₋₄ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —C(═O)O—C₁₋₄ alkyl;

wherein each of R¹²ᵗ and R¹³ᵗ is independently H, C₁₋₄ alkyl, cycloalkyl, heterocyclyl, aryl or heteroaryl;

wherein r is 1, 2, 3 or 4; and wherein p is 0, 1, 2, 3 or 4.

In some embodiments, R³ is C₁₋₄ alkyl; each of R⁴ and R⁵ is independently H, hydroxy or C₁₋₄ alkyl, and wherein the C₁₋₄ alkyl is optionally substituted with one or more substituents independently selected from H, C₁₋₄ alkyl, F, Cl, Br, I, C₆₋₁₀ aryl, hydroxy, nitro, cyano, amino, C₁₋₃ alkylamino, R¹⁴C(═O)NH—, C₁₋₃ alkoxy, C₆₋₁₀ aryloxy, C₂₋₅ heterocyclyl, carboxy and —C(═O)O—C₁₋₄ alkyl, or R³ is H; R⁴ and R⁵, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, C₁₋₄ alkyl, C₆₋₁₀ aryl, C₁₋₉ heteroaryl, C₁₋₃ haloalkyl, C₁₋₃ haloalkoxy, hydroxy, amino, C₁₋₃ alkylamino, R¹⁴C(═O)NH—, R¹⁴R¹⁵NC(═O)—, cyano, C₁₋₃ alkoxy, C₆₋₁₀ aryloxy, C₁₋₃ aminoalkyl, C₁₋₃ hydroxyalkyl, C₂₋₅ heterocyclyl, carboxy, —C(═O)O—C₁₋₄ alkyl, F, Cl, Br, I and —NR¹²R¹³;

wherein each of R¹⁰ and R¹¹ is independently H, hydroxy, C₁₋₆ alkyl, C₃₋₆ cycloalkyl, C₂₋₅ heterocyclyl, —(CH₂)ᵣ—C₆₋₁₀ aryl, —(CH₂)ᵣO—C₆₋₁₀ aryl, —(CH₂)ᵣ—C₁₋₉ heteroaryl, —(CH₂)ᵣO—C₁₋₉ heteroaryl, C₂₋₄ alkenyl, C₂₋₄ alkynyl, cyano, —OR¹⁴, —(CH₂)ₚOC(═O)R¹⁴, —(CH₂)ₚC(═O)NR¹⁴R¹⁵, —(CH₂)ₚOC(═O)NR¹⁴R¹⁵, —C(═O)R¹⁴, —N(R¹⁴)C(═O)R¹⁵, —N(R¹⁵)═O)OR¹⁵, —OC(═O)OR¹⁴ or —NR¹⁴R¹⁵, and wherein each of the C₁₋₆ alkyl, C₃₋₆ cycloalkyl, C₂₋₅ heterocyclyl, C₆₋₁₀ aryl, C₁₋₉ heteroaryl, —(CH₂)ᵣ—C₆₋₁₀ aryl, —(CH₂)ᵣO—C₆₋₁₀ aryl, —(CH₂)ᵣ—C₁₋₉ heteroaryl, —(CH₂)ᵣO—C₁₋₉ heteroaryl, C₂₋₄ alkenyl and C₂₋₄ alkynyl is optionally substituted with one or more substituents independently selected from H, C₁₋₆ alkyl, C₆₋₁₀ aryl, C₁₋₉ heteroaryl, C₁₋₃ haloalkyl, C₁₋₃ haloalkoxy, hydroxy, amino, C₁₋₃ alkylamino, R¹⁴C(═O)NH—, R¹⁴R¹⁵NC(═O)—, cyano, C₁₋₃ alkoxy, C₆₋₁₀ aryloxy, C₁₋₃ aminoalkyl, C₁₋₃ hydroxyalkyl, C₂₋₅ heterocyclyl, carboxy, —C(═O)O—C₁₋₄ alkyl, halogen and —NR¹²R¹³, or R¹⁰ and R¹¹, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, C₁₋₄ alkyl, C₃₋₆ cycloalkyl, C₆₋₁₀ aryl, C₁₋₉ heteroaryl, C₁₋₃ alkoxy, C₃₋₆ cycloalkoxy, C₆₋₁₀ aryloxy, C₁₋₉ heteroaryloxy, halogen, hydroxy, amino, C₁₋₃ alkylamino, R¹⁴C(═O)NH—, $R^{14}R^{15}NC(=O)$—, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and
wherein p is 0, 1, 2, 3 or 4.

In other embodiments, $R^3$ is $C_{1-4}$ alkyl; each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br and I, or $R^3$ is H; $R^4$ and $R^5$, together with the carbon atom to which they are attached, form a 3 membered carboatomic ring, wherein the 3 membered carboatomic ring is optionally substituted with one or more substituents independently selected from H, $C_{1-4}$ alkyl, F, Cl, Br and I;

wherein each of $R^{10}$ and $R^{11}$ is independently H, hydroxy, $C_{1-6}$ alkyl, $C_{2-4}$ alkynyl, cyano, —$OR^{14}$, —$(CH_2)_pOC(=O)R^{14}$, —$(CH_2)_pC(=O)NR^{14}R^{15}$, —$(CH_2)_pOC(=O)NR^{14}R^{15}$ or —$C(=O)R^{14}$, and wherein each of the $C_{1-6}$ alkyl and $C_{2-4}$ alkynyl is optionally substituted with one or more substituents independently selected from H, $C_{1-6}$ alkyl, $C_{6-10}$ aryl, $C_{1-3}$ haloalkyl, hydroxy, amino, $C_{1-3}$ alkylamino, cyano, $C_{1-3}$ alkoxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —$NR^{12}R^{13}$, or $R^{10}$ and $R^{11}$, together with the carbon atom to which they are attached, form a 3-4 membered ring, wherein the 3-4 membered ring optionally contains one heteroatom independently selected from N, O and S, and wherein the 3-4 membered ring is optionally substituted with one or more substituents independently selected from H, $C_{1-4}$ alkyl, F, Cl, Br, I, hydroxy, amino, $C_{1-3}$ alkylamino, $R^{14}C(=O)NH$—, $R^{14}R^{15}NC(=O)$—, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-4}$ alkyl or —$(CH_2)_p$—$C_{3-6}$ cycloalkyl, and wherein each of the $C_{1-4}$ alkyl and —$(CH_2)_p$—$C_{3-6}$ cycloalkyl is optionally substituted with one or more substituents independently selected from H, $C_{1-4}$ alkyl, $C_{3-6}$ cycloalkyl, F, Cl, Br, I, hydroxy, amino, $C_{1-3}$ alkylamino, cyano, $C_{1-3}$ aminoalkyl, $C_{1-3}$ hydroxyalkyl, trifluoromethyl, carboxy and —C(=O)O—$C_{1-4}$ alkyl;

wherein r is 1, 2, 3 or 4; and
wherein p is 0, 1, 2, 3 or 4.

In other aspect, provided herein is a process for preparing the compound of Formula (1-1d), comprising the steps of:

(a) reacting a compound of Formula (1-1a) with a Grignard reagent having Formula $R^3$-MgX to give a compound of Formula (1-1b):

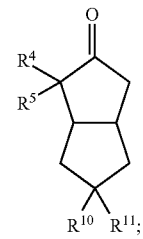
(1-1a)

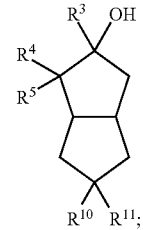
(1-1b)

(b) azidating the compound of Formula (1-1b) with sodium azide in a halohydrocarbon solvent in the presence of an acid to obtain a compound of Formula (1-1c):

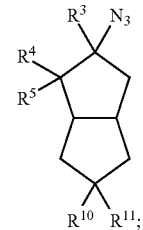
(1-1c)

and (c) reducing the compound of Formula (1-1c) or a stereoisomer thereof in a reducing system in a solvent to obtain the compound of Formula (1-1d):

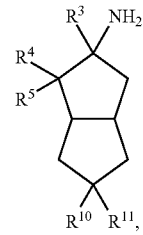
(1-1d)

wherein $R^3$ is $C_{1-4}$ alkyl; each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C(=O)NH—$, $C_{1-3}$ alkoxy, $C_{6-10}$ aryloxy, $C_{2-5}$ heterocyclyl, carboxy and —C(=O)O—$C_{1-4}$ alkyl, or $R^3$ is H; $R^4$ and $R^5$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, $C_{3-6}$ cycloalkyl, $C_{2-5}$ heterocyclyl, —$(CH_2)_r$—$C_{6-10}$ aryl, —$(CH_2)_rO$—$C_{6-10}$ aryl, —$(CH_2)_r$—$C_{1-9}$ heteroaryl, —$(CH_2)_rO$—$C_{1-9}$ heteroaryl, $C_{2-4}$ alkenyl, $C_{2-4}$ alkynyl, cyano, —$OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_rO$—$C_{6-10}$ aryl, —$(CH_2)_r$—$C_{1-9}$ heteroaryl, —$(CH_2)_rO$—$C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, halogen and —$NR^{12}R^{13}$, or $R^{10}$ and $R^{11}$, together with the carbon atom to which they are attached, form a 3-6 membered ring, wherein the 3-5 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4;

wherein p is 0, 1, 2, 3 or 4;

wherein X is Cl, Br or I; and wherein the solvent is a nonpolar solvent, a weak polar solvent or a polar solvent.

In some embodiments, the halohydrocarbon solvent is methyl chloride, dichloromethane, trichloromethane, tetrachloromethane, tribromethane, trichloroethylene, tetrachloroethylene, 1,1,1,2-tetrachloroethane, 1,1,1-trichloroethane, 1,1,2,2-tetrachloroethane, 1,1,2-trichloroethane, 1,1-dichloro-1-fluoroethane, 1,2,3-trichloropropane or 1,2-dichloroethane;

wherein the reducing system is hydrogen with a platinum on activated carbon catalyst, a sodium borohydride-copper sulfate system, lithium aluminium hydride, sodium borohydride or a combination thereof;

wherein the polar solvent is water, formamide, dimethyl sulfoxide, acetonitrile, N,N-dimethylformamide, methanol, ethanol, isopropanol or a combination thereof; and wherein the acid is sulfuric acid, hydrochloric acid, nitric acid, phosphoric acid, formic acid, acetic acid, trifluoroacetic acid, methyl sulfonic acid, benzenesulfonic acid, p-toluene sulfonic acid, 4-nitro benzoic acid or a combination thereof In some embodiments, provided herein is a process for preparing the compound of Formula (1-1d), when $R^{10}$ or $R^{11}$ of Formula (1-1c) is hydroxy, the process further comprising the steps of:

(a) condensing the compound of Formula (1-1c) with an aromatic acid in the presence of triphenylphosphine and diethyl azodicarboxylate to give an ester; and (b) hydrolyzing the ester in the presence of a base in a polar solvent to give a stereoisomer of the compound of Formula (1-1c).

In other embodiments, the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the aromatic acid is benzoic acid, p-nitrobenzoic acid, 4-methoxybenzoic acid or 4-methylbenzoic acid; and wherein the polar solvent is water, formamide, dimethyl sulfoxide, acetonitrile, N,N-dimethylformamide, methanol, ethanol, isopropanol or a combination thereof.

In other aspect, provided herein is a process for preparing the compound of Formula (1-1d), comprising the steps of:

(a) reacting a compound of Formula (1-1e) with a Grignard reagent having Formula R³-MgX to give a compound of Formula (1-1f):

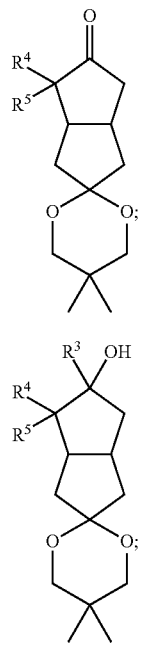

(1-1e)

(1-1f)

(b) removing the protecting group of the compound of Formula (1-1f) in the presence of an acid in a polar solvent to give a compound of Formula (1-1g):

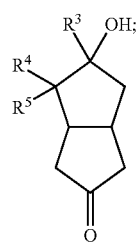

(1-1g)

(c) reducing the compound of Formula (1-1 g) in the presence of a reducing agent in a polar solvent to give a compound of Formula (1-1h):

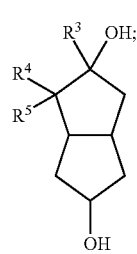

(1-1h)

(d) azidating the compound of Formula (1-1h) with sodium azide in a halohydrocarbon solvent in the presence of an acid to obtain a compound of Formula (1-1i):

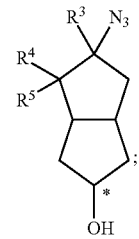

(1-1i)

and (e) reducing the compound of Formula (1-1i) or a stereoisomer thereof with a reducing system in a solvent to obtain the compound of Formula (1-1d):

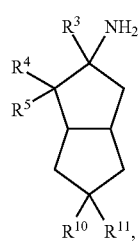

(1-1d)

wherein $R^3$ is $C_{1-4}$ alkyl; each of $R^4$ and $R^5$ is independently H, hydroxy, $C_{1-4}$ alkyl, cycloalkyl or heterocyclyl, and wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)$ NH—, alkoxy, aryloxy, heterocyclyl, carboxy and —C(=O) O—$C_{1-4}$ alkyl, or $R^3$ is H; $R^4$ and $R^5$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, cycloalkyl, heterocyclyl, aryl, heteroaryl, —$(CH_2)_r$-aryl, —$(CH_2)_r$O-aryl, —$(CH_2)_r$-heteroaryl, —$(CH_2)_r$O-heteroaryl, alkenyl, alkynyl, cyano, —$OR^{14}$, —$(CH_2)_pC(=O)OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)$ $OR^{14}$, —$OC(=O)NR^{14}R^{15}$ or —$NR^{14}R^{15}$, and wherein each of the $C_{1-6}$ alkyl, cycloalkyl, heterocyclyl, aryl, heteroaryl, —$(CH_2)_r$-aryl, —$(CH_2)_r$O-aryl, —$(CH_2)_r$-heteroaryl, —$(CH_2)_r$O-heteroaryl, alkenyl and alkynyl is optionally substituted with one or more substituents independently selected from H, $C_{1-6}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —C(=O)
O—C$_{1-4}$ alkyl, halogen and —NR$^{12}$R$^{13}$, or R$^{10}$ and R$^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, R$^{14}$C(=O)NH—, R$^{14}$R$^{15}$NC(=O)—, cyano, aminoalkyl, hydroxyalkyl, heterocyclyl, trifluoromethyl, carboxy, —C(=O)O—C$_{1-4}$ alkyl and —NR$^{12}$R$^{13}$;

wherein each R$^{12}$, R$^{13}$, R$^{14}$ and R$^{15}$ is independently H, C$_{1-6}$ alkyl, —(CH$_2$)$_p$—C$_{3-6}$ cycloalkyl, aryl, heteroaryl or heterocyclyl, and wherein each of the C$_{1-6}$ alkyl, —(CH$_2$)$_p$—C$_{3-6}$ cycloalkyl, aryl, heteroaryl and heterocyclyl is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, R$^{14}$C(O)NH—, R$^{14}$R$^{15}$NC(=O)—, cyano, aminoalkyl, hydroxyalkyl, heterocyclyl, heterocycloalkoxy, trifluoromethyl, carboxy, —C(=O)O—C$_{1-4}$ alkyl and —NR$^{12'}$R$^{13'}$, or R$^{12}$ and R$^{13}$, together with the nitrogen atom to which they are attached, form 3-8 membered heterocyclic ring, and R$^{14}$ and R$^{15}$, together with the nitrogen atom to which they are attached, form 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —C(=O)O—C$_{1-4}$ alkyl;

wherein each of R$^{12'}$ and R$^{13'}$ is independently H, C$_{1-4}$ alkyl, cycloalkyl, heterocyclyl, aryl or heteroaryl;

wherein r is 1, 2, 3 or 4;

wherein p is 0, 1, 2, 3 or 4; and wherein X is Cl, Br or I.

In some embodiments, the halohydrocarbon solvent is methyl chloride, dichloromethane, trichloromethane, tetrachloromethane, tribromethane, trichloroethylene, tetrachloroethylene, 1,1,1,2-tetrachloroethane, 1,1,1-trichloro ethane, 1,1,2,2-tetrachloroethane, 1,1,2-trichloroethane, 1,1-dichloro-1-fluoro ethane, 1,2,3-trichloropropane or 1,2-dichloroethane;

wherein the reducing system is hydrogen with a platinum on activated carbon catalyst, a sodium borohydride-copper sulfate system, lithium aluminium hydride, sodium borohydride or a combination thereof;

wherein the reducing agent is hydrogen, sodium borohydride, lithium aluminium, tri-tert-butoxyaluminum hydride or a combination thereof;

wherein the polar solvent is water, formamide, dimethyl sulfoxide, acetonitrile, N,N-dimethylformamide, methanol, ethanol, isopropanol or a combination thereof; and wherein the acid is sulfuric acid, hydrochloric acid, nitric acid, phosphoric acid, formic acid, acetic acid, trifluoroacetic acid, methyl sulfonic acid, benzenesulfonic acid, p-toluene sulfonic acid, 4-nitro benzoic acid or a combination thereof In some embodiments, provided herein is a process for preparing the compound of Formula (1-1d), further comprising the steps of:

(a) condensing the compound of formula (1-1i) with an aromatic acid in the presence of triphenylphosphine and diethyl azodicarboxylate to give an ester; and (b) hydrolyzing the ester in the presence of a base in a polar solvent to give a stereoisomer of the compound of formula (1-1i).

In other embodiments, the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the aromatic acid is benzoic acid, p-nitrobenzoic acid, 4-methoxybenzoic acid or 4-methylbenzoic acid; and wherein the polar solvent is water, formamide, dimethyl sulfoxide, acetonitrile, N,N-dimethylformamide, methanol, ethanol, isopropanol or a combination thereof.

In other embodiments, provided herein is a process for preparing the compound of Formula (1-1d), further comprising the steps of:

(a) reacting the compound of formula (1-1i) or a stereoisomer thereof with haloalkane, acyl halide or anhydride in the presence of a base to give a compound of formula (1-1c):

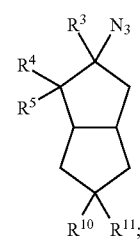

(1-1c)

and (b) reducing the compound of formula (1-1c) in a solvent to obtain the compound of formula (1-1d):

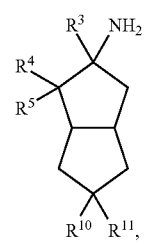

(1-1d)

wherein the solvent is a nonpolar solvent, a weak polar solvent or a polar solvent.

In other embodiments, the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the acyl halide is acetylchloride, propionyl chloride, methylsulfonyl chloride or paratoluensulfonyl chloride; the haloalkane is fluoromethane, chloroethane, bromoethane, iodomethane, iodoethane, chlorocyclopropane or (bromomethyl)cyclopropane;

wherein the anhydride is acetic anhydride, propionic anhydride, acetic formic anhydride, acetic benzoic anhydride or maleic anhydride; and wherein the polar solvent is water, formamide, dimethyl sulfoxide, acetonitrile, N,N-dimethylformamide, methanol, ethanol, isopropanol or a combination thereof.

In other aspect, provided herein is a process for preparing the compound of Formula (1-1d), further comprising the steps of:

(a) reacting a compound of formula (1-1a) with diethyl ethanedioate in the presence of a base in a polar solvent to give a compound of formula (1-1j):

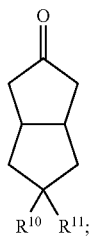

(1-1a)

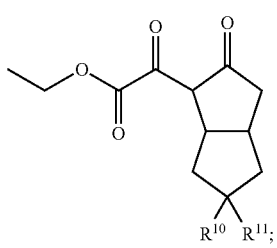

(1-1j)

(b) reacting the compound of formula (1-1j) with formaldehyde in the presence of a base in a polar solvent to give a compound of formula (1-1k):

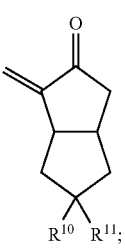

(1-1k)

(c) reacting the compound of formula (1-1k) with trimethylsulfoxonium iodide in the presence of a base in a polar solvent to give a compound of formula (1-1l):

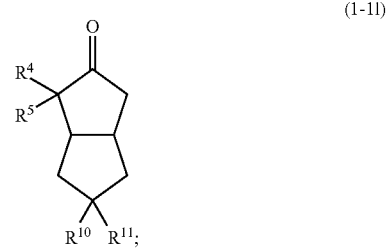

(1-1l)

(d) condensing the compound of formula (1-1l) with hydroxylamine hydrochloride in the presence of a base to give a compound of formula (1-1m):

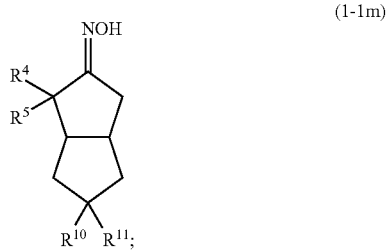

(1-1m)

and (e) reducing the compound of formula (1-1m) with a reducing agent to give the compound of formula (1-1d):

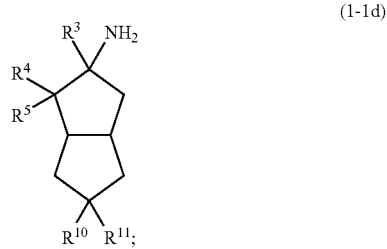

(1-1d)

wherein $R^3$ is $C_{1-4}$ alkyl; each of $R^4$ and $R^5$ is independently H, hydroxy, $C_{1-4}$ alkyl, cycloalkyl or heterocyclyl, and wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)$NH—, alkoxy, aryloxy, heterocyclyl, carboxy and —C(=O)O—$C_{1-4}$ alkyl, or $R^3$ is H; $R^4$ and $R^5$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, cycloalkyl, heterocyclyl, aryl, heteroaryl, —$(CH_2)_r$-aryl, —$(CH_2)_r$O-aryl, —$(CH_2)_r$-heteroaryl, —$(CH_2)_r$O-heteroaryl, alkenyl, alkynyl, cyano, —$OR^{14}$, —$(CH_2)_pC(=O)OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$, —OC or —$NR^{14}R^{15}$; wherein each of the $C_{1-6}$ alkyl, cycloalkyl, heterocyclyl, aryl, heteroaryl, —$(CH_2)_r$-aryl, —$(CH_2)_r$O-aryl, —$(CH_2)_r$-heteroaryl, —$(CH_2)_r$O-heteroaryl, alkenyl and alkynyl is optionally substituted with one or more substituents independently selected from H, $C_{1-6}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —$C(=O)O$—$C_{1-4}$ alkyl, halogen and —$NR^{12}R^{13}$, or $R^{10}$ and $R^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH$—, $R^{14}R^{15}NC(=O)$—, cyano, aminoalkyl, hydroxyalkyl, heterocyclyl, trifluoromethyl, carboxy, —$C(=O)O$—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —$(CH_2)_p$—$C_{3-6}$ cycloalkyl, aryl, heteroaryl or heterocyclyl, and wherein each of the $C_{1-6}$ alkyl, —$(CH_2)_p$—$C_{3-6}$ cycloalkyl, aryl, heteroaryl and heterocyclyl is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH$—, $R^{14}R^{15}NC(=O)$—, cyano, aminoalkyl, hydroxyalkyl, heterocyclyl, heterocycloalkoxy, trifluoromethyl, carboxy, —$C(=O)O$—$C_{1-4}$ alkyl and —$NR^{12'}R^{13'}$, or $R^{12}$ and $R^{13}$, together with the nitrogen atom to which they are attached, form a 3-8 membered heterocyclic ring, and $R^{14}$ and $R^{15}$, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —$C(=O)O$—$C_{1-4}$ alkyl;

wherein each of $R^{12'}$ and $R^{13'}$ is independently H, $C_{1-4}$ alkyl, cycloalkyl, heterocyclyl, aryl or heteroaryl;

wherein r is 1, 2, 3 or 4; and wherein p is 0, 1, 2, 3 or 4.

In some embodiments, the reducing system is hydrogen with a platinum on activated carbon catalyst, a sodium borohydride-copper sulfate system, lithium aluminium hydride, sodium borohydride or a combination thereof;

wherein the reducing agent is hydrogen, sodium borohydride, lithium aluminium, tri-tert-butoxyaluminum hydride or a combination thereof; wherein the polar solvent is water, formamide, dimethyl sulfoxide, acetonitrile, N,N-dimethylformamide, methanol, ethanol, isopropanol or a combination thereof; and wherein the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof.

In other aspect, provided herein is a process for preparing the compound of Formula (1-1d), further comprising the steps of:

(a) oxidizing a compound of formula (1-1i) with an oxidizing agent in a halohydrocarbon solvent to give a compound of formula (1-1o):

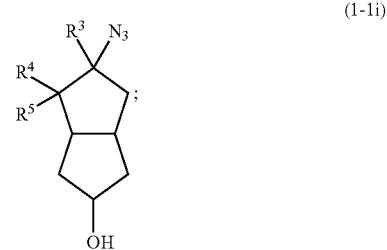

(1-1i)

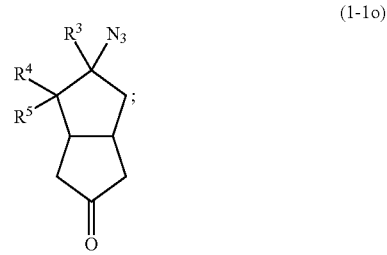

(1-1o)

(b) reducing the compound of formula (1-1o) with a reducing agent to give a compound of formula (1-1p):

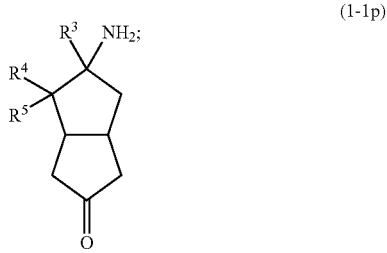

(1-1p)

and (c) reacting the compound of formula (1-1p) with trimethylsulfoxonium iodide in the presence of a base to give the compound of formula (1-1d):

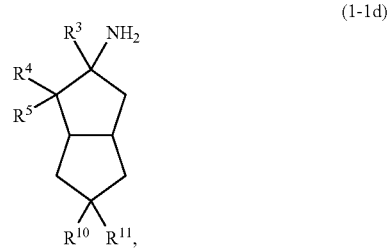

(1-1d)

wherein $R^3$ is $C_{1-4}$ alkyl; each of $R^4$ and $R^5$ is independently H, hydroxy, $C_{1-4}$ alkyl, cycloalkyl or heterocyclyl, and wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)NH$—, alkoxy, aryloxy, heterocyclyl, carboxy and —C(=O)O—$C_{1-4}$ alkyl, or $R^3$ is H; $R^4$ and $R^5$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —C(=O)O—$C_{1-4}$ alkyl, F, Cl, Br, I and —$NR^{12}R^{13}$;

wherein each of $R^{10}$ and $R^{11}$ is independently H, hydroxy, $C_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_r$O-heteroaryl, alkenyl, alkynyl, cyano, —OR$^{14}$, —(CH$_2$)$_p$C(=O)OR$^{14}$, —(CH$_2$)$_p$OC(=O)R$^{14}$, —(CH$_2$)$_p$C(=O)NR$^{14}$R$^{15}$, —(CH$_2$)$_p$OC(=O)NR$^{14}$R$^{15}$, —C(=O)R$^{14}$, —N(R$^{14}$)C(=O)R$^{15}$, —N(R$^{15}$)C(=O)OR$^{15}$, —OC(=O)OR$^{14}$, —OC(=O)NR$^{14}$R$^{15}$, or —NR$^{14}$R$^{15}$, and wherein each of the $C_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_r$O-heteroaryl, alkenyl and alkynyl is optionally substituted with one or more substituents independently selected from H, $C_{1-6}$ alkyl, aryl, heteroaryl, haloalkyl, haloalkoxy, hydroxy, amino, alkylamino, $R^{14}C(=O)NH$—, $R^{14}R^{15}NC(=O)$—, cyano, alkoxy, aryloxy, aminoalkyl, hydroxyalkyl, heterocyclyl, carboxy, —C(=O)O—$C_{1-4}$ alkyl, halogen and —$NR^{12}R^{13}$, or $R^{10}$ and $R^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH$—, $R^{14}R^{15}NC(=O)$—, cyano, aminoalkyl, hydroxyalkyl, heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —(CH$_2$)$_p$—$C_{3-6}$ cycloalkyl, aryl, heteroaryl or heterocyclyl, and wherein each of the $C_{1-6}$ alkyl, —(CH$_2$)$_p$—$C_{3-6}$ cycloalkyl, aryl, heteroaryl and heterocyclyl is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH$—, $R^{14}R^{15}NC(=O)$—, cyano, aminoalkyl, hydroxyalkyl, heterocyclyl, heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which to which they are attached, form a 3-8 membered heterocyclic ring, and $R^{14}$ and $R^{15}$, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —C(=O)O—$C_{1-4}$ alkyl;

wherein each of $R^{12'}$ and $R^{13'}$ is independently $C_{1-4}$ alkyl, cycloalkyl, heterocyclyl, aryl or heteroaryl;

wherein r is 1, 2, 3 or 4;

wherein p is 0, 1, 2, 3 or 4; and wherein the solvent is a nonpolar solvent, a weak polar solvent or a polar solvent.

In some embodiments, the halohydrocarbon solvent is methyl chloride, dichloromethane, trichloromethane, tetrachloromethane, tribromethane, trichloroethylene, tetrachloroethylene, 1,1,1,2-tetrachloroethane, 1,1,1-trichloroethane, 1,1,2,2-tetrachloroethane, 1,1,2-trichloroethane, 1,1-dichloro-1-fluoroethane, 1,2,3-trichloropropane or 1,2-dichloroethane;

wherein the reducing system is hydrogen with a platinum on activated carbon catalyst, a sodium borohydride-copper sulfate system, lithium aluminium hydride, sodium borohydride or a combination thereof;

wherein the reducing agent is hydrogen, sodium borohydride, lithium aluminium, tri-tert-butoxyaluminum hydride or a combination thereof;

wherein the polar solvent is water, formamide, dimethyl sulfoxide, acetonitrile, N,N-dimethylformamide, methanol, ethanol, isopropanol or a combination thereof;

wherein the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof; and wherein the oxidizing agent is Dess-Martin periodinane, 2-iodoxybenzoic acid, oxalyl chloride, chromium trioxide-pyridine complex, sodium hypochlorite, pyridine sulfur trioxide, sodium periodate, hydrogen peroxide, 2,2,6,6-tetramethylpiperidinooxy, potassium permanganate or a combination thereof.

In other aspect, provided herein is a process for preparing the compound of Formula (1-1d), further comprising the steps of:

(a) reducing a compound of formula (1-1i) to give a compound of formula (1-1q):

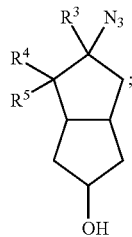
(1-1i)

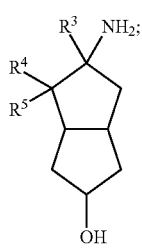
(1-1q)

(b) reacting the compound of formula (1-1q) with di-tert-butyl dicarbonate in the presence of a base to give a compound of formula (1-1r):

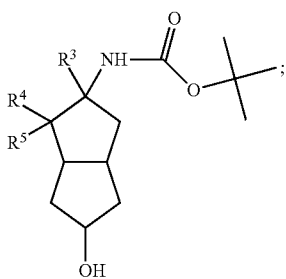
(1-1r)

(c) oxidizing the compound of formula (1-1r) with an oxidizing agent to give a compound of formula (1-1s):

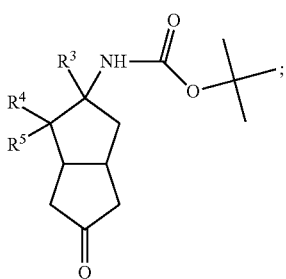
(1-1s)

(d) reacting the compound of formula (1-1s) with p-tosyl isocyanate in the presence of a base to give a compound of formula (1-1t):

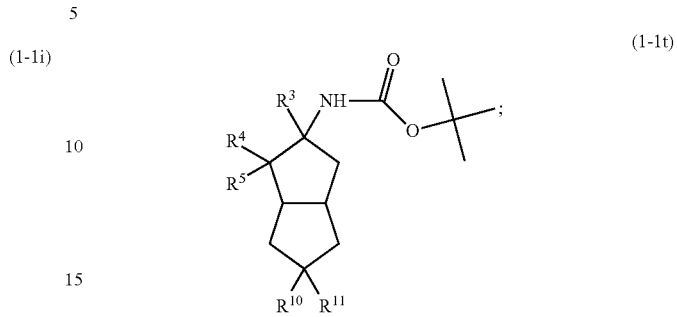
(1-1t)

and (e) reducing the compound of formula (1-1t) with a reducing system in a polar solvent to give the compound of formula (1-1d):

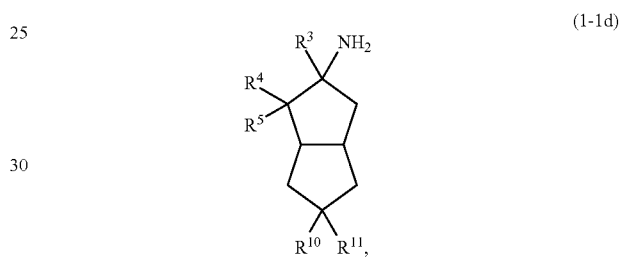
(1-1d)

wherein $R^3$ is $C_{1-4}$ alkyl; each of $R^4$ and $R^5$ is independently H, hydroxy, $C_{1-4}$ alkyl, cycloalkyl or heterocyclyl, wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)NH-$, alkoxy, aryloxy, heterocyclyl, carboxy and $-C(=O)O-C_{1-4}$ alkyl, or $R^3$ is H; $R^4$ and $R^5$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, aryl, heteroaryl, haloalkyl, haloalkoxy, hydroxy, amino, alkylamino, $R^{14}C(=O)NH-$, $R^{14}R^{15}NC(=O)-$, cyano, alkoxy, aryloxy, aminoalkyl, hydroxyalkyl, heterocyclyl, carboxy, $-C(=O)O-C_{1-4}$ alkyl, F, Cl, Br, I and $-NR^{12}R^{13}$;

wherein each of $R^{10}$ and $R^{11}$ is independently H, hydroxy, $C_{1-6}$ alkyl, cycloalkyl, heterocyclyl, aryl, heteroaryl, $-(CH_2)_r$-aryl, $-(CH_2)_r$O-aryl, $-(CH_2)_r$-heteroaryl, $-(CH_2)_r$O-heteroaryl, alkenyl, alkynyl, cyano, $-OR^{14}$, $-(CH_2)_pC(=O)OR^{14}$, $-(CH_2)_pOC(=O)R^{14}$, $-(CH_2)_pC(=O)NR^{14}R^{15}$, $-(CH_2)_pOC(=O)NR^{14}R^{15}$, $-C(=O)R^{14}$, $-N(R^{14})C(=O)R^{15}$, $-N(R^{15})C(=O)OR^{15}$, $-OC(=O)OR^{14}$, $-OC(=O)NR^{14}R^{15}$ or $-NR^{14}R^{15}$, and wherein each of the $C_{1-6}$ alkyl, cycloalkyl, heterocyclyl, aryl, heteroaryl, $-(CH_2)_r$-aryl, $-(CH_2)_r$O-aryl, $-(CH_2)_r$-heteroaryl, $-(CH_2)_r$O-heteroaryl, alkenyl and alkynyl is optionally substituted with one or more substituents independently selected from H, $C_{1-6}$ alkyl, aryl, heteroaryl, haloalkyl, haloalkoxy, hydroxy, amino, alkylamino, $R^{14}C(=O)NH-$, $R^{14}R^{15}NC(=O)-$, cyano, alkoxy, aryloxy, aminoalkyl, hydroxyalkyl, heterocyclyl, carboxy, $-C(=O)O-C_{1-4}$ alkyl, halogen and $-NR^{12}R^{13}$, or $R^{10}$ and $R^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH-$, $R^{14}R^{15}NC(=O)-$, cyano, aminoalkyl, hydroxyalkyl, heterocyclyl, trifluoromethyl, carboxy, $-C(=O)O-C_{1-4}$ alkyl and $-NR^{12}R^{13}$;

wherein each $R^{12}$, $R^{13}$, $R^{14}$ and $R^{15}$ is independently H, $C_{1-6}$ alkyl, $-(CH_2)_p-C_{3-6}$ cycloalkyl, aryl, heteroaryl or heterocyclyl, and wherein each of the $C_{1-6}$ alkyl, $-(CH_2)_p-C_{3-6}$ cycloalkyl, aryl, heteroaryl and heterocyclyl is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH-$, $R^{14}R^{15}NC(=O)-$, cyano, aminoalkyl, hydroxyalkyl, heterocyclyl, heterocycloalkoxy, trifluoromethyl, carboxy, $-C(=O)O-C_{1-4}$ alkyl and $-NR^{12'}R^{13'}$, or $R^{12}$ and $R^{13}$, together with the nitrogen atom to which they are attached, form a 3-8 membered heterocyclic ring, and $R^{14}$ and $R^{15}$, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and $-C(=O)O-C_{1-4}$ alkyl;

wherein each of $R^{12'}$ and $R^{13'}$ is independently H, $C_{1-4}$ alkyl, cycloalkyl, heterocyclyl, aryl or heteroaryl;

wherein r is 1, 2, 3 or 4; and wherein p is 0, 1, 2, 3 or 4.

In some embodiments, the reducing system is hydrogen with a platinum on activated carbon catalyst, a sodium borohydride-copper sulfate system, lithium aluminium hydride, sodium borohydride or a combination thereof;

wherein the polar solvent is water, formamide, dimethyl sulfoxide, acetonitrile, N,N-dimethylformamide, methanol, ethanol, isopropanol or a combination thereof;

wherein the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof; and wherein the oxidizing agent is Dess-Martin periodinane, 2-iodoxybenzoic acid, oxalyl chloride, chromium trioxide-pyridine complex, sodium hypochlorite, pyridine sulfur trioxide, sodium periodate, hydrogen peroxide, 2,2,6,6-tetramethylpiperidinooxy, potassium permanganate or a combination thereof.

In other aspect, provided herein is a pharmaceutical composition comprising the compound described herein and a pharmaceutically acceptable carrier, excipient, diluent, adjuvant, vehicle or a combination thereof In some embodiments, the pharmaceutical composition disclosed herein further comprises an additional therapeutic agent, wherein the additional therapeutic agent is an anti-diabetic agent other than a DPP-IV inhibitor, an antihyperglycemic agent, an antiadipositas drug, an antihypertensive agent, an antiplatelet agent, an antiatherosclerotic drug, a lipid-lowering agent, an anti-inflammatory or a combination thereof.

In other embodiments, the anti-diabetic agent other than a DPP-IV inhibitor or an antihyperglycemic agent is a biguanide, a sulfonylurea, a glucosidase inhibitor, a PPAR agonist, an αP2 inhibitor, a PPARα/γ dual agonist, a SGLT-2 inhibitor, a nateglinide agent, insulin, a glucagon-like peptide-1(GLP-1) inhibitor, a PTP1B inhibitor, a glycogen phosphorylase inhibitor, a glucose-6-phosphatase inhibitor or a combination thereof.

In other embodiments, the lipid-lowering agent is an MTP inhibitor, an HMGCoA reductase inhibitor, a squalene synthase inhibitor, a fibric acid derivative, an ACAT inhibitor, a lipoxygenase inhibitor, a cholesterol absorption inhibitor, an ileal Na(+)/bile acid cotransporter inhibitor, an upregulator of LDL receptor activity, niacin or a derivative thereof, a bile acid sequestrant or a combination thereof.

In other embodiments, the lipid-lowering agent is pravastatin, simvastatin, atorvastatin, fluvastatin, cerivastatin, atavastatin, rosuvastatin or a combination thereof In other aspect, provided herein is use of the compound or the pharmaceutical composition disclosed herein in the manufacture of a DPP-IV inhibitor.

In other aspect, provided herein is use of the compound or a stereoisomer, a geometric isomer, a tautomer, a racemate, an N-oxide, a hydrate, a solvate, a metabolite, a pharmaceutically acceptable salt or a prodrug thereof or the pharmaceutical composition disclosed herein in the manufacture of a medicament for preventing or treating a disease, lessening a disease symptoms, delaying the progression or onset of a disease or increasing HDL level, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis, hypertension, acute anemia or neutropenia.

In other aspect, provided herein is a method for inhibiting the activity of DPP-IV, comprising administering to the patient in need thereof a therapeutically effective amount of the compound or the pharmaceutical composition disclosed herein.

In other aspect, provided herein is a method for preventing or treating a disease, lessening a disease symptoms, delaying the progression or onset of a disease or increasing HDL level, comprising administering to the patient in need thereof a therapeutically effective amount of the compound or the pharmaceutical composition disclosed herein, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis, hypertension, acute anemia or neutropenia.

In other aspect, provided herein is the compound or the pharmaceutical composition disclosed herein for use in inhibiting the activity of DPP-IV.

In other aspect, provided herein is the compound or the pharmaceutical composition disclosed herein for use in preventing or treating a disease, lessening a disease symptoms, delaying the progression or onset of a disease or increasing HDL level, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis, hypertension, acute anemia or neutropenia.

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Unless otherwise stated, the following terms used in the specification and claims have the meanings described below.

"Halogen" refers to F, Cl, Br or I. In some embodiments, "halogen" refers to F, Cl or Br.

"$C_{1-n}$ alkyl" refers to a saturated linear or branched chain hydrocarbon group including 1 to n carbon atoms. In some embodiments, n is an integer from 1 to 20. In other embodiments, n is an integer from 1 to 10, especially an integer from 1 to 4. Some non-limiting examples of the $C_{1-n}$ alkyl group include methyl, ethyl, propyl, 2-propyl, n-butyl, i-butyl, t-butyl, n-pentyl, 1-methyl-butyl, 2-methyl-butyl, 3-methyl-1-butyl, neopentyl, 3,3-dimethyl-propyl, n-hexyl and 2-methyl-pentyl, etc. The alkyl group containing 1 to 6 carbon atoms described herein is a lower alkyl. The $C_{1-n}$ alkyl group may be substituted or unsubstituted. When substituted, the $C_{1-n}$ alkyl group is substituted by one or more substituents independently selected from —F, —Cl, —Br, —I, hydroxy, cyano, amino, carboxy and —C(=O)O—$C_{1-4}$ alkyl. The alkyl group of all terms has the same definition as the $C_{1-n}$ alkyl group described herein.

"Haloalkyl" refers to an alkyl group substituted with one or more halogen atoms. Some non-limiting examples of the haloalkyl group include fluoromethyl, difluoromethyl, trifluoromethyl, perfluoroethyl, 1,1-dichloroethyl and 1,2-dichloropropyl, etc.

"Alkoxy" refers to $C_{1-n}$ alkyl-O—, the $C_{1-10}$ alkyl-O— group belongs to lower-alkoxy. Some non-limiting examples of the alkoxy group include methoxy, ethoxy, propoxy, isopropoxy, tert-butoxy and neopentyloxy, etc.

"Alkylamino" refers to an amino group substituted with one or two alkyl radicals. The alkylamino containing 1-10 carbon atoms is lower alkylamino group. Some non-limiting examples of the alkylamino radical include methylamino, ethylamino, n-propylamino, isopeopylamino, n-butylamino, n-pentylamino, N,N-dimethylamino, N,N-diethylamino, N-ethyl-N-methylamino and N-methyl-N-propypamino, etc.

"Alkylthio" refers to a divalent sulfur atom attached with a linear or branched $C_{1-10}$ alkyl group. In some embodiments, the alkylthio radical refers to lower $C_{1-3}$ alkylthio radicals. Some non-limiting examples of the alkylthio group include methylthio ($CH_3S$—).

"Alkylacyl" refers to $C_{1-n}$ alkylacyl. Some non-limiting examples of the alkylacyl group include formyl, acetyl, propionyl and butyryl, etc.

"Alkylaminocarbonyl" refers to an aminocarbonyl group substituted with one or two alkyl groups. Some non-limiting examples of the alkylaminocarbonyl group include methylaminocarbonyl, ethylaminocarbonyl, n-propylaminocarbonyl, isopropylaminocarbonyl, N,N-dimethylaminocarbonyl, N,N-diethylaminocarbonyl, N-ethyl-N-methylaminocarbonyl, N-methyl-N-propylaminocarbonyl and N-methyl-N-isopropylaminocarbonyl, etc.

"Alkoxycarbonyl" refers to an alkoxy-carbonyl group. Some non-limiting examples of the alkoxycarbonyl group include methoxycarbonyl, ethoxylcarbonyl, n-propoxycarbonyl, isopropoxycarbonyl and tert-butoxycarbonyl, etc.

"Hydroxyalkyl" refers to a linear or branched $C_{1-10}$ alkyl group substituted with one or more hydroxy groups. In some embodiments, the hydroxyalkyl refers to $C_{1-6}$ lower alkyl substituted with one or more hydroxy groups. Some non-limiting examples of the hydroxyalkyl group include hydroxymethyl, hydroxyethyl, hydroxypropyl, hydroxybutyl and hydroxyhexyl, etc.

"Aminoalkyl" refers to a linear or branched $C_{1-10}$ alkyl group substituted with one or more amino groups. In some embodiments, "aminoalkyl" refers to a $C_{1-6}$ lower alkyl group substituted with one or more amino groups. Some non-limiting examples of the aminoalkyl group include aminomethyl, aminoethyl, aminopropyl, aminobutyl and aminohexyl, etc.

"Haloalkoxy" refers to an alkoxy group substituted with one or more halogen atoms. Wherein the alkoxyl group is as defined herein. Some non-limiting examples of the haloalkoxy group include 2-trifluoro-ethoxy, trifluoromethoxy and 2-fluoro-ethoxy, etc.

"Alkenyl" refers to a linear or branched-chain monovalent hydrocarbon radical containing 2 to 10 carbon atoms that has at least one double bond. In some embodiments, the alkenyl group includes a linear or branched-chain monovalent hydrocarbon radical having 2 to 6 carbon atoms. In other embodiments, the alkenyl group includes a linear or branched-chain monovalent hydrocarbon radical having 2 to 4 carbon atoms. Some non-limiting examples of the alkenyl group include ethenyl or vinyl, allyl, 1-butenyl, 1-pentenyl, cis-2-butenyl, trans-2-butenyl, isobutenyl, 3-methyl-1-butenyl and cyclopentenyl, etc. The alkenyl group may be substituted or unsubstituted, when substituted, the alkenyl group is substituted by one or more groups substituents independently selected from —F, —Cl, —Br, —I, lower alkyl, hydroxy, cyano, amino, carboxy and —C(=O)O$C_{1-4}$ alkyl, etc.

"Alkynyl" refers to a linear or branched-chain monovalent hydrocarbon radical containing 2 to 10 carbon atoms that has at least one triple bond. In some embodiments, the alkynyl group is a linear or branched-chain monovalent hydrocarbon radical having 2 to 6 carbon atoms. In other embodiments, the alkynyl group is a linear or branched-chain monovalent hydrocarbon radical having 2 to 4 carbon atoms. Some non-limiting examples of the alkynyl group include ethynyl, propynyl, 1-butynyl, 2-butynyl, 1-pentynyl, 2-pentynyl, 3-methyl-1-butynyl, 1-hexynyl, 1-heptynyl and 1-octynyl, etc. The alkynyl group may be substituted or unsubstituted, when substituted, the alkynyl group is substituted by one or more substituents independently selected from —F, —Cl, —Br, —I, lower alkyl, hydroxy, cyano, amino, carboxy and —C(=O)O$C_{1-4}$ alkyl, etc.

"Cycloalkyl" refers to a saturated or partially saturated monocyclic or polycyclic (fused, bridged and/or spiro ring), non-aromatic carbocycle group and has 3 to n carbon atoms. In some embodiments, n is an integer from 3 to 30. In other embodiments, n is an integer from 3 to 15, preferably n is an integer from 3 to 10. Some non-limiting examples of the cycloalkyl group include cyclopropyl, cyclobutyl, cyclopentyl, cycloheptyl, cyclopentenyl, cyclohexenyl, cyclohexadienyl, cycloheptatrienyl, norbornyl, norpinanyl, norcaryl, adamantly, bicyclo[3.2.1]octyl and spiro[4.5]decyl, etc. The cycloalkyl group may be substituted or unsubstituted, when substituted, the cycloalkyl group is substituted by one or more substituents independently selected from hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc. In some embodiments, the cycloalkyl group is unsubstituted saturated monocycle.

"Cycloalkyloxy" refers to an optionally substituted cycloalkyl, as defined herein, attached to an oxygen atom, wherein the oxygen atom serves as the attaching point to the rest of the molecule. Some non-limiting examples of the cycloalkyloxy group include cyclopropyloxy, cyclopentyloxy, cyclohexyloxy and hydroxy-substituted cyclopropyloxy, etc.

"Heterocyclyl" refers to a saturated or partially saturated monocyclic or polycyclic (fused, bridged and/or spiro ring), non-aromatic carbocycle group containing 3 to n carbon atoms and having one or more heteroatoms independently selected from oxygen, sulfur, selenium, nitrogen, phosphorus and silicon, wherein n is an integer from 3 to 20. In some embodiments, n is an integer from 3 to 15. In other embodiments, n is an integer from 3 to 10. In other embodiments, n is an integer from 3 to 6. The heterocyclyl may contain a carbon radical or heteroatom radical. Some non-limiting examples of the heterocyclicalkyl group include oxetanyl, tetrahydrofuranyl, pyranyl, pyrrolidinyl, imidazolidinyl, tetrahydrothiophenyl, piperidinyl, piperazinyl, morpholinyl, thiomorpholinyl, imidazolinyl, oxazolidinyl, pyrazolidinyl, pyrrolinyl and oxo-2(1H)-pyridyl, etc. Heterocyclicalkyl is optionally substituted with one or more substituents. Some non-limiting examples of the substituent include hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc. In some embodiments, the heterocyclicalkyl group is unsubstituted saturated monocyclyl.

"Heterocyclylalkoxy" refers to a heterocyclic-substituted alkoxy radical wherein oxygen atom serves as the attaching point to the rest of the molecule. Some non-limiting examples of the heterocyclylalkoxy group include morpholin-4-ylethoxy and piperazin-4-ylethoxy, etc.

"Heterocycle" refers to a chemical compound derived from a ring having one or more heteroatoms, wherein the ring is completely saturated or contains one or more units of unsaturation, but not aromatic. Some non-limiting examples of the heterocycle group include pyrrolidine, tetrahydrofuran, dihydrofuran, tetrahydrothiophene, tetrahydropyrane, dihydropyran, tetrahydrothiopyran, piperidine, morpholine, thiomorpholine, thioxane, piperazine, homopiperazine, azetidine, oxetane, thietane, homopiperdine, epoxypropane, azepane, oxepane, pentathiepane, oxazepine, diazepine, thiazepine, 2-pyrroline, 3-pyrroline, indoline, 2H-pyrane, 4H-pyrane, dioxolane, 1,3-dioxolane, pyrazoline, dithiane, ditholane, dihydrothiophene, pyrazolidinylimidazoline, imidazolidine, 1,2,3,4-tetrahydroisoquinoline, 3-azabicyclo[3,1,0]hexane, 3-azabicyclo[4,1,0]heptane, azabicyclo[2,2,2]hexane and 3H-indolylquinolizidine, etc. Hydrogen atom(s) of the ring is optionally independently replaced by one or more substituents described herein, wherein some non-limiting examples of the substituent include hydroxy, amino, halogen, cyano, aryl, heteroaryl, alkoxy, alkyl, alkenyl, alkynyl, heterocyclyl, mercapto, nitro and aryloxy, etc.

"Acyl halide" is a chemical compound derived from an oxoacid by replacing a hydroxy group with a halide group. If the acid is a carboxylic acid, the compound contains a —COX functional group, which consists of a carbonyl group singly bonded to a halogen atom. The general formula for such an acyl halide can be written as RCOX, where R may be, for example, an alkyl group, CO is the carbonyl group, and X represents a halogen such as chlorine. Acyl chlorides can be divided into acyl fluoride, acyl chlorides, acyl bromide and acyl iodide (transiently). The hydroxy group of a sulfonic acid may also be replaced by a halogen to produce the corresponding sulfonyl halide. In practical terms, this is almost always chloride to give the sulfonyl chloride. Some non-limiting examples of the acyl halide group include acetylchloride, propionyl chloride, methylsulfonyl chloride and paratoluensulfonyl chloride, etc.

"Haloalkane" is an organic compound derived from an alkane by replacing one or more hydrogen atoms with halogen atoms. The general formula for such a haloalkane can be written as R—X, where R is an alkyl group, and X can be regarded as functional group of haloalkane, which includes F, Cl, Br and I. Some non-limiting examples of the haloalkane group include fluoromethane, difluoromethane, perfluoroethane, dichloromethane, 1,2-dichloro ethane, 1,1-dichloro ethane, 1,2-dichloropropane, trichloromethane, chloroethane, bromoethane, iodomethane, iodoethane, cyclopropyl chloride and cyclopropyl bromomethane, etc.

"Anhydride" is an organic compound that has two acyl groups bound to the same oxygen atom. The acyl groups are derived from the same carboxylic acid, the formula of the anhydride being $(RC(O))_2O$. Symmetrical acid anhydrides of this type are named by replacing the word acid in the name of the parent carboxylic acid by the word anhydride. Thus, $(CH_3CO)_2O$ is called acetic anhydride. Mixed (or unsymmetrical) acid anhydrides are named by listing the names of the corresponding carboxylic acids followed by the anhydride ending, such as acetic formic anhydride. Some non-limiting examples of the anhydride include acetic anhydride, propionic anhydride, acetic formic anhydride, acetic benzoic anhydride and maleic anhydride, etc.

"Aromatic acid" refers to a compound that contains a COOH group bonded to a carbon atom of an aromatic ring or a side chain of an aromatic ring. Some non-limiting examples of the aromatic acid include benzoic acid, paratoluic acid, phenylacetic acid, p-methoxybenzoic acid, pyridine-2,3-dicarboxylic acid, naphthalene-2,6-dicarboxylic acid, furan-2-carboxylic acid and 2-(4-aminophenyl)acetic acid, etc.

"Aryl" refers to a cyclic hydrocarbon system of a monocyclic or multicyclic aromatic ring fused (sharing an adjacent pair of atoms between two rings) and/or connected (connecting directly with another ring by a single bone or a double bone) together, and also refers to a monocyclic aromatic hydrocarbon or multicyclic aromatic system having monocyclic aromatic ring or multicyclic hydrocarbon ring fused to one or more cycloalkyl and/or heterocyclicalkyl. The term "aryl" may be used interchangeably with the term "aryl ring". In some embodiments, the aryl group is a monocyclic aryl ring, 8 to 16 carbon atoms multicyclic aryl ring, benzocycloalkyl or benzoheterocyclicalkyl. Some non-limiting examples of the aryl group include phenyl, 1-naphthyl, 2-naphthyl, anthryl, phenanthrylphenmethyl, p-aminophenyl, 2-aminophenyl, phenolic group, p-carboxyphenyl, 2-carboxyphenyl, p-trifluoromethylphenyl, o-nitrophenyl, m-nitrophenyl, p-nitrophenyl, o-cyanophenyl, m-cyanophenyl, p-cyanophenyl, 2,6-dinitrophenyl, benzodioxanyl, benzodioxolyl, chromanyl and benzodihydroindolyl, etc. The aryl group is optionally substituted with one or more substituents independently selected from hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc.

"Aryloxy" refers to an optionally substituted aryl radical, as defined herein, attached to an oxygen atom, wherein the oxygen atom serves as the attaching point to the rest of the molecule. Wherein the aryl radical is as defined herein. Some non-limiting examples of the aryloxy group include phenyloxy, methylphenyloxy and p-ethylphenyloxy, etc.

"Heteroaryl" refers to an aryl group having one or more heteroatoms. The heteroatom is oxygen, sulfur, selenium, nitrogen, phosphorus or silicon. Some non-limiting examples of the heteroaryl group include furanyl, thiophenyl, pyrrolyl, pyridinyl, quinolinyl, thiazolyl, N-alkylpyrrolyl, pyrimidinyl, pyrazinyl, indolyl, imidazolyl, tetrazolyl, 2-formylfuranyl, 3-formylpyridinyl, 4-methylimidazolyl, 5-methylthiazolyl, 2,5-dimethylfuranyl, 3-acetoxyindolyl, benzopyranyl, benzopyrrolyl, benzofuranyl etc. Heteroaryl is optionally substituted with one or more substituents, wherein the substituents include, but are not limited to, hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc.

"Heteroaryloxy" refers to an optionally substituted heteroaryl radical, as defined herein, attached to an oxygen atom, wherein the oxygen atom serves as the attaching point to the rest of the molecule. Some non-limiting examples of the heteroaryloxy group include pyrid-2-yloxy, thiazol-2-yloxy, imidazol-2-yloxy and pyrimidin-2-yloxy, etc.

"Aralkyl" refers to an alkyl group containing one or more aryl groups. Some non-limiting examples of the aralkyl group include benzyl, phenethyl and phenylpropyl, etc.

"Heteroaralkyl" refers to an alkyl group containing one or more heteroarylgroups, wherein the heteroaryl and the alkyl are as defined herein. Some non-limiting examples of the heteroaralkyl group include pyrid-2-yl-ethyl, thiazol-2-yl-methyl, imidazol-2-yl-ethyl and pyrimidin-2-yl-propyl, etc.

"Spiro ring" or "spiro cycle" refers to a special ring formed by two adjacent rings sharing one common atom. Spiro ring can be a carbon ring or a heterocyclic ring containing one or more heteroatoms. The heteroatom is oxygen, nitrogen, sulfur or phosphorus. In some embodiments, the spiro ring contains 5 to 30 atoms. Some non-limiting examples of the spiro ring include spiro[2.4]heptane, spiro[4.5]decane, 1-methylspiro[4.5]decane, bicyclicspiro[5.2.5.2]cetane, tricyclicspiro[5.2.2.5.2.2]heneicosane, 2,6-diazaspiro[4.5]decane, diazaspiro[5.5]undecane and diazaspiro[5.6]dodecane, etc. The spiro ring is optionally substituted with one or more substituents, wherein the substituents include, but not limited to, hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc.

"Fused ring", "fused cycle" or "fused bicyclyl" refers to a special ring formed by two adjacent rings sharing two common adjacent atoms, and it is an unsaturated or saturated fused cyclic system that is not aromatic. Such ring may be a carbon ring and also a heterocyclic ring containing one or more heteroatoms independently selected from oxygen, nitrogen, sulfur and phosphorus. Such system may contain isolated or conjugated unsaturation bonds. The core structure of the system does not contain aromatic or heteroaromatic ring (but may be substituted with one or more aromatic rings). Each ring of the fused bicyclic ring may be carbocyclic or heterocycloaliphatic ring. Some non-limiting examples of the fused bicyclic ring system include hexahydro-furo[3,2-b]furan, 2,3,3a,4,7,7a-hexahydro-1H-indene, 7-azabicyclo[2.2.1]heptane, fused bicyclo[3.3.0]octane, fused bicyclo[3.1.0]hexane and 1,2,3,4,4a,5,8,8a-octahydro-naphthalene. The fused bicyclyl defined herein may be substituted or unsubstituted, wherein the substituents include, but are not limited to, hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc.

"Bridged ring" or "bridged cyclyl" refers to a special ring formed by two adjacent rings sharing two common nonadjacent atoms. Such ring may be a carbon ring and also a heterocyclic ring containing one or more heteroatoms independently selected from oxygen, nitrogen, sulfur and phosphorus. In some embodiments, the bridged ring has 5 to 30 atoms. Some non-limiting examples of the bridged ring system include norbornane, norpinane, norcarane, adamantane, bicyclo[3.2.1]octane, (1S,4S)-2-oxa-5-azabicyclo[2.2.1]heptanes, 5,6-dimethylbicyclo[2.2.2]-2-octylene, 7H-7-azebicycle and 1,4-diazebicycle, etc. The bridged bicyclyl defined herein may be substituted or unsubstituted, wherein the substituents include, but are not limited to, hydroxy, amino, halogen, carboxy, cyano, aryl, heteroaryl, alkoxy, alkylthio, alkyl, cycloalkyl, alkenyl, alkynyl, heterocyclyl, heterocycloalkyl, mercapto, nitro, aryloxy and heteroaryloxy, etc.

"Mercapto" refers to —SH.
"Nitro" refers to —NO$_2$.
"Hydroxy" refers to —OH.
"Amino" refers to —NH$_2$.
"Cyano" refers to —CN.
"Carboxy" refers to —C(=O)OH.
"TBS" refers to tert-butyldimethylsilyl.
"TMS" refers to trimethylsilyl.
"Ts" refers to p-tosyl.
"Bn" refers to benzyl.
"PMB" refers to p-methoxybenzyl.
"Ac" refers to acetyl.
"Boc" refers to tert-butyloxycarboryl.

"Grignard reaction" refers to the addition of a Grignard reagent to a polar double bond, such as the addition of a Grignard reagent to a carbonyl group is often used in introduction of a long carbon chain or synthesis of alcohol compounds, which proceeds through a nucleophilic addition of the Grignard reagent to a carbonyl compound (e.g., aldehyde, ketone or ester). Grignard reagents are hydrocarbyl magnesium halides (R-MgX, wherein X is halogen), which are useful nucleophilic reagents and were discovered by French Chemist Victor Grignard. Grignard reagents include methylmagnesium bromide, benzylmagnesium bromide, ethylmagnesium bromide, allylmagnesium bromide and ethylmagnesium chloride, etc.

A "pharmaceutical composition" refers to a mixture of one or more of the compounds described herein, or physiologically/pharmaceutically acceptable salts or prodrugs thereof, and other chemical components, such as physiologically/pharmaceutically acceptable carriers and excipients. The purpose of the pharmaceutical composition is to facilitate administration of a compound to an organism.

"Optional" or "optionally" means that the subsequently described event or circumstance may or may not occur, and that the description includes instances where the event or circumstance may or may not occur. For example, "heterocyclic group optionally substituted by an alkyl group" means that the alkyl may or may not be present, and the description includes situations where the heterocyclic group is substituted by an alkyl group and situations where the heterocyclic group is not substituted by the alkyl group.

The conditions, diseases and maladies collectively refer to as "Syndrome X" (also known as metabolic syndrome) which is described in detail in Johannsson, *J.* Clin. Endocrinol. Metab., 1997; 82, 727-734, which is incorporated herein by reference.

"Prodrug" refers to a compound that is transformed in vivo into a compound of Formula (I) or Formula (IA). Such a transformation can be affected, for example, by hydrolysis in blood or enzymatic transformation of the prodrug form in blood or tissue to the parent form. Prodrugs of the compounds disclosed herein may be, for example, esters. Esters that may be utilized as prodrugs in the present invention are phenyl esters, aliphatic ($C_{1-24}$) esters, acyloxymethyl esters, carbonates, carbamates, and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in Higuchi et al., *Pro-drugs as Novel Delivery Systems*, Vol. 14, A.C.S. Symposium Series; Roche, et al. ed., *Bioreversible Carriers in Drug Design*, American Pharmaceutical Association and Pergamon Press, 1987; Rautio et al., Prodrugs: Design and Clinical Applications, *Nature Reviews Drug Discovery*, 2008, 7, 255-270, and Hecker et al, Prodrugs of Phosphates and Phosphonates, *J. Med. Chem.*, 2008, 51, 2328-2345, all of which are incorporated herein by reference in their entireties.

"Metabolite" is a product produced through metabolism in the body of a specified compound or salt thereof. The metabolite of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow Parker et al., *McGraw-Hill Dictionary of Chemical Terms* (1984) McGraw-Hill Book Company, New York and Eliel et al., "*Stereochemistry of Organic Compounds*", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including but not limited to, diastereomers, enantiomers and atropisomers, as well as mixtures thereof such as racemic mixtures, form part of the present invention. Diastereomeric mixtures can be separated into their individual diastereoisomers on the basis of their physical and chemical differences by chromatography, crystallization, distillation or sublimation. Enantiomers can be separated by converting the enantiomeric mixture into a diastereomeric mixture by reacting with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. The intermediates and compounds of the invention may exist in tautomeric forms and all such tautomeric forms are within the scope of the invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

"Tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons. Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric (or conformational) mixtures of the present compounds are within the scope disclosed herein.

Additionally, unless otherwise stated, structures depicted herein are also meant to include compounds that differ only in the presence of one or more isotopically enriched atoms.

"Pharmaceutically acceptable salt" refers to organic or inorganic salts of a compound disclosed herein. Pharmaceutically acceptable salts are well known in the art. For example, the pharmaceutically acceptable salts are described in detail in Berge et al., *J. Pharmacol Sci,* 1977, 66: 1-19, which is incorporated herein by reference. Some non-limiting examples of the pharmaceutically acceptable salt formed by non-toxic acid include salts of an amino group formed with inorganic acids such as hydrochloric acid, hydrobromic acid, phosphoric acid, metaphosphoric acid, sulfuric acid, nitric acid and perchloric acid or with organic acids such as methylsulfonic acid, ethylsulfonic acid, acetic acid, trifluoroacetic acid, hydroxyacetic acid, hydroxyethyl sulfonic acid, oxalic acid, maleic acid, tartaric acid, citric acid, succinic acid, malonic acid, benzenesulfonic acid, p-toluene sulfonic acid, malic acid, fumaric acid, lactic acid, lactobionic acid by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, sodium malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ $alkyl)_4$ salts. This invention also envisions the quaternization of any basic nitrogen-containing groups of the compounds disclosed herein. Water or oil soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

"Solvate" refers to an association or complex of one or more solvent molecules and a compound disclosed herein. Some non-limiting examples of the solvent that form the solvate include water, isopropanol, ethanol, methanol, dimethylsulfoxide, ethyl acetate, acetic acid, and ethanolamine. The term "hydrate" refers to the complex where the solvent molecule is water.

The Pharmaceutical Compositions of the Compounds in the Invention

The invention features pharmaceutical compositions that include a compound of Formula (I) or Formula (IA), a compound listed herein, or a compound named in Examples 1 to 20, or a stereoisomer, a geometric isomer, a tautomer, a racemate, an N-oxide, a hydrate, a solvate, a metabolite, a pharmaceutically acceptable salt or a prodrug thereof, and a pharmaceutically acceptable carrier, excipient, diluent, adjuvant, vehicle or a combination thereof. The amount of the compound in the compositions disclosed herein is an effective and detectable amount for inhibiting DPP-IV activity in biological samples or patients.

It will also be appreciated that certain of the compounds disclosed herein can exist in free form for treatment, or where appropriate, as a pharmaceutically acceptable derivative thereof. Some non-limiting examples of the pharmaceutically acceptable derivative include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutically acceptable compositions disclosed herein further comprise a pharmaceutically acceptable carrier, a diluent, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Troy et al., *Remington: The Science and Practice of Pharmacy*, 21st ed., 2005, Lippincott Williams & Wilkins, Philadelphia, and Swarbrick et al., *Encyclopedia of Pharmaceutical Technology*, eds. 1988-1999, Marcel Dekker, New York, both of which are herein incorporated by reference in their entireties, discloses various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable carriers include ion exchangers; aluminium; aluminum stearate; lecithin; serum proteins such as human serum albumin; buffer substances such as phosphates, glycine, sorbic acid, and potassium sorbate; partial glyceride mixtures of saturated vegetable fatty acids; water; salts or electrolytes such as protamine sulfate, disodium hydrogen phosphate, potassium hydrogen phosphate, sodium chloride, and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

Compounds disclosed herein can be administered as the sole pharmaceutical agent or in combination with one or more other additional therapeutic (pharmaceutical) agents where the combination causes no unacceptable adverse effects. This may be of particular relevance for the treatment of diabetes, diabetic complications and other related diseases. Some non-limiting examples of the disease include diabetes mellitus type I, diabetes type II, diabetic retinopathy, diabetic neuropathy, diabetic nephropathy, insulin resistance, hypertension, hyperinsulinemia, elevated blood levels of fatty acids or glycerol, hyperlipidemia, obesity, hypertriglyceridemia, syndrome X, diabetic complications, atherosclerosis and hypertension, etc.

As used herein, the additional therapeutic agents include an anti-diabetic agent other than an DPP-IV inhibitor, an antihyperglycemic agent, an antiadipositas drug, an antihypertensive agent, an antiplatelet agent, an antiatherosclerotic drug, a lipid-lowering agent, an anti-inflammatorys or a combination thereof.

Wherein, the anti-diabetic agents other than an DPP-IV inhibitor include, but not limited to a biguanide (e.g., phenformin, and metformin), a sulfonylurea (e.g., acetohexamide, diabinese, glibenclamide, glipizide, gliclazide, glimepiride, glipentide, gliquidone, tolazamide and tolbutamide), a meglitinide, a glinide (e.g., repaglinide, and nateglinide), a glucosidase inhibitor (e.g., acarbose, adiposine, camiglibose, emiglitate, miglitol, voglibose, pradimicin and salbostatin), a PPAR agonist (e.g., balaglitazone, ciglitazone, darglitazone, rosiglitazone, isaglitazone, pioglitazone, rosiglitazone and troglitazone), a PPARα/γ dual agonist (such as CLX-0940, GW-1536, GW-1929, GW-2433, KRP-297, L-796449, LR-90, MK-0767 and SB-219994), a SGLT-2 inhibitor (e.g., dapagliflozin and canagliflozin), a glucagon-like peptide-1(GLP-1) agonist (e.g., exendin-3 and exendin-4), a protein tyrosine phosphatases-1B (PTP-1B) inhibitor (e.g., trodusquemine, hyrtiosal, extract and compounds are disclosed by Zhang, S. et al, *Drug Discovery Today*, 12(9/10), 373-381, 2007), insulin, an insulin mimetic, a glycogen phosphorylase inhibitor, a VPAC2 receptor agonist, a glucokinase activator, a glycogen phosphorylase inhibitor or a glucose-6-phosphatase inhibitor, an αP2 inhibitor, an acetyl-CoA carboxylase-2 (ACC-2) inhibitor, a phosphodiesterase (PDE)-10 inhibitor, a diacylglycerol acyltransferase (DGAT) 1 or 2 inhibitor, a glucose transporter 4 (GLUT4) regulator and a glutamine-fructose-6-phosphate amidotransferase (GFAT) inhibitor.

Wherein, the lipid-lowering agents include, but not limited to, an MTP inhibitor, an HMGCoA reductase inhibitor, a squalene synthase inhibitor, a fibric acid derivative, an ACAT inhibitor, a lipoxygenase inhibitor, a cholesterol absorption inhibitor, an ileal Na(+)/bile acid cotransporter inhibitor, an upregulators of LDL receptor activity, a bile acid sequestrant or niacin and a derivative thereof. In some embodiments, the lipid-lowering agent is selected from pravastatin, simvastatin, atorvastatin, fluvastatin, cerivastatin, atavastatin and rosuvastatin. Wherein, the anti-obesity agents include CB-1 antagonists (such as rimonabant, taranabant, surinabant, otenabant, SLV319 and AVE1625), gut-selective MTP inhibitors (such as dirlotapide, mitratapide and implitapide), CCKa agonists, 5-$HT_{2c}$ agonists (such as lorcaserin), MCR4 agonists, lipase inhibitors (such as cetilistat), $PYY_{3-36}$, opioid antagonist (such as naltrexone), oleoyl-estrone, obinepitide, pramlintide, tesofensine, leptin, liraglutide, bromocriptine, orlistat, exenatide, AOD-9604 and sibutramide.

Wherein, the suitable anti-inflammatory agents include genital tract/urinary tract infection preventatives and treatments. Exemplary agents include cranberries (*Vaccinium macrocarpon*) and cranberry derivatives, such as cranberry juice, cranberry extracts or flavonols of cranberries. Moreover, other suitable anti-inflammatory agents include, but not limited to, aspirin, non-steroidal anti-inflammatory drugs, glucocorticosteroid, sulfasalazine and selective cyclooxygenase-2 inhibitors, etc.

The compositions disclosed herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection and infusion techniques. In some embodiments, the compositions are administered orally, intraperitoneally or intravenously. Sterile injectable forms of the compositions disclosed herein include aqueous and oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that include water, Ringer's solution and isotonic sodium chloride solution. In addition, sterile, non-volatile oil can be conventionally employed as a solvent or suspending medium.

For this purpose, the non-volatile oil includes synthetic mono- or diglycerides. Fatty acids, such as oleic acid and its glyceride derivatives, which are useful in the preparation of injectables, can be used as natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Use of the Compounds and Pharmaceutical Compositions

Dipeptidyl peptidase-IV (DPP-IV) is a cell-surface protein which has many biological functions. It has a broad tissue distribution, such as intestine, kidney, liver, pancreas, placenta, *thymus*, spleen, epithelial cells, vascular endothelium, lymphoid and myeloid cells, and serum, etc, and distinct tissue and cell-type expression levels. DPP-IV is identified to the T cell activation marker CD26, and it can cleave a number of immunoregulatory, endocrine and neurological peptides in vitro. This has suggested a potential role for this peptidase in a variety of disease processes in humans or other species.

Pharmacological experimental results showed that DPP-IV inhibitors can significantly inhibit the activity of DPP-IV, protect the activity of GLP-1, boost insulin production, decrease glucagon after the meals, lower blood sugar and improve glucose tolerance; and DPP-IV inhibitors have the protective effect on GIP, which can increase the concentration of GIP and enhance the promotion effect of it in insulin production. DPP-IV inhibitors also can improve glucose and lipoprotein lipids metabolism and prevent weight gain.

The amount of the compound or the compound of the compositions disclosed herein is an effective and detectable amount for inhibiting dipeptidyl peptidase-IV (DPP-IV) activity, and has good inhibiting effect on DPP-IV. Therefore, the compound of the invention and all crystal forms, pharmaceutically acceptable derivates thereof, such as pharmaceutically acceptable salts, N-oxides, hydrates, solvates or prodrugs, and the drugs that are prepared from pharmaceutical compositions containing the compound of the invention as the main active ingredient can be used for preventing and treating the type II diabetes and related diseases or improving symptoms of these diseases.

Compounds disclosed herein would be useful for, but not limited to, preventing or treating diabetes or related diseases, or lessening diabetes or related diseases, delaying the progression or onset of diabetes or related diseases or increasing levels of HDL in a patient by administering to the patient a compound or a composition disclosed herein in an effective amount. Such diseases include, but not limited to, diabetes, especially diabetes II, and diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, diabetic complications, atherosclerosis, and hypertension.

Moreover, compounds or pharmaceutical compositions disclosed herein also suit for preventing or treating the damage of diabetes in later stages, such as kidney disease, retinopathy, neuropathy, myocardial infarction, peripheral arterial disease, thrombosis, arteriosclerosis, inflammation, immunological diseases, autoimmune diseases such as AIDS, asthma, osteoporosis, cancer, psoriasis, Alzheimer's disease, schizophrenia and infectious diseases.

Besides being useful for primate treatment, such as human, these compounds are also useful for the rest of the mammal treatment of related diseases. These mammals include, but not limited to cattles, sheep, goats, horses, dogs, cats, guinea pigs, rats and other bovine, canine, felid, murine, and the like. In addition, these compounds are also useful for other species treatment, such as birds. As used herein, the compounds disclosed herein include the pharmaceutically acceptable derivatives thereof Also provided herein is a method, which further comprises administering the compound or the pharmaceutical composition disclosed herein, further comprising administering to the patient additional therapeutic agents (combination therapy), wherein the additional therapeutic agent is anti-diabetic agent other than a DPP-IV inhibitor, an anti-hyperglycemic agent, an antiadipositas drug, an antihypertensive agent, an antiplatelet agent, an antiatherosclerotic drug, a lipid-lowering agent, an anti-inflammatory or a combination thereof. Wherein the additional therapeutic agents are applicable to treated diseases, and the additional therapeutic agents can be administered in combination with the compound or the pharmaceutical composition disclosed herein, the compound or the pharmaceutical composition disclosed herein as a unit dose or separately from the compound or composition as a part of multiple unit dose. The additional therapeutic agents may be administered at the same time as a compound disclosed herein or at a different time.

An "effective amount" or "effective dose" of the compound or pharmaceutically acceptable composition is an amount that is effective in treating or lessening the severity of one or more of the aforementioned disorders. The compounds and compositions, according to the method disclosed herein, may be administered using any amount and any route of administration effective for treating or lessening the severity of the disorder or disease. The exact amount required will vary from subject to subject, depending on the species, age, and general condition of the subject, the severity of the infection, the particular agent, its mode of administration, and the like. A compound or composition can also be administered with one or more other therapeutic agents as discussed above.

GENERAL SYNTHETIC PROCEDURES

Generally, the compounds disclosed herein may be prepared by methods described herein, wherein the substituents are as defined for Formula (I) or (IA), above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

The structures of all compounds disclosed herein were identified by nuclear magnetic resonance ($^1$H-NMR, $^{13}$C-NMR). $^1$H-NMR, $^{13}$C-NMR chemical shifts were recorded as ppm ($10^{-6}$). $^1$H-NMR, $^{13}$C-NMR were performed on a Bruker Ultrashield-400 spectrometer. The appropriate solvent used was deuterated-chloroform ($CDCl_3$), deuterated-methanol ($CD_3OD$-$d_4$) or deuterated-dimethyl sulfoxide (DMSO-$d_6$).

LC-MS was measured on Agilent-6120 Quadrupole LC/MS mass spectrometer.

GC-MS was measured on Agilent 7890A/5975C GC/MS mass spectrometer.

The thin-layer silica gel used was Yantai Huanghai $HSGF_{254}$ silica gel plate.

Column chromatography generally used was Qingdao Ocean Chemical Factory 300 to 400 mesh silica gel as a stationary phase.

The staring materials of the present invention were purchased from Shanghai Accela Company, Energy Company, J&K, Chengdu Aiertai Company, Alfa Company etc, or prepared by the conventional synthesis methods in the prior art.

Unless otherwise stated, reactions disclosed herein were carried out in a nitrogen atmosphere.

The term "nitrogen atmosphere" refers to an atmosphere in a reaction flask equipped with a balloon filled with about 1 L nitrogen.

The term "hydrogen atmosphere" refers to an atmosphere in a reaction flask equipped with a balloon filled with about 1 L hydrogen or a high pressure stainless steel reaction vessel with about 1 L hydrogen.

Unless otherwise stated, the solution used in example refers to an aqueous solution.

Unless otherwise stated, the reaction temperature was room temperature.

Unless otherwise stated, room temperature was from 20° C. to 30° C.

The reaction process in the examples was monitored by thin layer chromatography (TLC). The solvent system for development of a TLC plate comprises dichloromethane and methanol, dichloromethane and ethyl acetate, or petroleum ether and ethyl acetate. The volume ratio of the solvents in the solvent system was adjusted according to the polarity of the compounds.

The elution system of column chromatography comprises: A: petroleum ether and ethyl acetate, B: dichloromethane and ethyl acetate, and C: dichloromethane and methanol. The volume ratio of the solvents in the elution system was adjusted according to the polarity of the compounds, and sometimes it was also adjusted by adding a basic agent such as aqueous ammonia or an acidic agent such as acetic acid.

HPLC refers to High Performance Liquid Chromatography.

HPLC was determined on Agilent 1200DAD high pressure liquid chromatography spectrometer (Zorbax Eclipse Plus C18 150×4.6 mm chromatographic column).

The test condition of HPLC: The run time was 30 min. The column temperature was 35° C. The detection was carried out at the wavelength of 210 nm and 254 nm using PDA detector. The mobile phase was $H_2O$ (A) and acetonitrile (B). The flow rate was 1.0 mL/min.

Scheme 1

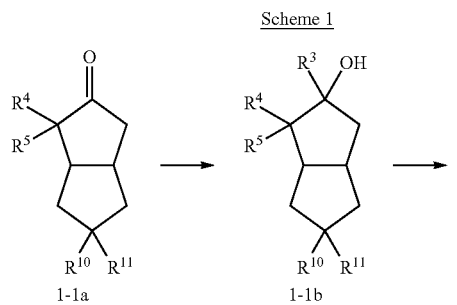
1-1a → 1-1b

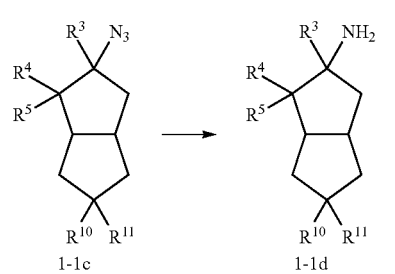
1-1c → 1-1d

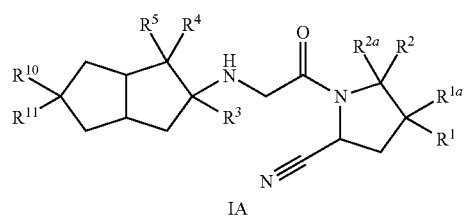
IA

Scheme 2

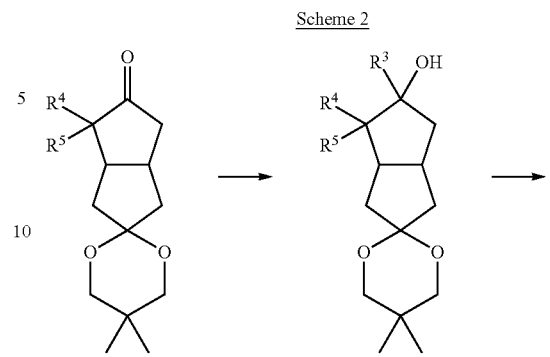
1-1e → 1-1f

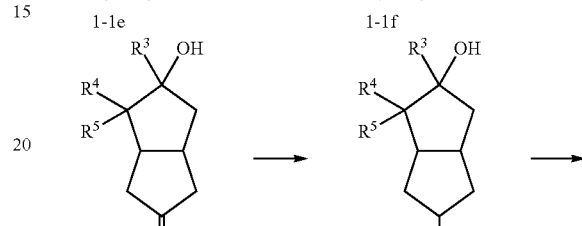
1-1g → 1-1h

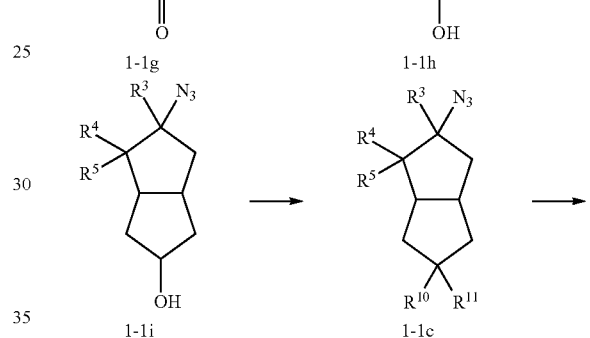
1-1i → 1-1c

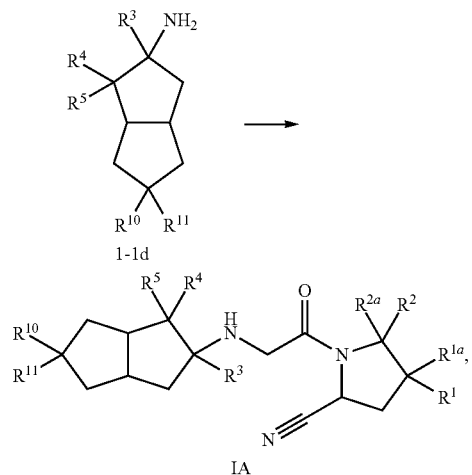
1-1d → IA

The compound of formula (IA) can be prepared by a general synthetic procedure illustrated in Scheme 1, wherein each of $R^1$, $R^{1a}$, $R^2$, $R^{2a}$, $R^3$, $R^4$, $R^5$, $R^{10}$ and $R^{11}$ is as defined herein.

Grignard reaction of the compound of formula (1-1a) affords the compound of formula (1-1b). The compound of formula (1-1b) can be subjected to azidation with sodium azide in a halohydrocarbon solvent in the presence of an acid to obtain the compound of formula (1-1c). The compound of formula (1-1c) can be converted into the compound of formula (1-1d) using one of the following two methods.

(11) The compound of formula (1-1c) can be reduced in a solvent to produce the compound of formula (1-1d).

(12) When $R^{10}$ or $R^{11}$ of the formula (1-1c) is hydroxy, the compound of formula (1-1c) can react with an aromatic acid in the presence of triphenylphosphine and diethyl azodicarboxylate to produce an ester. The ester can be hydrolyzed in a polar solvent and under alkaline conditions to produce a stereoisomer of formula (1-1c), that the configuration of the chiral carbon atom attached with $R^{10}$ and $R^{11}$ is inversed. The compound with the configuration inversion of the chiral carbon atom attached with $R^{10}$ and $R^{11}$ (that is the stereoisomer of formula (1-1c)) can be reduced to produce the compound of formula (1-1d).

The compound of formula (1-1d) can react with N-haloacetyl-2-cyano-pyrrolidine in a polar solvent under alkaline conditions to produce the compound of formula (IA);

The solvent is selected from a non-polar solvent, a weak polar solvent and a polar solvent.

The compound of formula (IA) can be prepared by a general synthetic procedure illustrated in Scheme 2, wherein each of $R^1$, $R^{1a}$, $R^2$, $R^{2a}$, $R^3$, $R^4$, $R^5$, $R^{10}$ and $R^{11}$ is as defined herein.

Reaction of the compound of formula (1-1e) with Grignard reagent can give the compound of formula (1-1f). The protection group of the compound of formula (1-1f) can be removed in a polar solvent under acidic conditions to afford the compound of formula (1-1g). The compound of formula (1-1g) can be reduced by a reducing agent in a polar solvent to give the compound of formula (1-1h). The compound of formula (1-1h) can be subjected to azidation with sodium azide in a halohydrocarbon solvent in the presence of an acid to obtain the compound of formula (1-1i). The compound of formula (1-1i) can be converted into the compound of formula (1-1d) using one of the following three methods.

(21) The compound of formula (1-1i) can be reduced in a solvent to produce the compound of formula (1-1d). The solvent is selected from a non-polar solvent, a weak polar solvent and a polar solvent.

(22) The compound of formula (1-1i) can react with an aromatic acid in the presence of triphenylphosphine and diethyl azodicarboxylate to produce an ester. The ester can be hydrolyzed in a polar solvent and under alkaline conditions to produce a stereoisomer of formula (1-1i), that the configuration of the chiral carbon atom attached with hydroxy is inversed. The compound with the configuration inversion of the chiral carbon atom attached with hydroxy (that is a stereoisomer of formula (1-1i)) can be reduced to produce the compound of formula (1-1d). The solvent is selected from a non-polar solvent, a weak polar solvent and a polar solvent.

(23) The compound of formula (1-1i) or the compound with the configuration inversion of the chiral carbon atom attached with hydroxy (that is a stereoisomer of formula (1-1i)) can react with a halohydrocarbon reagent, acyl halide, or anhydride under alkaline conditions to produce the compound of formula (1-1c). The compound of formula (1-1c) can be reduced in a solvent to give the compound of formula (1-1d). The solvent is selected from a non-polar solvent, a weak polar solvent and a polar solvent.

The compound of formula (1-1d) can react with N-haloacetyl-2-cyano-pyrrolidine in a polar solvent under alkaline conditions to produce the compound of formula (IA).

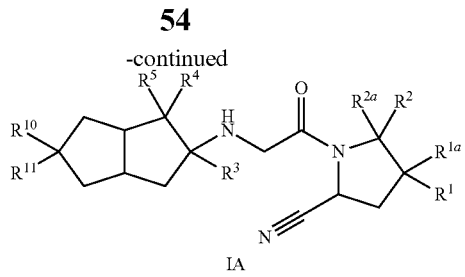

The compound of formula (IA) can be prepared by a general synthetic procedure illustrated in Scheme 3, wherein each of $R^1$, $R^{1a}$, $R^2$, $R^{2a}$, $R^3$, $R^4$, $R^5$, $R^{10}$ and $R^{11}$ is as defined herein.

The compound of formula (1-1a) can react with diethyl oxalate in a polar solvent under alkaline conditions to produce the compound of formula (1-1j). The compound of formula (1-1j) can react with formaldehyde in a polar solvent under alkaline conditions to produce the compound of formula (1-1k). The compound of formula (1-1k) can react with trimethylsulfoxonium iodide in a polar solvent under alkaline conditions to produce the compound of formula (1-1l). Condensation reaction of the compound of formula (1-1l) with hydroxylamine hydrochloride under alkaline conditions can produce the compound of formula (1-1m). Reduction reaction of the compound of formula (1-1m) with a reducing agent can afford the compound of formula (1-1d). The compound of formula (1-1d) can react with N-haloeacetyl-2-cynao-pyrrolidine in a polar solvent under alkaline conditions to produce the compound of formula (IA).

Scheme 3

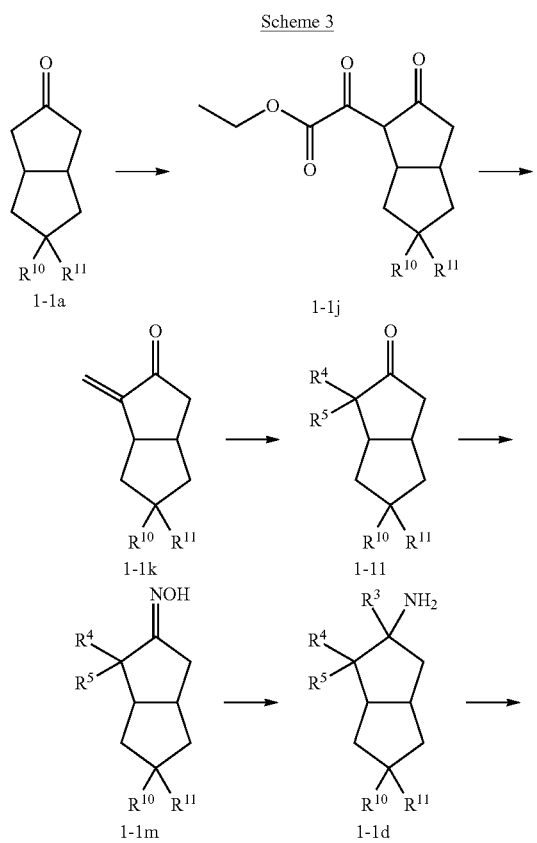

Scheme 4

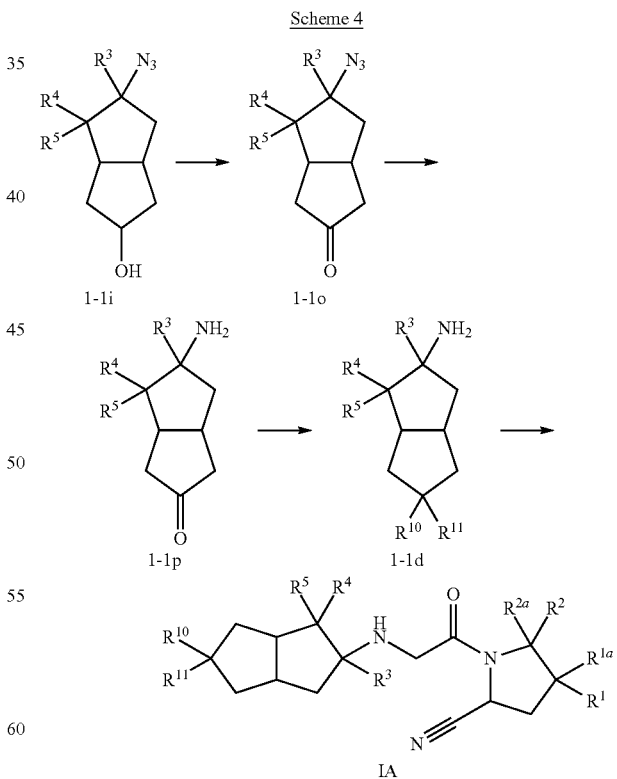

The compound of formula (IA) can be prepared by a general synthetic procedure illustrated in Scheme 4, wherein each of $R^1$, $R^{1a}$, $R^2$, $R^{2a}$, $R^3$, $R^4$, $R^5$, $R^{10}$ and $R^{11}$ is as defined herein.

The compound of formula (1-1i) can react with an oxidizing agent in a halohydrocarbon solvent to give the compound of formula (1-1o). The compound of formula (1-1o) can react with a reducing agent in a solvent to give the compound of formula (1-1p). The compound of formula (1-1p) can react with trimethylsulfoxonium iodide under alkaline conditions to produce the compound of formula (1-1d). The compound of formula (1-1d) can react with N-haloacetyl-2-cynao-pyrrolidine in a polar solvent under alkaline conditions to produce the compound of formula (IA). The solvent is selected from a non-polar solvent, a weak polar solvent and a polar solvent.

Scheme 5

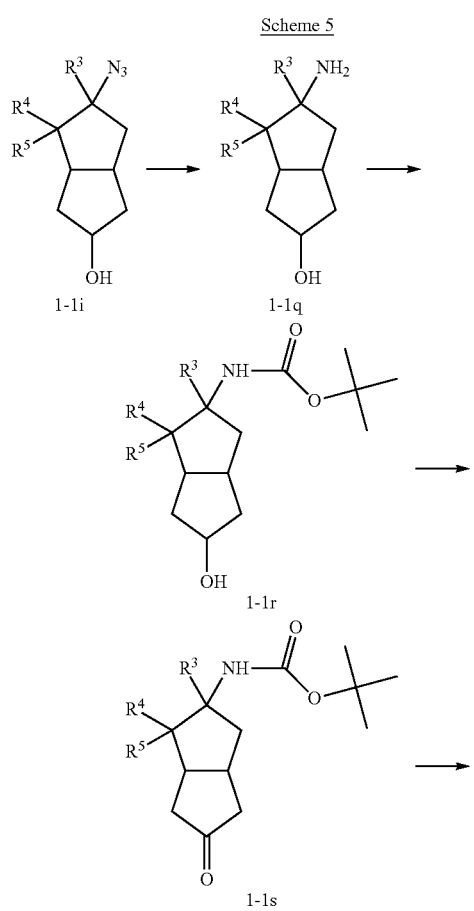

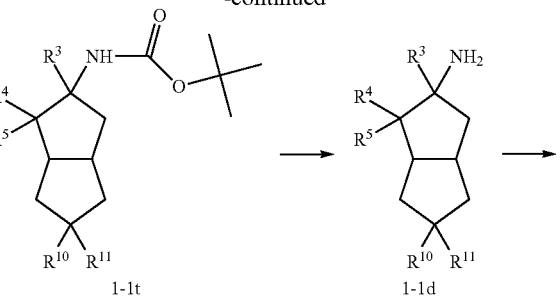

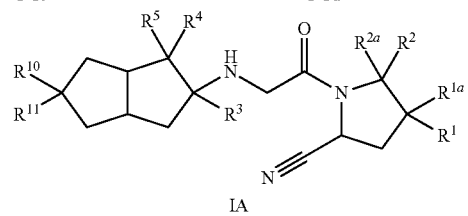

The compound of formula (IA) can be prepared by a general synthetic procedure illustrated in Scheme 5, wherein each of $R^1$, $R^{1a}$, $R^2$, $R^{2a}$, $R^3$, $R^4$, $R^5$, $R^{10}$ and $R^{11}$ is as defined herein.

The compound of formula (1-1i) can be reduced to afford the compound of formula (1-1q). The compound of the formula (1-1q) can react with di-tert-butyl dicarbonate ester to produce the compound of formula (1-1r). The compound of formula (1-1r) can react with an oxidizing agent to give the compound of formula (1-1s). The compound of formula (1-1s) can react with p-tosyl isocyanate under alkaline conditions to produce the compound of formula (1-1t). The compound of formula (1-1t) can react with a reducing agent in a polar solvent to give the compound of formula (1-1d). The compound of formula (1-1d) can react with N-haloacetyl-2-cynao-pyrrolidine in a polar solvent under alkaline conditions to produce the compound of formula (IA).

EXAMPLE

Example 1

(S)-1-(2-(((2r,3 aR,5S,6aS)-5-Methoxy-2-methyloctahydropentalen-2-yl)amino)acetyl) pyrrolidine-2-carbonitrile

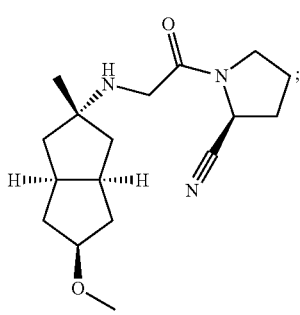

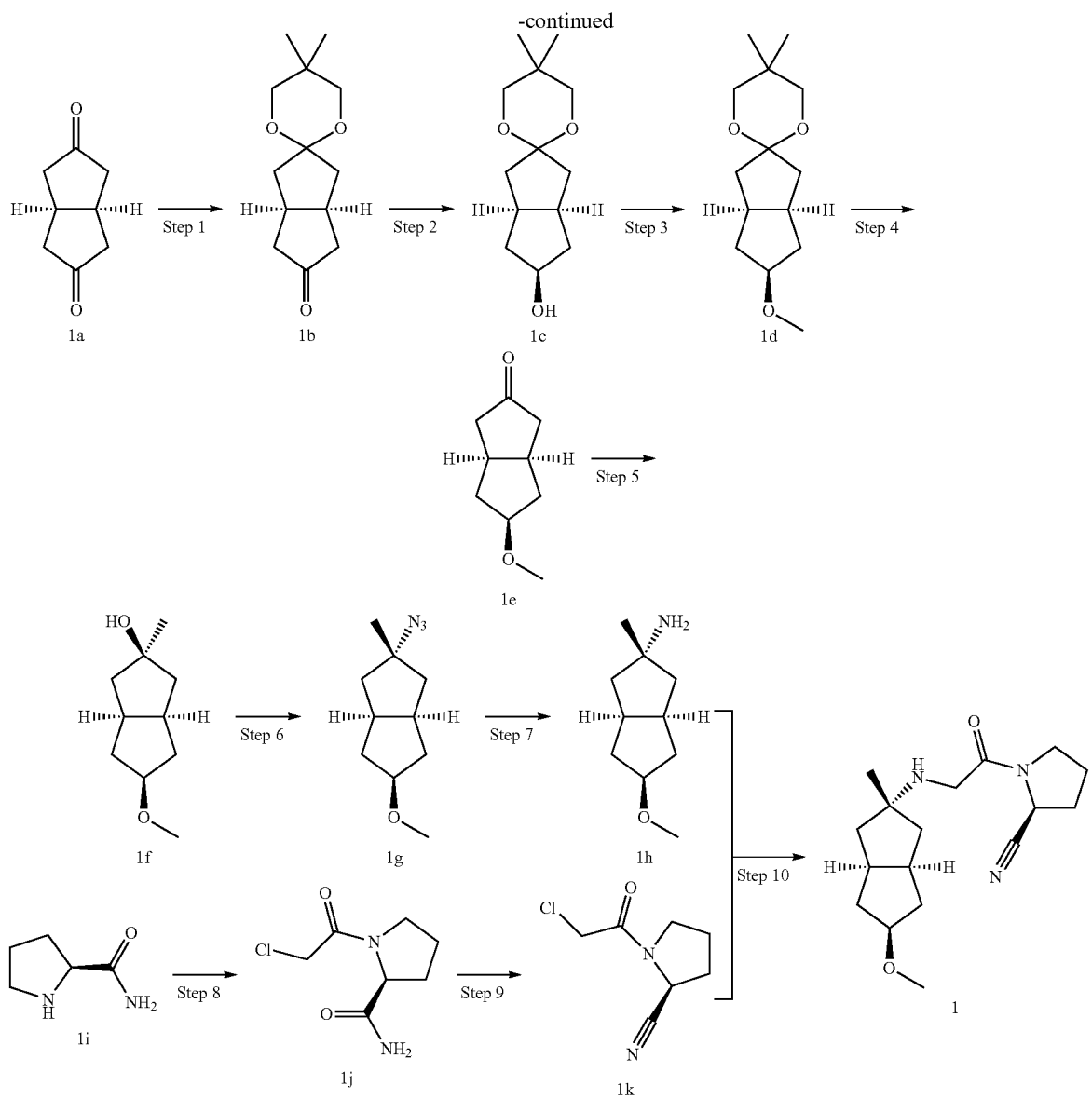

Step 1) (3a'R,6a'S)-5,5-dimethyltetrahydro-1'H-spiro[[1,3]dioxane-2,2'-pentalen]-5'(3'H)-one A mixture of (3as,6as)-tetrahydropentalene-2,5(1H,3H)-dione 1a (2.00 g, 14.47 mmol, Chengdu Altus biological technology Co., Ltd), neopentyl glycol (1.51 g, 14.49 mmol, Aladdin), p-toluene sulfonic acid (25 mg, 0.13 mmol, Guangzhou huada chemical reagent Co., Ltd) and toluene (150 mL) was heated to reflux for 5 hours. The mixture was cooled to rt and concentrated in vacuo. The residue was purified by silica gel column chromatography (petroleum ether:ethyl acetate (V/V)=4:1) to give the title compound 1b as a yellow solid (1.96 g, 60.3%). The compound was characterized by the following spectroscopic data:

MS m/z (ESI): 225.0 (M+1); and $^1$H NMR (400 MHz, CDCl$_3$) δ: 3.50 (s, 2H), 3.45 (s, 2H), 2.80 (m, 2H), 2.44 (m, 2H), 2.27 (m, 2H), 2.15 (m, 2H), 1.80 (m, 2H), 0.96 (s, 6H).

Step 2) (3a'R,5's,6a'S)-5,5-dimethylhexahydro-1'H-spiro[[1,3]dioxane-2,2'-pentalen]-5'-ol To a solution (3a'R,6a'S)-5,5-dimethyltetrahydro-1'H-spiro[[1,3]dioxane-2,2'-pentalen]-5'(3'H)-one 1b (48.0 g, 0.214 mol) in ethyl acetate (900 mL) was added Lithium tri-tert-butoxyaluminum hydride (108.0 g, 0.425 mmol, Beijing Ouhe technology Co., Ltd) at 0° C. The mixture was stirred at 0° C. for 4 hours and quenched with water (240 mL). The resulting mixture was extracted with ethyl acetate (300 mL×3). The combined organic layers were dried over anhydrous sodium sulfate and concentrated in vacuo. The residue was purified by silica gel column chromatography (petroleum ether:ethyl acetate (V/V)=3:1) to give the title compound 1c as a white solid (36.0 g, 74.4%). The compound was characterized by the following spectroscopic data:

MS m/z (ESI): 227.3 (M+1); and

¹H NMR (400 MHz, CDCl₃) δ: 4.18 (m, 1H), 3.50 (s, 2H), 3.47 (s, 2H), 2.52 (m, 2H), 2.19 (m, 2H), 2.06 (m, 2H), 1.89 (m, 2H), 1.49 (m, 2H), 0.96 (s, 6H).

Step 3) (3a'R,5's,6a'S)-5'-methoxy-5,5-dimethyl-hexahydro-1'H-spiro[[1,3]dioxane-2,2'-pentalene]

To a solution of (3a'R,5's,6a'S)-5,5-dimethylhexahydro-1'H-spiro[[1,3]dioxane-2,2'-pentalen]-5'-ol 1c (9.86 g, 43.6 mmol) in tetrahydrofuran (150 mL) was added sodium hydride (2.09 g, 87.0 mmol, 60%, Tianjin da mao chemical reagent company) at 0° C. The mixture was stirred at rt for 1 hour and methyl iodide (24.8 g, 174.7 mmol, Chengdu kelon chemical reagent factory) was added. The resulting mixture was heated to 60° C. and stirred for 3 hours. The reaction mixture was cooled to rt and quenched with water. The resulting mixture was extracted with ethyl acetate (150 mL×3). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=8:1) to give the title compound 1d as amber oil (8.96 g, 85.6%). The compound was characterized by the following spectroscopic data:
MS m/z (ESI): 241.3 (M+1); and
¹H NMR (400 MHz, CDCl₃) δ: 3.77 (m, 1H), 3.48 (s, 2H), 3.46 (s, 2H), 3.29 (s, 3H), 2.41 (m, 2H), 2.25 (m, 2H), 1.98 (m, 2H), 1.70 (m, 2H), 1.50 (m, 2H), 0.96 (s, 6H).

Step 4) (3aR,5s,6aS)-5-methoxyhexahydropentalen-2(1H)-one

A mixture of (3a'R,5's,6a'S)-5'-methoxy-5,5-dimethyl-hexahydro-1'H-spiro[[1,3]dioxane-2,2'-pentalene] 1d (8.96 g, 37.3 mmol) and p-toluenesulfonic acid monohydrate in acetone-water mixtures (205 mL, V/V=40/1) was stirred at rt for 3 hours. The reaction mixture was extracted with ethyl acetate (150 mL×3). The combined organic layers were washed with saturated aqueous sodium bicarbonate (50 mL), dried over anhydrous sodium sulfate and concentrated in vacuo. The residue was purified by silica gel column chromatography (petroleum ether:ethyl acetate (V/V)=5:1) to give the title compound 1e as colorless oil (5.51 g, 95.8%). The compound was characterized by the following spectroscopic data:
MS m/z (ESI): 155.2 (M+1); and
¹H NMR (400 MHz, CDCl₃) δ: 3.86 (m, 1H), 3.25 (s, 3H), 2.74 (m, 2H), 2.46 (m, 2H), 2.18 (m, 2H), 2.06 (m, 2H), 1.63 (m, 2H).

Step 5) (2r,3aR,5s,6aS)-5-methoxy-2-methyloctahydropentalen-2-ol

To a solution of methylmagnesium bromide (6 mL, 3 M in ether, Shao yuan chemical technology (Shanghai) Co., Ltd) in tetrahydrofuran (20 mL) was added a solution of (3aR,5s,6aS)-5-methoxyhexahydropentalen-2(1H)-one 1e (2.0 g, 12.97 mmol) in tetrahydroxfuran (30 mL) at 0° C. over a period of 15 min. The mixture was allowed to warm up to rt, and stirred at 67° C. for 14 hours. The reaction mixture was cooled to 0° C. in an ice bath and quenched with saturated aqueous ammonium chloride (150 mL). The resulting mixture was extracted with dichloromethane (300 mL×3). The combined organic layers were washed with saturated aqueous sodium chloride (150 mL), dried over anhydrous sodium sulfate and concentrated in vacuo. The residue was purified by silica gel column chromatography (petroleum ether:ethyl acetate (V/V)=6:1) to give the title compound 1f as colorless oil (1.53 g, 69.2%). The compound was characterized by the following spectroscopic data:
¹H NMR (400 MHz, CDCl₃) δ: 3.80 (m, 1H), 3.30 (s, 3H), 3.22 (s, 1H), 2.53 (m, 2H), 2.02 (m, 2H), 1.97 (m, 2H), 1.78 (m, 2H), 1.69 (m, 2H), 1.26 (s, 3H); and
¹³C NMR (100 MHz, CDCl₃) δ: 85.6, 81.4, 56.6, 49.0, 41.2, 39.3, 28.3.

Step 6) (2r,3aR,5r,6aS)-2-azido-5-methoxy-2-methyloctahydropentalene

To a sulfuric acid solution (6.8 mL, 9.12 M) was added sodium azide (0.57 g, 8.82 mmol, Tianjin tian da chemical reagent Co., Ltd) at 0° C. with stirring. The mixture was stirred for 30 min and a solution of (2r,3aR,5s,6aS)-5-methoxy-2-methyloctahydropentalen-2-ol 1f (1.00 g, 5.9 mmol) in trichloromethane (10 mL) was added. The resulting mixture was stirred at 50° C. for 8 hours, cooled to 0° C. in an ice-water bath, and extracted with dichloromethane (50 mL×3). The combined organic layers were washed with saturated aqueous sodium chloride (50 mL), dried over anhydrous sodium sulfate and concentrated in vacuo. The residue was purified by silica gel column chromatography (petroleum ether:ethyl acetate (V/V)=10:1) to give the title compound 1g as yellow oil (0.77 g, 66.9%). The compound was characterized by the following spectroscopic data:
¹H NMR (400 MHz, CDCl₃) δ: 3.82 (m, 1H), 3.26 (s, 3H), 2.63 (m, 2H), 1.92 (m, 2H), 1.85 (m, 2H), 1.51 (m, 4H), 1.39 (s, 3H).

Step 7) (2r,3aR,5r,6aS)-5-methoxy-2-methyloctahydropentalen-2-amine

To a solution of (2r,3aR,5r,6aS)-2-azido-5-methoxy-2-methyloctahydropentalene 1g (0.77 g, 3.9 mL) in methanol/tetrahydrofuran (80 mL, V/V=1:1) was added Pd/C (0.60 g, 10%, W/W=55%, Shaanxi kai da chemical reagent Co., Ltd). The mixture was stirred under H₂ for 14 hours. The reaction mixture was filtered. The filtrate was concentrated in vacuo. The residue was purified by silica gel column chromatography (dichloromethane:methanol (V/V)=8:1) to give the title compound 1l as a white solid (0.28 g, 42.4%). The compound was characterized by the following spectroscopic data:
MS m/z (ESI): 170.2 (M+1); and
¹H NMR (400 MHz, CDCl₃) δ: 3.77 (m, 1H), 3.28 (s, 3H), 2.64 (m, 2H), 1.95 (m, 2H), 1.76 (m, 2H), 1.46 (m, 4H), 1.25 (s, 3H).

Step 8) (S)-1-(2-chloroacetyl)pyrrolidine-2-carboxamide

To a mixture of chloroacetyl chloride (9.94 g, 88.0 mmol, Shanghai han hong chemical Co., Ltd) and potassium carbonate (48.5 g, 350.9 mmol, Chengdu kelon company) in tetrahydrofuran was added a solution of L-prolinamide 1i (9.00 g, 78.8 mmol, Shao yuan chemical (Shanghai) technology Co., Ltd) in tetrahydrofuran (300 mL) dropwise over a period of 1 hour. The mixture was further stirred for 2.5 hours at rt to give the title compound 1j. The reaction mixture was filtered. The filtrate was concentrated in vacuo. The residue was used without further purification. The compound was characterized by the following spectroscopic data:
MS m/z (ESI): 191.0 (M+1).

Step 9) (S)-1-(2-chloroacetyl)pyrrolidine-2-carbonitrile

To a solution of (S)-1-(2-chloroacetyl)pyrrolidine-2-carboxamide 1j (prepared in Step 8) was added trifluoroacetic anhydride (30.2 g, 142.8 mmol, Aladdin) at rt. The mixture was stirred at rt for 14 hours and concentrated in vacuo. The residue was dissolved in ethyl acetate (20 mL). The solution was washed with saturated aqueous sodium bicarbonate (200 mL) and then saturated aqueous sodium chloride (200 mL), dried over anhydrous sodium sulfate and concentrated in vacuo give the title compound 1k as brown oil (9.35 g, 61.8%) without further purification. The compound was characterized by the following spectroscopic data:

MS m/z (ESI): 173.1 (M+1); and $^1$H NMR (400 MHz, DMSO-d$_6$) δ: 4.79-4.78 (m, 1H), 4.35-4.45 (s, 2H), 3.61-3.3.66 (m, 1H), 3.39-3.50 (m, 1H), 2.49-2.51 (m, 2H), 2.03-2.16 (m, 2H).

Step 10) (S)-1-(2-(((2r,3aR,5S,6aS)-5-methoxy-2-methyloctahydropentalen-2-yl)amino) acetyl) pyrrolidine-2-carbonitrile To a solution of (2r,3aR,5r,6aS)-5-methoxy-2-methyloctahydropentalen-2-amine 1h (2.15 g, 12.7 mmol) in N,N-dimethylformamide (150 mL) were added (S)-1-(2-chloroacetyl)pyrrolidine-2-carbonitrile 1k (2.19 g, 12.7 mmol), potassium iodide (2.11g, 12.7 mmol) and potassium carbonate (1.76 g, 12.7 mmol). The mixture was stirred at rt for 14 hours and filtered. The filtrate was concentrated in vacuo. The residue was dissolved in dichloromethane (80 mL). The solution was washed with saturated aqueous sodium chloride (80 mL), dried over anhydrous sodium sulfate and concentrated in vacuo. The residue was purified by silica gel column chromatography (dichloromethane:methanol (V/V)=15:1) to give the title compound 1 as yellow oil (1.0 g, 25.8%). The compound was characterized by the following spectroscopic data:

MS m/z (ESI): 306.1 (M+1); and $^1$H NMR (400 MHz, CDCl$_3$) δ: 4.75 (d, 1H), 3.80 (m, 1H), 3.62 (m, 1H), 3.45 (m, 1H), 3.31 (s, 2H), 3.29 (s, 3H), 2.60 (m, 2H), 2.15 (m, 2H), 1.92 (m, 6H), 1.51 (m, 2H), 1.42 (m, 2H), 1.16 (s, 3H).

Example 2

(2S,4S)-4-Fluoro-1-(2-(((2r,3aR,5S,6aS)-5-methoxy-2-methyloctahydropentalen-2-yl)amino)acetyl)pyrrolidine-2-carbonitrile

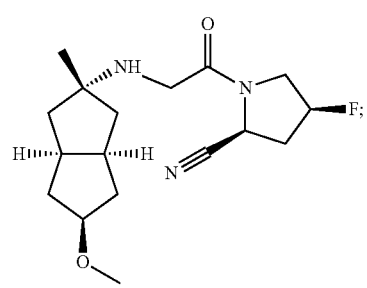

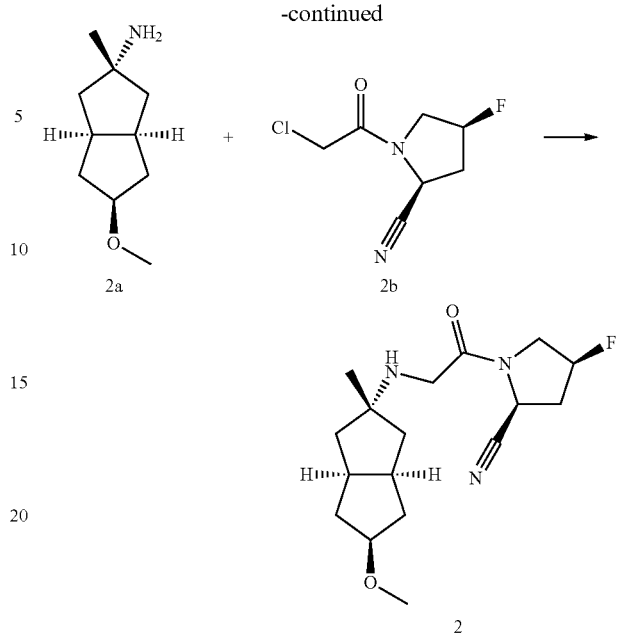

To a solution of (2r,3aR,5r,6aS)-5-methoxy-2-methyloctahydropentalen-2-amine 2a (1.50 g, 8.87 mmol, prepared in Step 7 of example 1) in N,N-dimethylformamide-dichloromethane mixtures (100 mL, V/V=3:1) were added potassium iodide (1.62 g, 9.76 mmol), potassium carbonate (1.35 g, 9.76 mmol) and (2S,4S)-1-(2-chloroacetyl)-4-fluoropyrrolidine-2-carbonitrile 2b (1.86 g, 9.76 mmol, Chengdu al Thai biological technology Co., Ltd). The reaction mixture was stirred at rt for 14 hours and concentrated in vacuo. The residue was purified by silica gel column chromatography (dichloromethane:methanol (V/V)=20:1) to give the title compound 2 as a yellow solid (0.87 g, 30.3%). The compound was characterized by the following spectroscopic data:

MS m/z (ESI): 324.2 (M+1); and $^1$H NMR (400 MHz, CDCl$_3$) δ: 5.22-5.49 (m, 1H), 4.94 (d, 1H), 3.87 (m, 2H), 3.72 (m, 1H), 3.33 (s, 2H), 3.29 (s, 3H), 2.71 (m, 2H), 2.63 (m, 1H), 2.24 (m, 1H), 1.90 (m, 4H), 1.73 (m, 2H), 1.59 (m, 2H), 1.18 (s, 3H).

Example 3

(2S,4S)-4-Fluoro-1-(2-(((2r,3aR,5S,6aS)-5-hydroxy-2-methyloctahydropentalen-2-yl)amino)acetyl)pyrrolidine-2-carbonitrile

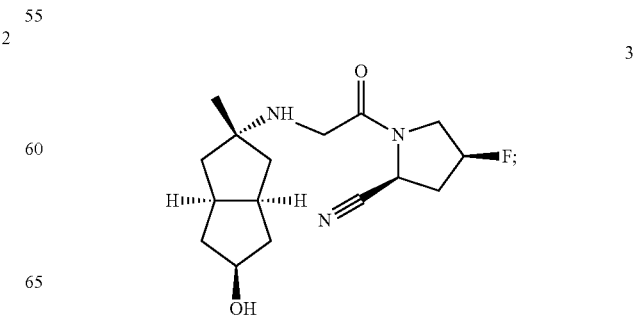

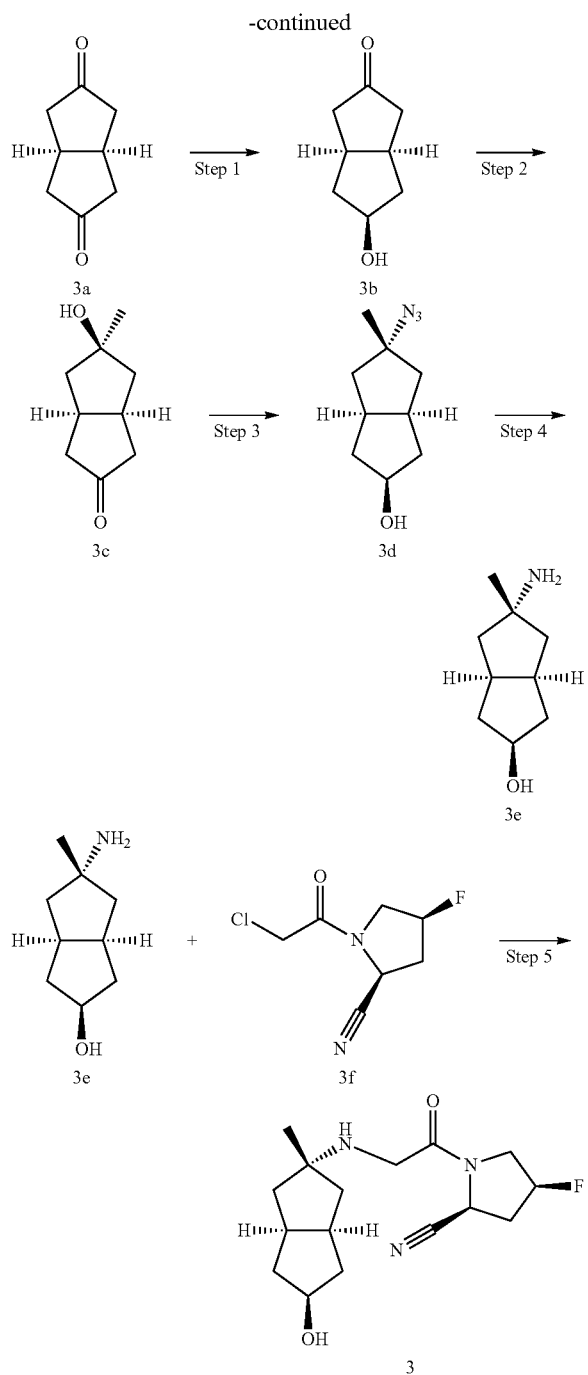

ether:ethyl acetate (V/V)=6:1) to give the title compound 3b as pale yellow oil (42 g, 41.3%). The compound was characterized by the following spectroscopic data:

GC-MS m/z (EI): 140.1 (M); and
$^1$H NMR (400 MHz, CDCl$_3$) δ: 4.38 (m, 1H), 2.80 (m, 2H), 2.52 (m, 2H), 2.28 (m, 2H), 2.15 (m, 2H), 1.59 (m, 2H).

Step 2) (2r,3aR,5s,6aS)-2-methyloctahydropentalene-2,5-diol

To a solution of methylmagnesium bromide (35.7 mL, 3 M in ether, Shao yuan chemical technology (Shanghai) Co., Ltd) in tetrahydrofuran (200 mL) was added a solution of (3aR,5s,6aS)-5-hydroxyhexahydropentalen-2(1H)-one 3b (5.0 g, 0.036 mmol) in tetrahydroxfuran (40 mL) at −20° C. with stirring. The mixture was stirred at −20° C. for 1 hour and allowed to warm up to rt, and stirred at 65° C. for 14 hours. The reaction mixture was quenched with hydrochloric acid (50 mL, 1 M). The resulting mixture was extracted with ethyl acetate (100 mL×3). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=4:1) to give the title compound 3c as pale yellow oil (4.4 g, 78.3%). The compound was characterized by the following spectroscopic data:

GC-MS m/z (EI): 156.2 (M); and
$^1$H NMR (400 MHz, DMSO-d$_6$) δ: 4.59 (d, 1H), 4.39 (s, 1H), 3.94 (m, 1H), 2.26 (m, 2H), 1.88 (m, 2H), 1.66 (m, 2H), 1.57 (m, 2H), 1.39 (m, 2H), 1.10 (s, 3H).

Step 3) (2r,3aR,5r,6aS)-5-azido-5-methyloctahydropentalen-2-ol

To a sulfuric acid solution (19.6 mL, 9.27 M) was added sodium azide (2.56 g, 39.4 mmol, Tianjin tian da chemical reagent Co., Ltd) at 0° C. with stirring. The mixture was stirred at rt for 30 min and a solution of (2r,3aR,5s,6aS)-2-methyloctahydropentalene-2,5-diol 3c (4.07 g, 26.4 mmol) in trichloromethane (10.2 mL) was added. The resulting mixture was stirred at 40° C. for 8 hours and extracted with dichloromethane (100 mL×3). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=10:1) to give the title compound 3d as pale yellow oil (1.9 g, 39.7%). The compound was characterized by the following spectroscopic data:

GC-MS m/z (EI): 139.1 (M-42); and
$^1$H NMR (400 MHz, DMSO-d$_6$) δ: 4.50 (d, 1H), 4.12 (m, 1H), 2.49 (m, 2H), 1.93 (m, 2H), 1.81 (m, 2H), 1.62 (m, 2H), 1.38 (m, 2H), 1.34 (s, 3H).

Step 4) (2r,3aR,5r,6aS)-5-amino-5-methyloctahydropentalen-2-ol

To a solution of (2r,3aR,5r,6aS)-5-azido-5-methyloctahydropentalen-2-ol 3d (1.23 g, 6.79 mmol) in methanol (41 mL) was added Pd/C (0.5 g, 10%, W/W=55%, Shaanxi kai da chemical reagent Co., Ltd) at rt. The mixture was stirred at rt under H$_2$ for 14 hours. The reaction mixture was filtered. The filtrate was concentrated in vacuo. The residue was purified by silica gel column chromatography (petroleum ether:ethyl acetate (V/V)=6:1) to give the title com- Step 1) (3aR,5s,6aS)-5-hydroxyhexahydropentalen-2(1H)-one To a solution (3as,6as)-tetrahydropentalene-2,5(1H,3H)-dione 3a (100 g, 0.725 mol) in ethyl acetate (88 mL) was added Lithium tri-tert-butoxyaluminum hydride (184 g, 0.725 mol, Beijing coupling technology Co., Ltd) with stirring. The mixture was stirred at rt for 15 hours and quenched with water (100 mL). The resulting mixture was filtered and the filtrate was extracted with ethyl acetate (200 mL × 3). The combined organic layers were dried over anhydrous sodium sulfate and concentrated in vacuo. The residue was purified by column chromatography (petroleum pound 3e as a pale yellow solid (0.5 g, 47.6%). The compound was characterized by the following spectroscopic data:

GC-MS m/z (EI): 155.1 (M); and
$^1$H NMR (400 MHz, DMSO-$d_6$) δ: 4.02 (m, 1H), 2.95 (brs, 2H), 2.50 (m, 2H), 1.86 (m, 2H), 1.66 (m, 2H), 1.38 (m, 2H), 1.22 (m, 2H), 1.14 (s, 3H).

Step 5) (2S,4S)-4-fluoro-1-(2-(((2r,3aR,5S,6aS)-5-hydroxy-2-methyloctahydropentalen-2-yl)amino)acetyl)pyrrolidine-2-carbonitrile To a solution of (2r,3aR,5r,6aS)-5-amino-5-methyloctahydropentalen-2-ol 3e (900 mg, 5.8 mmol) in N,N-dimethylformamide (20 mL) were added potassium iodide (960 mg, 5.8 mmol), potassium carbonate (800 mg, 5.8 mmol) and (2S,4S)-1-(2-chloroacetyl)-4-fluoropyrrolidine-2-carbonitrile 3f (1.1 g, 5.8 mmol). The mixture was stirred at rt for 8 hours and diluted with dichloromethane (100 mL). The resulting mixture was washed with saturated aqueous sodium chloride (200 mL x 3), dried over anhydrous sodium sulfate and concentrated in vacuo. The residue was purified by silica gel column chromatography (ethyl acetate) to give the title compound 3 as a yellow solid (750 mg, 41.8%). The compound was characterized by the following spectroscopic data:

MS m/z (ESI): 292.1 (M+1); and
$^1$H NMR (400 MHz, CDCl$_3$) δ: 4.75 (t, 1H), 4.30 (m, 1H), 3.61 (t, 1H), 3.45 (m, 1H), 3.32 (s, 2H), 2.63 (m, 2H), 2.29 (m, 2H), 2.16 (m, 2H), 2.06 (m, 2H), 1.95 (m, 2H), 1.86 (m, 2H), 1.25 (m, 2H), 1.18 (s, 3H).

Example 4

(2S,4S)-4-Fluoro-1-(2-(((2r,3aR,5R,6aS)-5-methoxy-2-methyloctahydropentalen-2-yl)amino)acetyl)pyrrolidine-2-carbonitrile

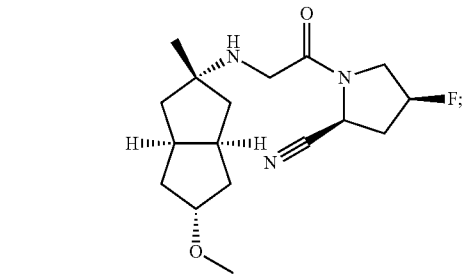

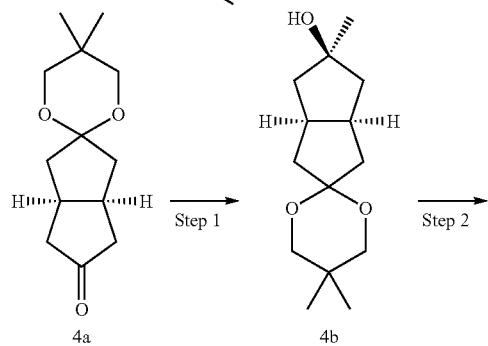

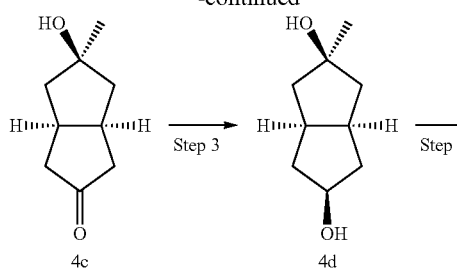

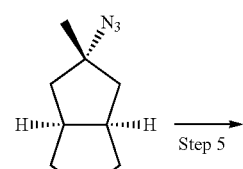

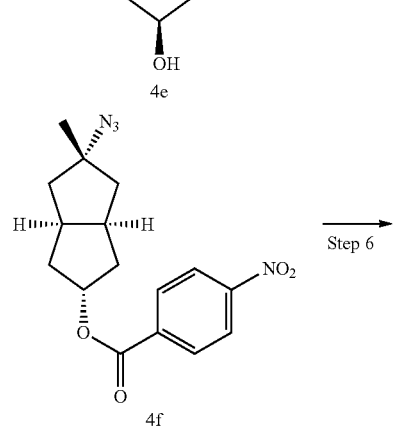

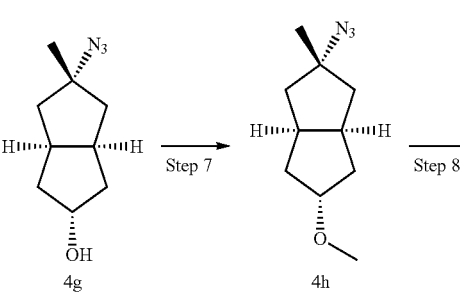

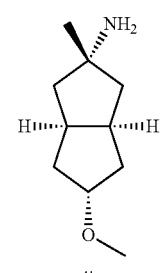

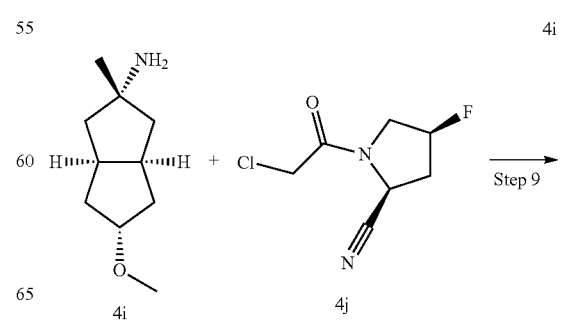

Step 1) (3a'R,5's,6a'S)-5,5,5'-trimethylhexahydro-1'H-spiro[[1,3]dioxane-2,2'-pentalen]-5'-ol To a solution of methylmagnesium bromide (120 mL, 3 M in ether, Shao yuan chemical technology (Shanghai) Co., Ltd) in tetrahydrofuran (250 mL) was added a solution of (3a'R,6a'S)-5,5-dimethyltetrahydro-1'H-spiro[[1,3]dioxane-2,2'-pentalen]-5'(3'H)-one 4a (28 g, 0.125 mol, prepared in Step 1 of example 1) in tetrahydroxfuran (250 mL) dropwise at 0° C. over a period of 1.5 hours. The mixture was stirred at rt for 30 min and then 70° C. for 15 hours. The reaction mixture was cooled to −10° C. and quenched with water. The resulting mixture was extracted with ethyl acetate (200 mL×4). The combined organic layers were washed with saturated aqueous sodium chloride (300 mL), dried over anhydrous sodium sulfate and concentrated in vacuo. The residue was purified by re-crystallization from hexane to give the title compound 4b as a white solid (23.15 g, 77.1%). The compound was characterized by the following spectroscopic data:

GC-MS m/z (EI): 240.2 (M); and
$^1$H NMR (400 MHz, CDCl$_3$) δ: 3.39 (s, 2H), 3.37 (s, 2H), 2.33 (m, 2H), 2.13 (m, 2H), 1.61 (m, 4H), 1.47 (m, 2H), 1.12 (s, 3H), 0.87 (s, 6H).

Step 2) (3aR,5s,6aS)-5-hydroxy-5-methylhexahydropentalen-2(1H)-one

A mixture of (3a'R,5's,6a'S)-5,5,5'-trimethylhexahydro-1'H-spiro[[1,3]dioxane-2,2'-pentalen]-5'-ol 4b (31 g, 0.130 mol) and p-toluenesulfonic acid monohydrate (4 g, 0.021 mol) in acetone-water mixtures (270 mL, V/V=25/2) was stirred at rt for 15 hours, and then sodium bicarbonate (6 g, 71.4 mmol) was added. The resulting mixture was stirred for 20 min and concentrated in vacuo. The residue was diluted with saturated aqueous sodium bicarbonate (50 mL). The mixture was extracted with dichloromethane (50 mL×3). The combined organic layers were dried over anhydrous sodium sulfate and concentrated in vacuo. The residue was purified by silica gel column chromatography (petroleum ether:ethyl acetate (V/V)=6:1) to give the title compound 4c as yellow liquid (19.13 g, 95.4%). The compound was characterized by the following spectroscopic data:

GC-MS m/z (EI): 154.1 (M); and
$^1$H NMR (400 MHz, DMSO-d$_6$) δ: 2.89 (m, 2H), 2.52 (m, 2H), 2.26 (m, 2H), 1.98 (m, 2H), 1.65 (m, 2H), 1.57 (s, 1H), 1.36 (s, 3H).

Step 3) (2r,3aR,5s,6aS)-2-methyloctahydropentalene-2,5-diol

To a solution (3 aR,5s,6 aS)-5-hydroxy-5-methylhexahydropentalen-2 (1M-one 4c (19.13 g, 0.124 mol) in ethyl acetate (300 mL) was added Lithium tri-tert-butoxyaluminum hydride (41.0 g, 0.162 mol, Beijing coupling technology Co., Ltd) at 0° C. with stirring. The mixture was stirred at 0° C. for 20 min and then rt overnight. The reaction mixture was cooled to 0° C. and quenched with saturated aqueous ammonium chloride (80 mL). The resulting mixture was filtered through a Celite pad, and the filter cake was wash with ethyl acetate (200 mL×3). The filtrate was partitioned. The combined organic layer was dried over anhydrous sodium sulfate and concentrated in vacuo to give the title compound 4d as white solid (19.0 g, 98.1%). The compound was characterized by the following spectroscopic data:

GC-MS m/z (EI): 156.2 (M); and
$^1$H NMR (400 MHz, DMSO-d$_6$) δ: 4.59 (d, 1H), 4.39 (s, 1H), 3.94 (m, 1H), 2.26 (m, 2H), 1.88 (m, 2H), 1.66 (m, 2H), 1.57 (m, 2H), 1.39 (m, 2H), 1.10 (s, 3H).

Step 4) (2r,3aR,5r,6aS)-5-azido-5-methyloctahydropentalen-2-ol

To a sulfuric acid solution (19.6 mL, 9.27 M) was added sodium azide (2.56 g, 39.4 mmol, Tianjin tian da chemical reagent Co., Ltd) at 0° C. with stirring. The mixture was stirred at rt for 30 min and a solution of (2r,3aR,5s,6aS)-2-methyloctahydropentalene-2,5-diol 4d (4.1 g, 26.3 mmol) in trichloromethane (50 mL) was added. The resulting mixture was stirred at 40° C. for 8 hours and cooled to 0° C. in an ice-water bath. The resulting mixture was extracted with dichloromethane (100 mL×3). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=10:1) to give the title compound 4e as pale yellow oil (1.9 g, 39.8%). The compound was characterized by the following spectroscopic data:

GC-MS m/z (EI): 139.1 (M-42); and
$^1$H NMR (400 MHz, DMSO-d$_6$) δ: 4.50 (d, 1H), 4.12 (m, 1H), 2.49 (m, 2H), 1.93 (m, 2H), 1.81 (m, 2H), 1.62 (m, 2H), 1.38 (m, 2H), 1.34 (s, 3H).

Step 5) (2s,3aR,5r,6aS)-5-azido-5-methyloctahydropentalen-2-yl 4-nitrobenzoate To a solution of (2r,3aR,5r,6aS)-5-azido-5-methyloctahydropentalen-2-ol 4e (6.21 g, 34.3 mmol), p-nitrobenzoic acid (22.9 g, 137 mmol) and triphenylphosphine (35.9 g, 137 mmol, Shanghai hongrui chemical technology Co., Ltd) in tetrahydrofuran (500 mL) was added diisopropyl azodicarboxylate (27.7 g, 137 mmol, Shanghai hongrui chemical technology Co., Ltd) with stirring, while keeping the reaction temperature below 10° C. The resulting mixture was stirred at rt overnight and concentrated in vacuo. The residue was diluted with dichloromethane (300 mL). The mixture was washed with saturated aqueous sodium chloride (100 mL), dried over anhydrous sodium sulfate and concentrated in vacuo. The residue was purified by silica gel column chromatography (petroleum ether:ethyl acetate (V/V)=12:1) to give the title compound 4f as a yellow solid (6.82 g, 60.2%). The compound was characterized by the following spectroscopic data:

MS m/z (ESI): 331.1 (M+1); and
$^1$H NMR (400 MHz, CDCl$_3$) δ: 8.35 (d, 2H), 8.18 (d, 2H), 5.48 (m, 1H), 2.82 (m, 2H), 2.04 (m, 4H), 1.83 (m, 2H), 1.45 (m, 2H), 1.40 (s, 3H).

Step 6) (2s,3aR,5r,6aS)-5-azido-5-methyloctahydro-pentalen-2-ol

To a solution of (2s,3aR,5r,6aS)-5-azido-5-methyloctahydropentalen-2-yl 4-nitrobenzoate 4f (6.72 g, 20.3 mmol) in MeOH-DCM mixtures (100 mL, V/V=3:1) was added potassium carbonate (3.09 g, 22.4 mmol). The mixture was stirred at rt for 2 hours and filtered. The filtrate was concentrated in vacuo. The residue was purified by silica gel column chromatography (petroleum ether:ethyl acetate (V/V)=6:1) to give the title compound 4g as colorless oil (2.76 g, 75.0%). The compound was characterized by the following spectroscopic data:

GC-MS m/z (EI): 181.1 (M); and
$^1$H NMR (400 MHz, CDCl$_3$) δ: 4.34 (m, 1H), 2.77 (m, 2H), 2.04 (m, 2H), 1.81 (m, 2H), 1.71 (m, 2H), 1.61 (m, 2H), 1.39 (s, 3H).

Step 7) (2r,3aR,5s,6aS)-2-azido-5-methoxy-2-methyloctahydropentalene

To a solution of (2s,3aR,5r,6aS)-5-azido-5-methyloctahydropentalen-2-ol 4g (2.76 g, 15.2 mmol) in tetrahydrofuran (100 mL) was added lithium bis(trimethylsilyl)amide (30.5 mL, 30.5 mmol, 1 M in tetrahydrofuran, Shanghai jingchun industrial Co., Ltd) at −10° C. over a period of 30 min. The resulting mixture was stirred at −10° C. for 30 min, and iodomethane (8.66 g, 60.9 mmol) was added. The mixture was allowed to warm up to rt and stirred overnight. The mixture was cooled to −10° C. and quenched with saturated aqueous ammonium chloride (100 mL). The resulting mixture was extracted with dichloromethane (100 mL×3). The combined organic layers were dried over anhydrous sodium sulfate and concentrated in vacuo. The residue was purified by silica gel column chromatography (petroleum ether: ethyl acetate (V/V)=50:1) to give the title compound 4h as amber oil (2.18 g, 73.4%). The compound was characterized by the following spectroscopic data:

$^1$H NMR (400 MHz, CDCl$_3$) δ: 3.76 (m, 1H), 3.29 (s, 3H), 3.19 (m, 2H), 2.78 (m, 2H), 2.51 (m, 2H), 1.81 (m, 2H), 1.75 (m, 2H), 1.66 (s, 3H).

Step 8) (2r,3aR,5s,6aS)-5-methoxy-2-methyloctahydropentalen-2-amine

To a solution of (2r,3aR,5s,6aS)-2-azido-5-methoxy-2-methyloctahydropentalene 4h (2.18 g, 11.2 mmol) in methanol (100 mL) was added Pd/C (0.80 g, 10%, W/W=55%, Shaanxi kai da chemical reagent Co., Ltd) at rt. The mixture was stirred under H$_2$ for 14 hours. The reaction mixture was filtered. The filtrate was concentrated in vacuo. The residue was purified by silica gel column chromatography (dichloromethane:methanol (V/V)=20:1) to give the title compound 4i as colorless oil (1.20 g, 63.2%). The compound was characterized by the following spectroscopic data:

MS m/z (ESI): 170.2 (M+1); and
$^1$H NMR (400 MHz, CDCl$_3$) δ: 3.79 (m, 1H), 3.24 (s, 3H), 2.68 (m, 2H), 1.69 (m, 4H), 1.51 (m, 4H), 1.18 (s, 3H).

Step 9) (2S,4S)-4-fluoro-1-(2-(((2r,3aR,5R,6aS)-5-methoxy-2-methyloctahydropentalen-2-yl)amino) acetyl)pyrrolidine-2-carbonitrile To a solution of (2r,3aR,5s,6aS)-5-methoxy-2-methyloctahydropentalen-2-amine 4i (1.50 g, 8.87 mmol) in N,N-dimethylformamide-methanol mixtures (100 mL, V/V=3:1) were added (S)-1-(2-chloroacetyl)pyrrolidine-2-carbonitrile 4j (1.86 g, 9.76 mmol, prepared in Step 6 of example 2), potassium iodide (1.62 g, 9.76 mmol) and potassium carbonate (1.35 g, 9.76 mmol). The mixture was stirred at rt for 14 hours and then concentrated in vacuo. The residue was dissolved in dichloromethane (80 mL). The solution was washed with saturated aqueous sodium chloride (80 mL), dried over anhydrous sodium sulfate and concentrated in vacuo. The residue was purified by silica gel column chromatography (dichloromethane:methanol (V/V)=20:1) to give the title compound 4 as a yellow solid (0.87 g, 30.3%). The compound was characterized by the following spectroscopic data:

MS m/z (ESI): 324.2 (M+1); and
$^1$H NMR (400 MHz, CDCl$_3$) δ: 5.22-5.49 (m, 1H), 4.94 (d, 1H), 3.87 (m, 2H), 3.72 (m, 1H), 3.33 (s, 2H), 3.29 (s, 3H), 2.71 (m, 2H), 2.63 (m, 1H), 2.24 (m, 1H), 1.90 (m, 4H), 1.73 (m, 2H), 1.59 (m, 2H), 1.18 (s, 3H).

Example 5

(5)-1-(2-(((2r,3aR,5S,6aS)-5-Hydroxy-2-methyloctahydropentalen-2-yl)amino)acetyl) pyrrolidine-2-carbonitrile

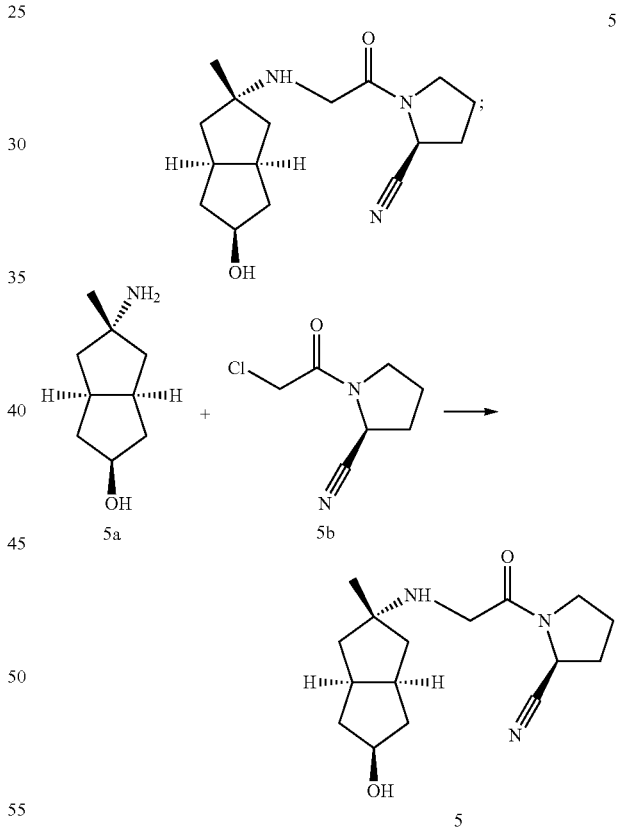

To a solution of (2r,3aR,5r,6aS)-5-amino-5-methyloctahydropentalen-2-ol 5a (0.40 g, 2.58 mmol, prepared in Step 4 of example 3) in N,N-dimethylformamide (20 mL) were added (S)-1-(2-chloroacetyl)pyrrolidine-2-carbonitrile 5b (0.45 g, 2.58 mmol), potassium iodide (0.43 g, 2.58 mmol) and potassium carbonate (0.36 g, 2.58 mmol). The mixture was stirred at rt overnight and quenched with water (50 mL). The resulting mixture was extracted with dichloromethane (50 mL×3). The combined organic layers were washed with saturated aqueous sodium chloride (100 mL×3), dried over anhydrous sodium sulfate and concentrated in vacuo. The residue was purified by silica gel column chromatography (dichloromethane:methanol (V/V)=6:1) to give the title compound 5 as pale yellow oil (0.5 g, 66.7%). The compound was characterized by the following spectroscopic data:

MS m/z (ESI): 292.1 (M+1); and $^1$H NMR (400 MHz, CDCl$_3$) δ: 4.75 (t, 1H), 4.30 (m, 1H), 3.61 (t, 1H), 3.45 (m, 1H), 3.32 (s, 2H), 2.63 (m, 2H), 2.29 (m, 2H), 2.16 (m, 2H), 2.06 (m, 2H), 1.95 (m, 2H), 1.86 (m, 2H), 1.25 (m, 2H), 1.18 (s, 3H).

Example 6

(S)-1-(2-(((2r,3aR,5S,6aS)-5-Ethoxy-2-methyloctahydropentalen-2-yl)amino)acetyl)pyrrolidine-2-carbonitrile

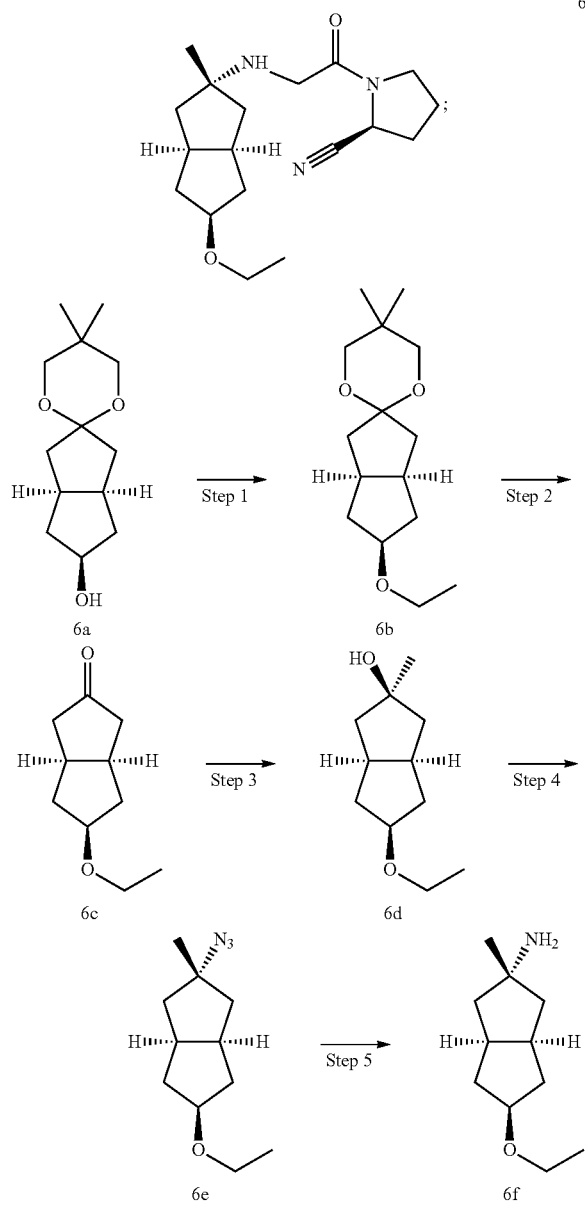

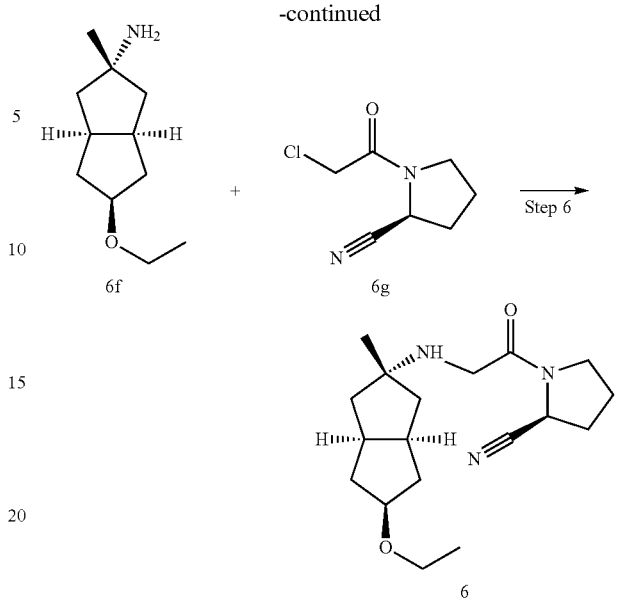

Step 1) (3a'R,5's,6a'S)-5'-ethoxy-5,5-dimethylhexahydro-1'H-spiro[[1,3]dioxane-2,2'-pentalene]

To a solution of (3a'R,5's,6a'S)-5,5-dimethylhexahydro-1'H-spiro[[1,3]dioxane-2,2'-pentalen]-5'-ol 6a (16.78 g, 0.074 mol) in tetrahydrofuran was added sodium hydride (3.55 g, 0.148 mol, 60%, Tianjin da mao chemical reagent company). The mixture was stirred at rt for 1 hour and ethyl iodide (23.08 g, 0.148 mol, Aladdin) was added. The resulting mixture was refluxed for 3 hours. The reaction mixture was cooled to rt and quenched with ice water (10 mL). The resulting mixture was extracted with ethyl acetate (100 mL×3). The combined organic layers were washed with saturated aqueous sodium chloride (50 mL×3), dried over anhydrous sodium sulfate and concentrated in vacuo. The residue was purified by silica gel column chromatography (petroleum ether:ethyl acetate (V/V)=10:1) to give the title compound 6b as yellow oil (18.2 g, 96.7%). The compound was characterized by the following spectroscopic data:

$^1$H NMR (400 MHz, CDCl$_3$) δ: 3.79 (m, 1H), 3.46 (m, 4H), 3.43 (m, 2H), 2.38 (m, 2H), 2.23 (m, 2H), 2.01 (m, 2H), 1.69 (m, 2H), 1.14 (m, 2H), 1.15 (t, 3H), 0.95 (s, 6H).

Step 2) (3aR,5s,6aS)-5-ethoxyhexahydropentalen-2(1H)-one

To a mixture of (3a'R,5's,6a'S)-5'-ethoxy-5,5-dimethylhexahydro-1'H-spiro[[1,3]dioxane-2,2'-pentalene] 6b (9.54 g, 37.5 mmol) in acetone (80 mL) were added water (1 mL) and p-toluenesulfonic acid monohydrate (0.49 g, 2.6 mmol). The mixture was stirred at rt for 12 hours and saturated aqueous sodium carbonate (100 mL) was added. The resulting mixture was extracted with ethyl acetate (80 mL×3). The combined organic layers were dried over anhydrous sodium sulfate and concentrated in vacuo. The residue was purified by silica gel column chromatography (petroleum ether:ethyl acetate (V/V)=15:1) to give the title compound 6c as yellow oil (4.17 g, 66.1%). The compound was characterized by the following spectroscopic data:

$^1$H NMR (400 MHz, CDCl$_3$) δ: 3.95 (m, 1H), 3.37 (m, 2H), 2.73 (m, 2H), 2.45 (m, 2H), 2.22 (m, 2H), 2.05 (m, 2H), 1.61 (m, 2H), 1.11 (t, 3H).

Step 3) (2r,3aR,5s,6aS)-5-ethoxy-2-methyloctahydropentalen-2-ol

To a solution of methylmagnesium bromide (112.7 mL, 3 M in ether) in tetrahydrofuran (100 mL) was added a solution of (3aR,5s,6aS)-5-ethoxyhexahydropentalen-2 (1H)-one 6c (19.0 g, 0.113 mmol) in tetrahydroxfuran (100 mL) at 0° C. over a period of 30 min. The mixture was allowed to warm up to rt, and refluxed for 9 hours. The reaction mixture was cooled to 0° C., quenched with saturated aqueous ammonium chloride (30 mL), and washed with saturated aqueous sodium chloride (80 mL×3). The organic layer was dried over anhydrous sodium sulfate and concentrated in vacuo. The residue was purified by silica gel column chromatography (petroleum ether:ethyl acetate (V/V)=9:1) to give the title compound 6d as yellow oil (12.4 g, 59.3%). The compound was characterized by the following spectroscopic data:

$^1$H NMR (400 MHz, CDCl$_3$) δ: 3.87 (m, 1H), 3.60 (s, 1H), 3.44 (m, 2H), 2.49 (m, 2H), 2.00 (m, 4H), 1.71 (m, 4H), 1.25 (s, 3H), 1.20 (t, 3H).

Step 4) (2r,3aR,5r,6aS)-2-azido-5-ethoxy-2-methyloctahydropentalene

To a sulfuric acid solution (40 mL, 9.2 M) was added sodium azide (7.57 g, 0.116 mol) at 0° C. with stirring. The mixture was stirred at this temperature for 30 min and a solution of (2r,3aR,5s,6aS)-5-ethoxy-2-methyloctahydropentalen-2-ol 6c (10.72 g, 0.058 mol) in trichloromethane (150 mL) was added. The resulting mixture was stirred at 40° C. for 6.5 hours and quenched with water. The resulting mixture was extracted with dichloromethane (50 mL×2). The combined organic layers were washed with saturated aqueous sodium chloride (50 mL×3), dried over anhydrous sodium sulfate and concentrated in vacuo. The residue was purified by silica gel column chromatography (petroleum ether:ethyl acetate (V/V)=9:1) to give the title compound 6d as yellow oil (9.24 g, 76.1%). The compound was characterized by the following spectroscopic data:

$^1$H NMR (400 MHz, CDCl$_3$) δ: 3.87 (m, 1H), 3.41 (m, 2H), 2.61 (m, 2H), 2.02 (m, 4H), 1.53 (m, 4H), 1.37 (s, 3H), 1.14 (t, 3H).

Step 5) (2r,3aR,5r,6aS)-5-ethoxy-2-methyloctahydropentalen-2-amine

To a solution of (2r,3aR,5r,6aS)-2-azido-5-ethoxy-2-methyloctahydropentalene 6d (8.44 g, 0.04 mol) in methanol (80 mL) was added Pd/C (2 g, 10%, ~W/W=55%, Shaanxi kai da chemical reagent Co., Ltd). The mixture was stirred under H$_2$ overnight. The reaction mixture was filtered. The filtrate was concentrated in vacuo. The residue was purified by silica gel column chromatography (dichloromethane: methanol (V/V)=5:1) to give the title compound 6e as yellow oil (4.87 g, 66.4%). The compound was characterized by the following spectroscopic data:

$^1$H NMR (400 MHz, CDCl$_3$) δ: 3.89 (m, 1H), 3.44 (m, 2H), 2.58 (m, 2H), 1.99 (m, 2H), 1.76 (m, 2H), 1.48 (m, 6H), 1.23 (s, 3H), 1.16 (t, 3H).

Step 6) (S)-1-(2-(((2r,3aR,5S,6aS)-5-ethoxy-2-methyloctahydropentalen-2-yl)amino) acetyl) pyrrolidine-2-carbonitrile To a solution of (2r,3aR,5r,6aS)-5-ethoxy-2-methyloctahydropentalen-2-amine 6e (2.32 g, 12.68 mmol) in tetrahydrofuran (35 mL) were added (S)-1-(2-chloroacetyl)pyrrolidine-2-carbonitrile 6g (2.19 g, 12.68 mmol), potassium iodide (0.21g, 1.27 mmol) and potassium carbonate (7.01 g, 50.71 mmol). The mixture was stirred at rt overnight and diluted with ethyl acetate (100 mL). The resulting mixture was washed with saturated aqueous sodium chloride (50 mL×3), dried over anhydrous sodium sulfate and concentrated in vacuo. The residue was purified by silica gel column chromatography (dichloromethane:methanol (V/V)=40:1) to give the title compound 6 as yellow oil (0.98 g, 24.2%, HPLC: 99.0%). The compound was characterized by the following spectroscopic data:

$^1$H NMR (400 MHz, CDCl$_3$) δ: 4.76 (d, 1H), 3.87 (m, 1H), 3.61 (m, 1H), 3.42 (m, 4H), 3.31 (s, 2H), 2.59 (m, 2H), 2.27 (m, 2H), 2.19 (m, 2H), 1.91 (m, 4H), 1.47 (m, 4H), 1.18 (s, 3H), 1.16 (m, 3H).

Example 7

(2S,4S)-1-(2-(((2r,3aR,5S,6aS)-5-Ethoxy-2-methyloctahydropentalen-2-yl)amino)acetyl)-4-fluoropyrrolidine-2-carbonitrile

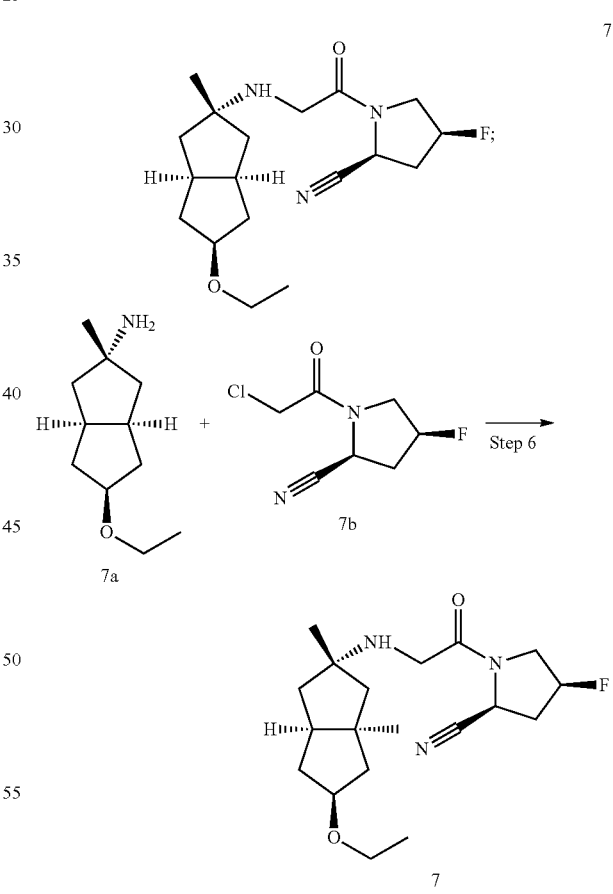

To a solution of (2r,3aR,5r,6aS)-5-ethoxy-2-methyloctahydropentalen-2-amine 7a (1.8 g, 9.83 mmol, prepared in Step 5 of example 6) in tetrahydrofuran (35 mL) were added (S)-1-(2-chloroacetyl)pyrrolidine-2-carbonitrile 7b (1.19 g, 9.83 mmol), potassium iodide (0.16 g, 9.83 mmol) and potassium carbonate (5.43 g, 39.3 mmol). The mixture was stirred at rt overnight and diluted with ethyl acetate (80 mL).

The resulting mixture was washed with saturated aqueous sodium chloride (80 mL×3), dried over anhydrous sodium sulfate and concentrated in vacuo. The residue was purified by silica gel column chromatography (dichloromethane:methanol (V/V)=30:1) to give the title compound 7 as yellow oil (1.27 g, 38.3%, HPLC: 98.5%). The compound was characterized by the following spectroscopic data:

MS m/z (ESI): 338.2 (M+1); and $^1$H NMR (400 MHz, CDCl$_3$) δ: 5.47 (m, 1H), 4.95 (m, 1H), 3.94 (m, 1H), 3.88 (m, 1H), 3.77 (m, 1H), 3.44 (m, 2H), 3.32 (m, 2H), 2.66 (m, 1H), 2.57 (m, 2H), 2.34 (m, 1H), 1.95 (m, 4H), 1.79 (s, 2H), 1.45 (m, 4H), 1.19 (s, 3H), 1.16 (t, 3H)

Example 8

(2S,4S)-1-(2-(((2r,3aR,5S,6aS)-5-(Cyclopropyl-methoxy)-2-methyloctahydropentalen-2-yl)amino)acetyl)-4-fluoropyrrolidine-2-carbonitrile

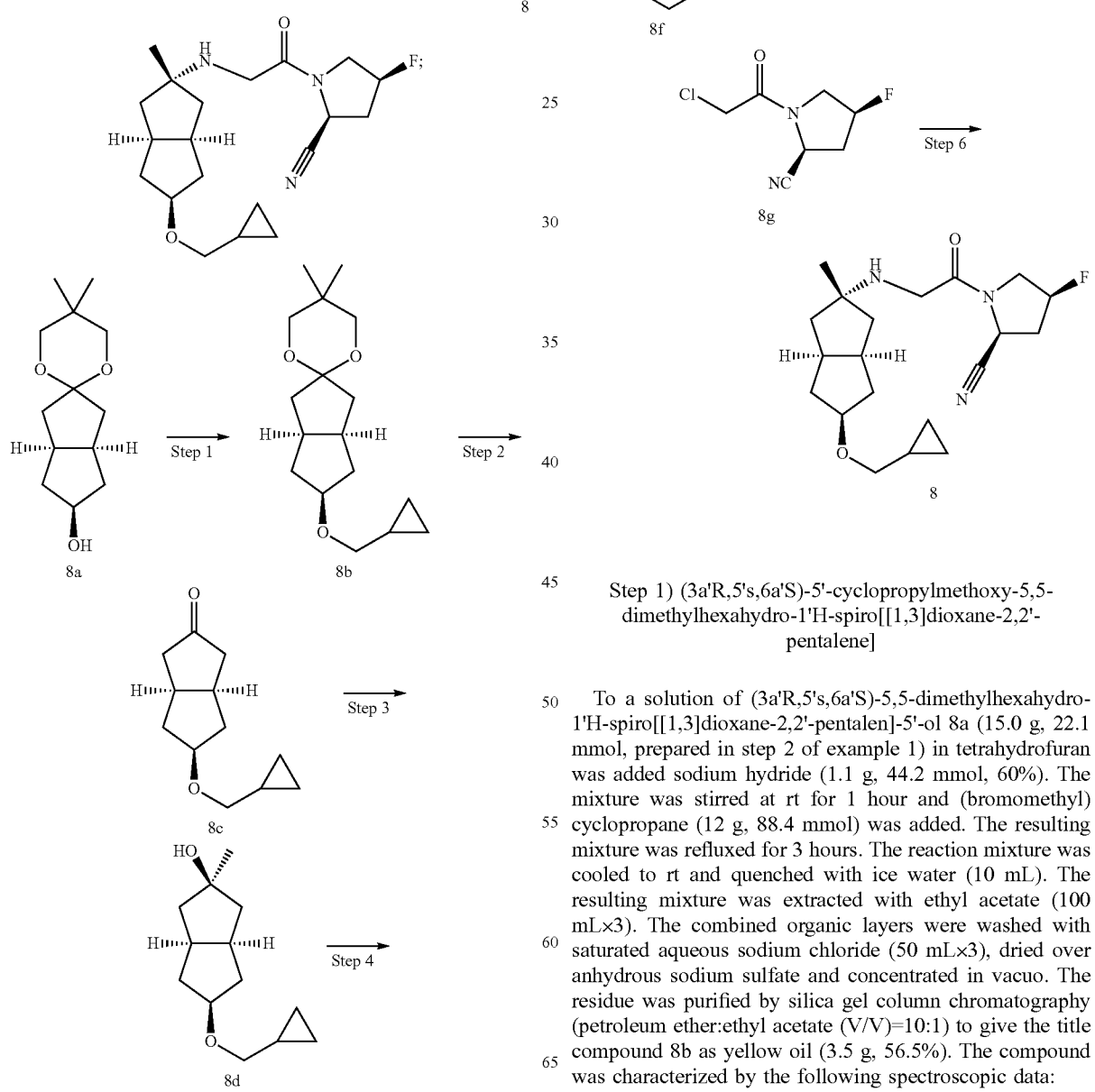

Step 1) (3a'R,5's,6a'S)-5'-cyclopropylmethoxy-5,5-dimethylhexahydro-1'H-spiro[[1,3]dioxane-2,2'-pentalene]

To a solution of (3a'R,5's,6a'S)-5,5-dimethylhexahydro-1'H-spiro[[1,3]dioxane-2,2'-pentalen]-5'-ol 8a (15.0 g, 22.1 mmol, prepared in step 2 of example 1) in tetrahydrofuran was added sodium hydride (1.1 g, 44.2 mmol, 60%). The mixture was stirred at rt for 1 hour and (bromomethyl)cyclopropane (12 g, 88.4 mmol) was added. The resulting mixture was refluxed for 3 hours. The reaction mixture was cooled to rt and quenched with ice water (10 mL). The resulting mixture was extracted with ethyl acetate (100 mL×3). The combined organic layers were washed with saturated aqueous sodium chloride (50 mL×3), dried over anhydrous sodium sulfate and concentrated in vacuo. The residue was purified by silica gel column chromatography (petroleum ether:ethyl acetate (V/V)=10:1) to give the title compound 8b as yellow oil (3.5 g, 56.5%). The compound was characterized by the following spectroscopic data:

MS m/z (ESI): 281.2 (M+1); and

¹H NMR (CDCl₃, 400 MHz) δ: 3.84 (m, 1H), 3.46 (m, 4H), 3.23 (d, 2H), 2.41 (m, 2H), 2.27 (m, 2H), 2.06 (m, 2H), 1.73 (m, 2H), 1.50 (m, 2H), 1.03 (m, 1H), 0.95 (s, 6H), 0.51 (m, 2H), 0.18 (m, 2H).

Step 2) (3aR,5s,6aS)-5-cyclopropylmethoxyhexahydropentalen-2(1H)-one

To a mixture of (3a'R,5's,6a'S)-5'-cyclopropylmethoxy-5,5-dimethylhexahydro-1'H-spiro[[1,3]dioxane-2,2'-pentalene] 8b (3 g, 10.7 mmol) in acetone (30 mL) were added water (1 mL) and p-toluenesulfonic acid monohydrate (0.14 g, 0.75 mmol). The mixture was stirred at rt for 12 hours and sodium carbonate (0.55 g, 5.19 mmol) was added. The resulting mixture was extracted with ethyl acetate (80 mL). The organic layer was washed with saturated aqueous sodium chloride (30 mL×3), dried over anhydrous sodium sulfate and concentrated in vacuo. The residue was purified by silica gel column chromatography (petroleum ether:ethyl acetate (V/V)=15:1) to give the title compound 8c as yellow oil (1.7 g, 81.7%). The compound was characterized by the following spectroscopic data:

MS m/z (ESI): 195.2 (M+1); and
¹H NMR (400 MHz, CDCl₃) δ: 3.99 (m, 1H), 3.20 (m, 2H), 2.74 (m, 2H), 2.47 (m, 2H), 2.26 (m, 2H), 2.10 (m, 2H), 1.65 (m, 2H), 0.99 (m, 1H), 0.51 (m, 2H), 0.16 (m, 2H).

Step 3) (2r,3aR,5s,6aS)-5-cyclopropylmethoxy-2-methyloctahydropentalen-2-ol

To a solution of methylmagnesium bromide (4.16 mL, 13.1 mmol, 3 M in ether) in tetrahydrofuran (10 mL) was added a solution of (3aR,5s,6aS)-5-cyclopropylmethoxyhexahydropentalen-2(1H)-one 8c (1.7 g, 8.76 mmol) in tetrahydrofuran (10 mL) at 0° C. The mixture was allowed to warm up to rt, and refluxed for 9 hours. The reaction mixture was cooled to 0° C. and quenched with saturated aqueous ammonium chloride (10 mL), and 40 mL of ethyl acetate was added. The resulting mixture was washed with saturated aqueous sodium chloride (30 mL×3), dried over anhydrous sodium sulfate and concentrated in vacuo. The residue was purified by silica gel column chromatography (petroleum ether:ethyl acetate (V/V)=9:1) to give the title compound 8d as yellow oil (1.3 g, 70.7%). The compound was characterized by the following spectroscopic data:

MS m/z (ESI): 233.3 (M+23); and
¹H NMR (400 MHz, CDCl₃) δ: 3.92 (m, 1H), 3.33 (s, 1H), 3.25 (m, 2H), 2.53 (m, 2H), 2.03 (m, 4H), 1.76 (m, 4H), 1.26 (s, 3H), 1.02 (m, 1H), 0.53 (m, 2H), 0.19 (m, 2H).

Step 4) (2r,3aR,5r,6aS)-2-azido-5-cyclopropylmethoxy-2-methyloctahydropentalene

To a sulfuric acid solution (5.6 mL, 0.052 mmol, 9.2 M) was added sodium azide (0.76 g, 15.64 mmol, Tianjin tian da chemical reagent Co., Ltd) at 0° C. with stirring. The mixture was stirred at 0° C. for 30 min and a solution of (2r,3aR,5s,6aS)-5-cyclopropylmethoxy-2-methyloctahydropentalen-2-ol 8d (1.63 g, 7.76 mol) in trichloromethane (30 mL) was added. The resulting mixture was stirred at 40° C. for 6.5 hours and quenched with water. The resulting mixture was extracted with dichloromethane (50 mL×3). The combined organic layers were washed with saturated aqueous sodium chloride (50 mL×3), dried over anhydrous sodium sulfate and concentrated in vacuo. The residue was purified by silica gel column chromatography (petroleum ether:ethyl acetate (V/V)=9:1) to give the title compound 8e as yellow oil (1.23 g, 67.2%). The compound was characterized by the following spectroscopic data:

¹H NMR (400 MHz, CDCl₃) δ: 3.93 (m, 1H), 3.21 (m, 2H), 2.62 (m, 2H), 2.04 (m, 2H), 1.88 (m, 2H), 1.56 (m, 4H), 1.38 (s, 3H), 1.00 (m, 1H), 0.51 (m, 2H), 0.19 (m, 2H).

Step 5) (2r,3aR,5r,6aS)-5-cyclopropylmethoxy-2-methyloctahydropentalen-2-amine

To a solution of (2r,3aR,5r,6aS)-2-azido-5-cyclopropylmethoxy-2-methyloctahydropentalene 8e (1.23 g, 5.23 mmol) in methanol (25 mL) was added Pd/C (0.5 g, 10%, W/W=55%, Shaanxi kai da chemical reagent Co., Ltd). The mixture was stirred under H₂ for 14 hours. The reaction mixture was filtered. The filtrate was concentrated in vacuo. The residue was purified by silica gel column chromatography (dichloromethane:methanol (V/V)=5:2) to give the title compound 8f as yellow oil (0.78 g, 72.2%). The compound was characterized by the following spectroscopic data:

MS m/z (ESI): 210.2 (M+1); and
¹H NMR (400 MHz, CDCl₃) δ: 8.15 (brs, 2H), 3.93 (m, 1H), 3.17 (m, 2H), 2.28 (m, 2H), 2.02 (m, 2H), 1.84 (m, 2H), 1.68 (m, 2H), 1.53 (s, 3H), 1.44 (m, 2H), 0.97 (m, 1H), 0.51 (m, 2H), 0.16 (m, 2H).

Step 6) (S)-1-(2-(((2r,3aR,5S,6aS)-5-cyclopropylmethoxy-2-methyloctahydropentalen-2-yl)amino)acetyl)pyrrolidine-2-carbonitrile To a solution of (2r,3aR,5r,6aS)-5-cyclopropylmethoxy-2-methyloctahydropentalen-2-amine 8f (1.0 g, 4.778 mmol) in tetrahydrofuran (35 mL) were added (2S,4S)-1-(2-chloroacetyl)-4-fluoropyrrolidine-2-carbonitrile 8g (0.92 g, 4.826 mmol), potassium iodide (0.08 g, 0.479 mmol) and potassium carbonate (3.3 g, 23.885 mmol). The mixture was stirred at rt for 14 hours and filtered. The filtrate was diluted with ethyl acetate (50 mL). The resulting mixture was washed with saturated aqueous sodium chloride (50 mL×3), dried over anhydrous sodium sulfate and concentrated in vacuo. The residue was purified by silica gel column chromatography (dichloromethane:methanol (V/V)=40:1) to give the title compound 8 as yellow oil (0.98 g, 56.3%, HPLC: 95.5%). The compound was characterized by the following spectroscopic data:

MS m/z (ESI): 364.2 (M+1); and
¹H NMR (400 MHz, CDCl₃) δ: 5.48 (m, 1H), 4.95 (m, 1H), 3.91 (m, 1H), 3.88 (m, 1H), 3.51 (m, 1H), 3.32 (m, 1H), 3.22 (m, 2H), 2.67 (m, 1H), 2.63 (m, 2H), 2.35 (m, 1H), 1.94 (m, 4H), 1.65 (s, 2H), 1.44 (m, 4H), 1.21 (s, 3H), 0.87 (m, 1H), 0.51 (m, 2H), 0.17 (m, 2H).

Example 9

(2S,4S)-4-Fluoro-1-(2-(((2r,3aR,5R,6aS)-5-hydroxy-2-methyloctahydropentalen-2-yl)amino)acetyl)pyrrolidine-2-carbonitrile

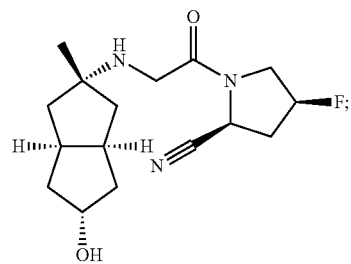

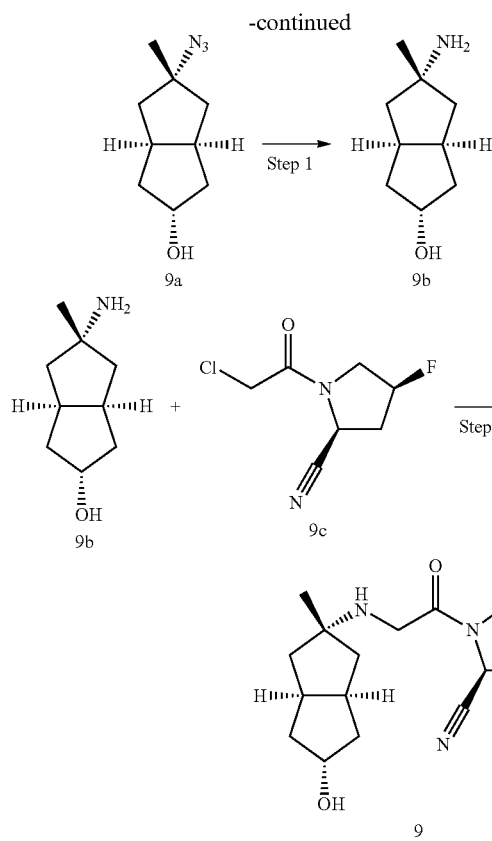

Step 1) (2s,3aR,5r,6aS)-5-amino-5-methyloctahydropentalen-2-ol

To a solution of (2s,3aR,5r,6aS)-5-azido-5-methyloctahydropentalen-2-ol 9a (1.23 g, 6.79 mmol, prepared in step 6 of example 4) in methanol (100 mL) was added Pd/C (0.5 g, 10%, W/W=55%, Shaanxi kai da chemical reagent Co., Ltd). The mixture was stirred under $H_2$ for 14 hours. The reaction mixture was filtered. The filtrate was concentrated in vacuo. The residue was purified by silica gel column chromatography (ethyl acetate:methanol (V/V)=10:1) to give the title compound 9b as pale yellow oil (0.67 g, 63.5%, HPLC: 97.0%). The compound was characterized by the following spectroscopic data:

$^1$H NMR (400 MHz, $CD_3OD$-$d_4$) δ: 4.29 (m, 1H), 2.80 (m, 2H), 1.81 (m, 2H), 1.68 (m, 2H), 1.56 (m, 2H), 1.24 (m, 2H), 1.20 (s, 3H).

Step 2) (2S,4S)-4-fluoro-1-(2-(((2r,3aR,5R,6aS)-5-hydroxy-2-methyloctahydropentalen-2-yl)amino)acetyl)pyrrolidine-2-carbonitrile To a solution of (2s,3aR,5r,6aS)-5-amino-5-methyloctahydropentalen-2-ol 9b (1.52 g, 9.68 mmol) in N,N-dimethylformamide (100 mL) were added potassium iodide (0.16 g, 0.97 mmol), potassium carbonate (6.72 g, 48.39 mmol) and (S)-1-(2-chloroacetyl)pyrrolidine-2-carbonitrile 9c (1.52 g, 9.68 mmol). The mixture was stirred at rt for 14 hours and filtered. The filtrate was concentrated in vacuo. The residue was dissolved in dichloromethane (100 mL). The solution was washed with saturated aqueous sodium chloride (100 mL), dried over anhydrous sodium sulfate and concentrated in vacuo. The residue was purified by silica gel column chromatography (dichloromethane:methanol (V/V)=20:1) to give the title compound 9 as a yellow solid (1.71 g, 57.2%). The compound was characterized by the following spectroscopic data:

MS m/z (ESI): 310.2 (M+1); and $^1$H NMR (400 MHz, DMSO-$d_6$) δ: 5.55 (m, 1H), 4.96 (d, 1H), 4.37 (m, 1H), 4.16 (m, 1H), 4.09 (m, 1H), 3.97 (dd, 1H), 3.79 (m, 1H), 3.41 (m, 1H), 3.17 (m, 2H), 2.61 (m, 2H), 1.88 (m, 2H), 1.50 (m, 2H), 1.45 (m, 2H), 1.24 (m, 1H), 1.04 (s, 3H), 1.01 (m, 2H).

Example 10

(S)-1-(2-(((2r,3aR,5R,6aS)-5-methoxy-2-methyloctahydropentalen-2-yl)amino)acetyl) pyrrolidine-2-carbonitrile

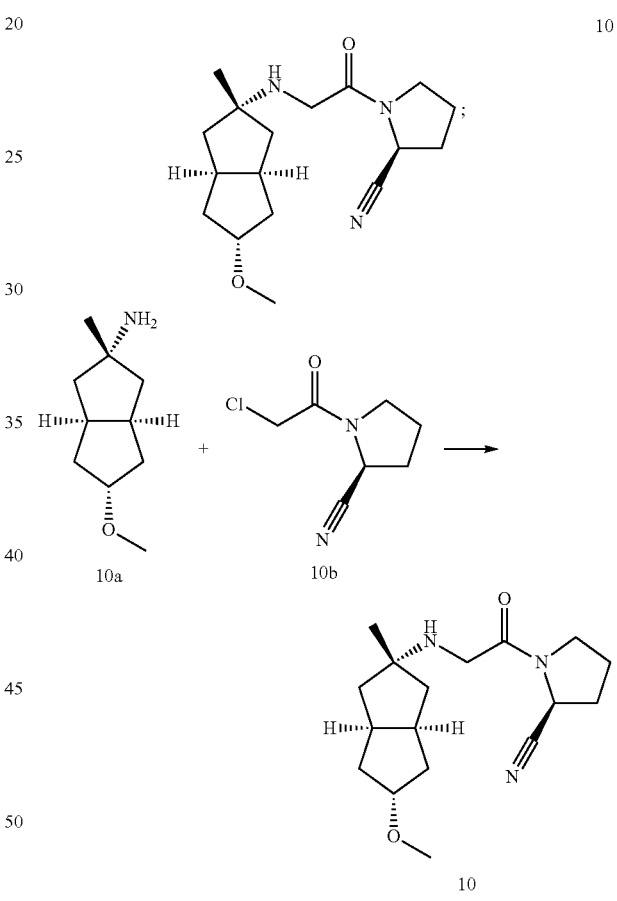

To a solution of (2r,3aR,5s,6aS)-5-methoxy-2-methyloctahydropentalen-2-amine 10a (1.20 g, 7.10 mmol, prepared in step 8 of example 4) in tetrahydrofuran (50 mL) were added (S)-1-(2-chloroacetyl)pyrrolidine-2-carbonitrile 10b (1.35 g, 7.81 mmol), potassium iodide (118 mg, 0.710 mmol) and potassium carbonate (4.90 g, 35.5 mmol). The mixture was stirred at rt for 2 days and concentrated in vacuo. The residue was dissolved in dichloromethane (50 mL). The solution was washed with saturated aqueous sodium chloride (50 mL), dried over anhydrous sodium sulfate and concentrated in vacuo. The residue was purified by silica gel column chromatography (dichloromethane:methanol (V/V)=20:1) to give the title compound 10 as a yellow solid (1.12 g, 51.6%, HPLC: 98.9%). The compound was characterized by the following spectroscopic data:

MS m/z (ESI): 306.3 (M+1); and $^1$H NMR (400 MHz, DMSO-$d_6$) δ: 4.71 (m, 1H), 3.82 (m, 1H), 3.58 (m, 1H), 3.38 (m, 1H), 3.24 (m, 2H), 3.17 (s, 3H), 2.58 (m, 2H), 2.12 (m, 2H), 2.01 (m, 2H), 1.86 (m, 2H), 1.60 (m, 2H), 1.52 (m, 2H), 1.07 (s, 3H), 0.98 (m, 2H).

Example 11

(2S,4S)-4-Fluoro-1-(2-(((3a'S,5'R,6a'R)-5'-methoxy-hexahydro-2'H-spiro[cyclopropane-1,1'-pentalen]-2'-yl)amino)acetyl)pyrrolidine-2-carbonitrile

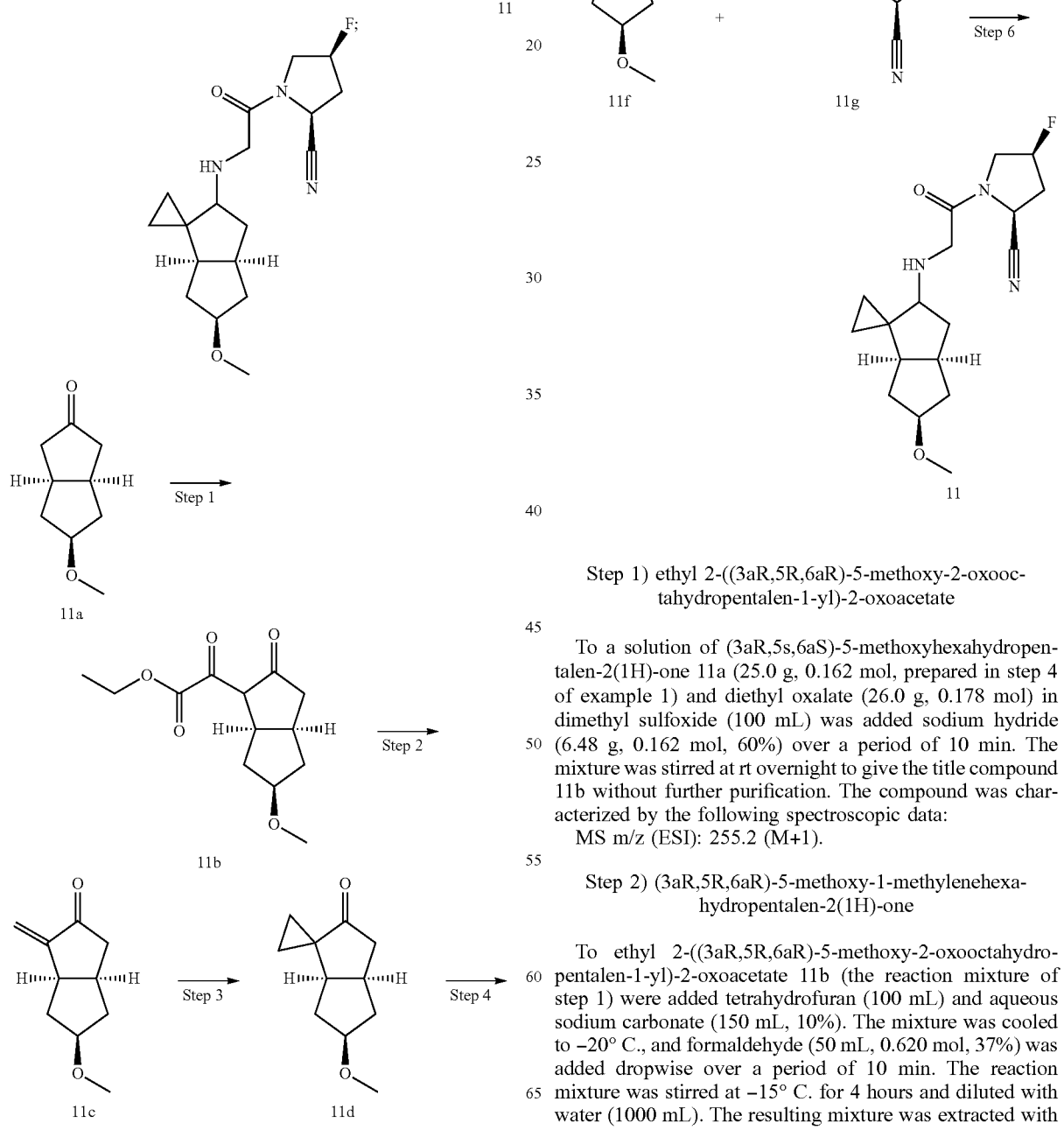

Step 1) ethyl 2-((3aR,5R,6aR)-5-methoxy-2-oxooc-tahydropentalen-1-yl)-2-oxoacetate To a solution of (3aR,5s,6aS)-5-methoxyhexahydropentalen-2(1H)-one 11a (25.0 g, 0.162 mol, prepared in step 4 of example 1) and diethyl oxalate (26.0 g, 0.178 mol) in dimethyl sulfoxide (100 mL) was added sodium hydride (6.48 g, 0.162 mol, 60%) over a period of 10 min. The mixture was stirred at rt overnight to give the title compound 11b without further purification. The compound was characterized by the following spectroscopic data:

MS m/z (ESI): 255.2 (M+1).

Step 2) (3aR,5R,6aR)-5-methoxy-1-methylenehexa-hydropentalen-2(1H)-one

To ethyl 2-((3aR,5R,6aR)-5-methoxy-2-oxooctahydro-pentalen-1-yl)-2-oxoacetate 11b (the reaction mixture of step 1) were added tetrahydrofuran (100 mL) and aqueous sodium carbonate (150 mL, 10%). The mixture was cooled to −20° C., and formaldehyde (50 mL, 0.620 mol, 37%) was added dropwise over a period of 10 min. The reaction mixture was stirred at −15° C. for 4 hours and diluted with water (1000 mL). The resulting mixture was extracted with ethyl acetate (400 mL×2). The combined organic layers were washed with water (200 mL) and saturated aqueous sodium chloride (200 mL), dried over anhydrous sodium sulfate and concentrated in vacuo. The residue was purified by silica gel column chromatography (petroleum ether:ethyl acetate (V/V)=95:5) to give the title compound 11c as yellow oil (13.8 g, yield of the two steps: 51.2%). The compound was characterized by the following spectroscopic data:

MS m/z (ESI): 167.2 (M+1).

Step 3) (3a'R,5'R,6a'R)-5'-methoxyhexahydro-2'H-spiro[cyclopropane-1,1'-pentalen]-2'-one To a suspension of sodium hydride (3.39 g, 84.8 mmol) in dimethyl sulfoxide (60 mL) was added trimethylsulfoxonium iodide (20.3 g, 92.5 mmol). The mixture was stirred at rt for 30 min, and a solution of (3aR,5R,6aR)-5-methoxy-1-methylenehexahydropentalen-2(1H)-one 11c (12.8 g, 77.1 mmol) in dimethyl sulfoxide (20 mL) was added. The reaction mixture was stirred at rt for 2 hours and quenched with ice water (500 mL). The resulting mixture was extracted with methyl tertiary butyl ether (300 mL×2). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=10:1) to give the title compound 11d as yellow oil (3.8 g, 27.3%). The compound was characterized by the following spectroscopic data:

MS m/z (ESI): 181.3 (M+1); and
$^1$H NMR (400 MHz, CDCl$_3$) δ: 3.86 (m, 1H), 3.25 (s, 3H), 2.83 (m, 1H), 2.65 (m, 1H), 2.56 (m, 1H), 2.33 (m, 1H), 2.14 (m, 1H), 1.96 (m, 1H), 1.64 (m, 2H), 1.23 (m, 1H), 1.14 (m, 1H), 0.95 (m, 1H), 0.84 (m, 1H).

Step 4) (6aS,8R,9aR)-5H-5'-methoxyhexahydro-2'H-spiro[cyclopropane-1,1'-pentalen]-2'-one oxime A solution of (3a'R,5'R,6a'R)-5'-methoxyhexahydro-2'H-spiro[cyclopropane-1,1'-pentalen]-2'-one 11d (3.80 g, 21.1 mmol) and hydroxylamine hydrochloride (4.10 g, 59.0 mmol) in pyridine (70 mL) was stirred at 80° C. overnight and concentrated in vacuo. The residue was dissolved in dichloromethane (150 mL). The solution was washed with saturated aqueous sodium chloride (100 mL), dried over anhydrous sodium sulfate and concentrated in vacuo. The residue was purified by silica gel column chromatography (petroleum ether:ethyl acetate (V/V)=10:1) to give the title compound 11e as yellow oil (2.10 g, 51.0%). The compound was characterized by the following spectroscopic data:

MS m/z (ESI): 196.3 (M+1); and
$^1$H NMR (400 MHz, CDCl$_3$) δ: 3.79 (m, 1H), 3.26 (s, 3H), 2.87 (m, 1H), 2.67 (m, 1H), 2.55 (m, 1H), 2.23 (m, 1H), 2.17 (m, 1H), 2.02 (m, 1H), 1.50 (m, 2H), 1.05 (m, 1H), 0.96 (m, 1H), 0.87 (m, 1H), 0.75 (m, 1H).

Step 5) (3a'S,5'R,6a'R)-5'-methoxyhexahydro-2'H-spiro[cyclopropane-1,1'-pentalen]-2'-amine To a solution of (6aS,8R,9aR)-5H-5'-methoxyhexahydro-2'H-spiro[cyclopropane-1,1'-pentalen]-2'-one oxime 11e (2.10 g, 10.7 mmol) in ethanol (200 mL) were added molybdenum trioxide (1.90 g, 13.2 mmol) and sodium borohydride (1.90 g, 50 mmol) in 3 equal additions every 1 hour. The mixture was stirred at 35° C. for 1 hour, and potassium hydroxide (5.6 g, 10 mmol) was added. The reaction mixture was stirred at rt for 2 hours and concentrated in vacuo. The residue was dissolved in saturated aqueous ammonium chloride (150 mL). The solution was washed with petroleum ether (100 mL×3). The aqueous phase was adjusted with sodium carbonate till pH=8-9 and extracted with dichloromethane (100 mL×5). The combined organic layers were dried over anhydrous sodium sulfate and concentrated in vacuo to give the tile compound 11f as colorless oil (1.30 g, 66.8%). The compound was characterized by the following spectroscopic data:

MS m/z (ESI): 196.3 (M+1); and
$^1$H NMR (400 MHz, CDCl$_3$) δ: 3.73 (m, 1H), 3.30 (s, 3H), 3.05 (m, 1H), 2.47 (m, 1H), 2.24 (m, 3H), 1.90 (m, 1H), 1.50 (m, 2H), 1.40 (m, 1H), 0.61 (m, 1H), 0.44 (m, 3H).

Step 6) (2S,4S)-4-fluoro-1-(2-(((3a'S,5'R,6a'R)-5'-methoxyhexahydro-2'H-spiro[cyclopropane-1,1'-pentalen]-2'-yl)amino)acetyl)pyrrolidine-2-carbonitrile A mixture of (2S,4S)-1-(2-chloroacetyl)-4-fluoropyrrolidine-2-carbonitrile 11g (1.36 g, 7.17 mmol), (3a'S,5'R,6a'R)-5'-methoxyhexahydro-2'H-spiro[cyclopropane-1,1'-pentalen]-2'-amine 11f (1.3 g, 7.17 mmol), potassium carbonate (1.3 g, 9.31 mmol), potassium iodide (0.12 g, 0.717 mmol) and tetrahydrofuran (40 mL) was stirred at rt overnight and filtered. The filter cake was washed with tetrahydrofuran (50 mL). The combined filtrates were concentrated in vacuo. The residue was purified by silica gel column chromatography (dichloromethane:methanol (V/V)=50:1) to give the title compound 11 as yellow thick oil (0.85 g, 35.4%). The compound was characterized by the following spectroscopic data:

MS m/z (ESI): 336.3 (M+1); and
$^1$H NMR (400 MHz, CDCl$_3$) δ: 5.53-5.31 (m, 1H), 4.94 (m, 1H), 3.88 (m, 1H), 3.70 (m, 1H), 3.57 (m, 2H), 3.17 (d, 3H), 2.60 (m, 1H), 2.42 (m, 2H), 2.36 (m, 1H), 2.09 (m, 1H), 2.01-1.85 (m, 4H), 1.60-1.40 (m, 4H), 0.70 (m, 1H), 0.48-0.30 (m, 3H).

Example 12

(1S,3S,5S)-2-(2-(((2r,3aR,5S,6aS)-5-Hydroxy-2-methyloctahydropentalen-2-yl)amino) acetyl)-2-azabicyclo[3.1.0]hexane-3-carbonitrile

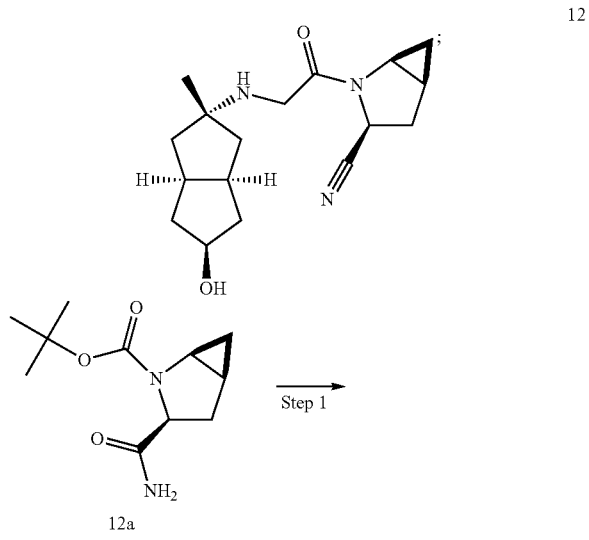

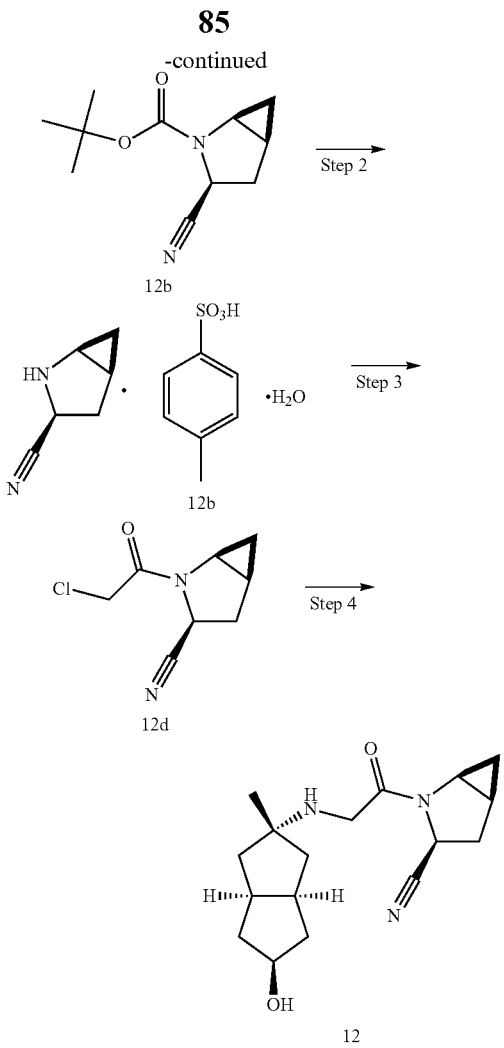

Step 1) (1S,3S,5S)-tert-butyl-3-cyano-2-azabicyclo[3.1.0]hexane-2-carboxylate To a solution of (1S,3S,5S)-tert-butyl-3-carbamoyl-2-azabicyclo[3.1.0]hexane-2-carboxylate 12a (45.2 g, 0.20 mol) in pyridine (400 mL) was added trifluoroacetic anhydride (70 mL, 0.5 mol, Aladdin) dropwise at −20° C. over a period of 2 hours. The mixture was allowed to warm to rt and stirred at rt for 2 hours. The reaction mixture was diluted with water (2 L). The resulting mixture was extracted with ethyl acetate (500 mL×2). The combined organic layers were washed with water (200 mL), adjusted with hydrochloric acid (1 M) till pH=4-5, washed with saturated aqueous sodium bicarbonate (200 mL), dried over anhydrous sodium sulfate and concentrated in vacuo to give the title compound 12b (39.0 g, 93.6%) as yellow oil. The compound was characterized by the following spectroscopic data:

MS m/z (ESI): 231.1 (M+23); and $^1$H NMR (400 MHz, CDCl$_3$) δ: 4.71 (m, 1H), 3.57 (d, 1H), 2.56 (m, 1H), 2.35 (m, 1H), 1.66 (m, 1H), 1.51 (s, 9H), 1.01 (m, 1H), 0.87 (m, 1H).

Step 2) (1S,3S,5S)-2-azabicyclo[3.1.0]hexane-3-carbonitrile 4-methylbenzenesulfonate To a solution of (1S,3S,5S)-tert-butyl-3-cyano-2-azabicyclo[3.1.0]hexane-2-carboxylate 12b (38.3 g, 0.184 mol) in acetonitrile (40 mL) was added p-toluenesulfonic acid monohydrate (52.5 g, 0.276 mol, Guangzhou huada chemical reagent Co., Ltd). The mixture was stirred at rt for 48 hours and concentrated in vacuo. To the residue was added cold ethyl acetate (40 mL). The resulting mixture was stirred at −20° C. for 1 hour and filtered. The filter cake was washed with ethyl acetate (20 mL) to obtain the title compound 12c (46.4 g, 90.0%) as a white solid without further purification. The compound was characterized by the following spectroscopic data:

MS m/z (ESI): 109.2 (M+1); and $^1$H NMR (400 MHz, CDCl$_3$) δ: 10.31 (brs, 1H), 7.53 (d, 2H), 7.14 (d, 2H) 5.06 (m, 1H), 3.46 (m, 1H), 2.54 (m, 1H), 2.31 (m, 3H), 2.27 (m, 1H), 1.89 (m, 1H), 0.97 (m, 2H).

Step 3) (1S,3S,5S)-2-(2-chloroacetyl)-2-azabicyclo[3.1.0]hexane-3-carbonitrile To a mixture of (1S,3S,5S)-2-azabicyclo[3.1.0]hexane-3-carbonitrile 4-methylbenzenesulfonate 12c (45.8 g, 0.163 mol) and triethylamine (114 mL, 0.817 mol) was added chloroacetyl chloride (26 mL, 0.327 mol, Shanghai hanhong chemical Co., Ltd) dropwise at 5° C. over a period of 2 hours. The mixture was stirred at 0-5° C. for 2 hours and washed with water (400 mL×2). The organic phase was dried over anhydrous sodium sulfate and concentrated in vacuo. To the residue was added methyl tertiary butyl ether (100 mL). The mixture was stirred at 0° C. for 2 hours and filtered. The filter cake was dried under vacuum to obtain the title compound 12d (21.1 g, 70.1%). The compound was characterized by the following spectroscopic data:

MS m/z (ESI): 185 (M+1); and $^1$H NMR (400 MHz, CDCl$_3$) δ: 4.93 (m, 1H), 4.18 (m, 2H), 3.57 (m, 1H), 2.59 (m, 1H), 2.39 (m, 1H), 1.89 (m, 1H), 1.06 (m, 2H).

Step 4) (1S,3S,5S)-2-(2-(((2r,3aR,5S,6aS)-5-hydroxy-2-methyloctahydropentalen-2-yl)amino)acetyl)-2-azabicyclo[3.1.0]hexane-3-carbonitrile A mixture of (2r,3aR,5r,6aS)-5-amino-5-methyloctahydropentalen-2-ol (0.90 g, 5.8 mmol, prepared in step 4 of example 3), potassium iodide (1.50 g, 9.0 mmol), potassium carbonate (10.0 g, 72.2 mmol) and (1S,3S,5S)-2-(2-chloroacetyl)-2-azabicyclo[3.1.0]hexane-3-carbonitrile 12d (3.33 g, 18.0 mmol) in N,N-dimethylformamide (30 mL) was stirred at rt overnight. Most of the solvent was removed in vacuo at 70° C. The residue was diluted with water (30 mL). The resulting mixture was extracted with dichloromethane/methanol (200 mL, V/V=10:1). The organic layer was washed with water (30 mL) and concentrated in vacuo. The residue was purified by silica gel column chromatography (dichloromethane:methanol (V/V)=30:1) to give the title compound 12 as a yellow solid (0.70 g, 40%). The compound was characterized by the following spectroscopic data:

MS m/z (ESI): 304.2 (M+1); and $^1$H NMR (400 MHz, CDCl$_3$) δ: 4.94 (d, 1H), 4.31 (t, 1H), 3.48 (m, 2H), 3.45 (m, 1H), 2.64 (m, 2H), 2.55 (m, 1H), 2.38 (m, 1H), 2.04 (m, 2H), 1.97 (m, 2H), 1.84 (m, 1H), 1.73 (s, 2H), 1.40 (m, 3H), 1.20 (s, 3H), 1.10 (m, 1H), 1.00 (m, 1H).

Example 13

(2S,4S)-1-(2-(((2r,3aR,5S,6aS)-5-Cyclopropoxy-2-methyloctahydropentalen-2-yl)amino)acetyl)-4-fluoropyrrolidine-2-carbonitrile

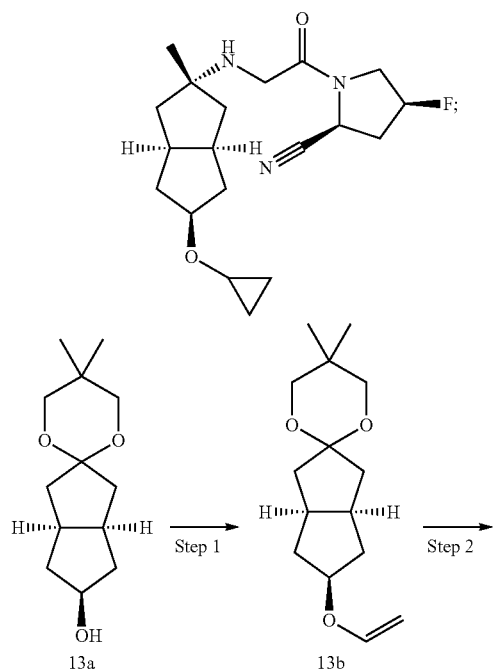

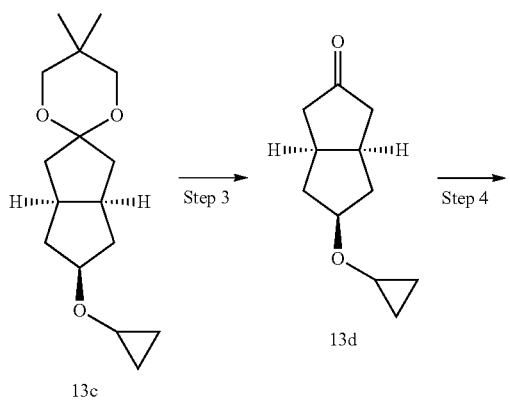

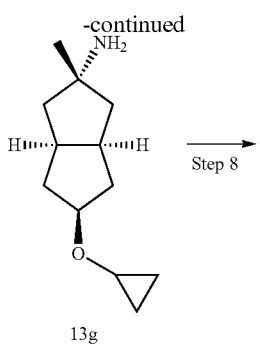

Step 1) (3a'R,5's,6a'S)-5,5-dimethyl-5'-(vinyloxy) hexahydro-1'H-spiro[[1,3]dioxane-2,2'-pentalene]

To a solution of o-phenanthroline (80 mg, 0.442 mmol) in ethyl vinyl ether (25 mL) was added palladium diacetate (295 mg, 0.442 mmol). The mixture was stirred at rt for 20 min, and a solution of (3a'R,5's,6a'S)-5,5-dimethylhexahydro-1'H-spiro[[1,3]dioxane-2,2'-pentalen]-5'-ol 13a (5.00 g, 22.1 mmol, prepared in step 2 of example 1) in ethyl vinyl ether (25 mL) was added. The reaction mixture was stirred at 45° C. for 20 hours, cooled to rt and filtered. The filtrate was concentrated in vacuo. The residue was purified by silica gel column chromatography (petroleum ether:ethyl acetate (V/V)=20:1) to give the title compound 13b as yellow oil (4.01 g, 71.9%). The compound was characterized by the following spectroscopic data:

MS m/z (ESI): 275.3 (M+23); and $^1$H NMR (400 MHz, CDCl$_3$) δ: 6.27 (dd, 1H), 4.32 (m, 1H), 4.19 (dd, 1H), 3.97 (dd, 1H), 3.47 (s, 2H), 3.45 (s, 2H), 2.49 (m, 2H), 2.27 (m, 2H), 1.99 (m, 2H), 1.76 (m, 4H), 0.95 (s, 6H).

Step 2) (3a'R,5's,6a'S)-5'-cyclopropoxy-5,5-dimethylhexahydro-1'H-spiro[[1,3]dioxane-2,2'-pentalene]

To a solution of (3a'R,5's,6a'S)-5,5-dimethyl-5'-(vinyloxy) hexahydro-1'H-spiro[[1,3]dioxane-2,2'-pentalene] 13b (21.38 g, 84.8 mmol) and diiodomethane (56.81 g, 212 mmol) in anhydrous dichloromethane (200 mL) was added diethylzinc (187 mL, 187 mmol, 1M in hexane) at 0° C. over a period of 30 min. The mixture was stirred at 0° C. for 30 min and 5° C. for 4 hours. Saturated aqueous sodium bicarbonate (100 mL) was added to the reaction mixture. The resulting mixture was extracted with dichloromethane (200 mL×3). The combined organic layers were washed with saturated aqueous sodium chloride (100 mL), dried over anhydrous sodium sulfate and concentrated in vacuo. The residue was purified by silica gel column chromatography (petroleum ether:ethyl acetate (V/V)=20:1) to give the title compound 13c as yellow oil (13.43 g, 59.5%). The compound was characterized by the following spectroscopic data:

MS m/z (ESI): 267.3 (M+1); and $^1$H NMR (400 MHz, CDCl$_3$) δ: 3.90 (m, 1H), 3.47 (s, 2H), 3.46 (s, 2H), 3.22 (m, 1H), 2.41 (m, 2H), 2.22 (m, 2H), 2.08 (m, 2H), 1.70 (m, 2H), 1.48 (m, 2H), 0.95 (s, 6H), 0.52 (m, 2H), 0.42 (m, 2H).

Step 3) (3aR,5s,6aS)-5-cyclopropoxyhexahydropentalen-2(1H)-one

To a mixture of (3a'R,5's,6a'S)-5'-cyclopropoxy-5,5-dimethylhexahydro-1'H-spiro[[1,3]dioxane-2,2'-pentalene] 13c (0.59 g, 2.22 mmol) in acetone (40 mL) were added water (2 mL) and p-toluenesulfonic acid (30 mg, 0.155 mmol). The mixture was stirred at rt for 3 hours and saturated aqueous sodium bicarbonate (5 mL) was added. The organic layer was dried over anhydrous sodium sulfate and concentrated in vacuo. The residue was purified by silica gel column chromatography (petroleum ether:ethyl acetate (V/V)=10:1) to give the title compound 13d as yellow oil (0.36 g, 90.0%%). The compound was characterized by the following spectroscopic data:

$^1$H NMR (400 MHz, CDCl$_3$) δ: 4.06 (m, 1H), 3.20 (m, 1H), 2.72 (m, 2H), 2.45 (m, 2H), 2.16 (m, 4H), 1.60 (m, 2H), 0.52 (m, 2H), 0.42 (m, 2H).

Step 4) (2r,3aR,5s,6aS)-5-cyclopropoxy-2-methyloctahydropentalen-2-ol

To a solution of methylmagnesium bromide (33.3 mL, 100 mol, 3 M in ether) in tetrahydrofuran (100 mL) was added a solution of (3aR,5s,6aS)-5-cyclopropoxyhexahydropentalen-2(1H)-one 13d (9.00 g, 50.0 mmol) in tetrahydrofuran (50 mL) at 0° C. over a period of 15 min. The mixture was refluxed overnight. The reaction mixture was quenched with saturated aqueous ammonium chloride (10 mL), and extracted with dichloromethane (100 mL×3). The combined organic layers were washed with saturated aqueous sodium chloride (100 mL), dried over anhydrous sodium sulfate and concentrated in vacuo to give the title compound 13e as yellow oil (9.20 g, 93.8%). The compound was characterized by the following spectroscopic data:

GC-MS m/z (EI): 196.3 (M).

Step 5) (2r,3aR,5r,6aS)-2-azido-5-cyclopropoxy-2-methyloctahydropentalene

To a sulfuric acid solution (38 mL, 9.27 M in water) was added sodium azide (6.10 g, 93.9 mmol, Tianjin tian da chemical reagent Co., Ltd) at 0° C. with stirring. The mixture was stirred at rt for 30 min and a solution of (2r,3aR,5s,6aS)-5-cyclopropoxy-2-methyloctahydropentalen-2-ol 13e (9.20 g, 46.9 mmol) in trichloromethane (100 mL) was added. The resulting mixture was stirred at 40° C. for 8 hours and extracted with dichloromethane (100 mL×3). The combined organic layers were washed with saturated aqueous sodium chloride (100 mL), dried over anhydrous sodium sulfate and concentrated in vacuo to give the title compound 13f as yellow oil (9.36 g, 90.2%) without further purification. The compound was characterized by the following spectroscopic data:

GC-MS m/z (EI): 221.3 (M).

Step 6) (2r,3aR,5r,6aS)-5-cyclopropoxy-2-methyloctahydropentalen-2-amine

To a solution of (2r,3aR,5r,6aS)-2-azido-5-cyclopropoxy-2-methyloctahydropentalene 13f (9.36 g, 42.3 mmol) in methanol (200 mL) was added Pd/C (1.00 g, 10%, ~W/W=55%, Shaanxi kai da chemical reagent Co., Ltd). The mixture was stirred under H$_2$ for 14 hours. The reaction mixture was filtered. The filtrate was concentrated in vacuo. The residue was purified by silica gel column chromatography (dichloromethane:methanol (V/V)=20:1) to give the title compound 13g as yellow oil (3.85 g, 46.6%). The compound was characterized by the following spectroscopic data:

MS m/z (ESI): 196.3 (M+1); and $^1$H NMR (400 MHz, CDCl$_3$) δ: 4.03 (m, 1H), 3.19 (m, 1H), 2.89 (m, 2H), 2.25 (m, 2H), 1.94 (m, 2H), 1.55 (m, 4H), 1.53 (s, 3H), 0.50 (m, 2H), 0.43 (m, 2H).

Step 7) (2S,4S)-1-(2-(((2r,3aR,5S,6aS)-5-cyclopropoxy-2-methyloctahydropentalen-2-yl)amino)acetyl)-4-fluoropyrrolidine-2-carbonitrile To a solution of (2r,3aR,5r,6aS)-5-cyclopropoxy-2-methyloctahydropentalen-2-amine 13g (1.24 g, 6.36 mmol) in tetrahydrofuran/N,N-dimethylformamide (60 mL, V/V=2:1) were added potassium iodide (106 mg, 0.636 mmol), potassium carbonate (4.39 g, 31.8 mmol) and (2S,4S)-1-(2-chloroacetyl)-4-fluoropyrrolidine-2-carbonitrile (1.21 g, 6.36 mmol). The mixture was stirred at rt for 1 day and diluted with dichloromethane (100 mL). The resulting mixture was washed with saturated aqueous sodium chloride (200 mL), dried over anhydrous sodium sulfate and concentrated in vacuo. The residue was purified by silica gel column chromatography (dichloromethane:methanol (V/V)=40:1) to give the title compound 13 as a yellow semisolid (920 mg, 41.4%, HPLC: 94.0%). The compound was characterized by the following spectroscopic data:

MS m/z (ESI): 350.3 (M+1); and $^1$H NMR (400 MHz, CDCl$_3$) δ: 5.37 (m, 1H), 4.98 (d, J=9.2 Hz, 1H), 4.00 (m, 1H), 3.79 (m, 2H), 3.39 (m, 2H), 3.32 (s, 2H), 3.22 (m, 1H), 2.63 (m, 2H), 2.02 (m, 4H), 1.47 (m, 4H), 1.25 (s, 3H), 0.50 (m, 2H), 0.42 (m, 2H).

Example 14

(S)-1-(2-(((2r,3aR,5S,6aS)-5-Cyclopropoxy-2-methyloctahydropentalen-2-yl)amino)acetyl)pyrrolidine-2-carbonitrile

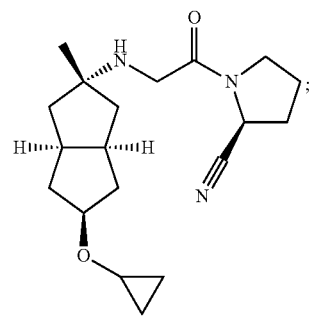

14

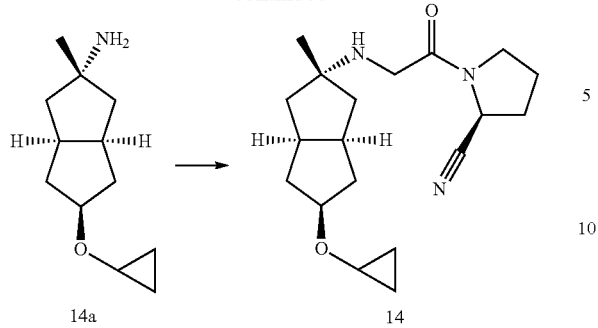

To a solution of (2r,3aR,5r,6aS)-5-cyclopropoxy-2-methyloctahydropentalen-2-amine 14a (0.66 g, 3.38 mmol, prepared in step 6 of example 13) in N,N-dimethylformamide (50 mL) were added (S)-1-(2-chloroacetyl) pyrrolidine-2-carbonitrile (0.58 g, 3.38 mmol), potassium iodide (56 mg, 0.338 mmol) and potassium carbonate (0.51 g, 3.72 mmol). The mixture was stirred at rt for 1 day and concentrated in vacuo. The residue was dissolved in dichloromethane (80 mL). The solution was washed with saturated aqueous sodium chloride (80 mL), dried over anhydrous sodium sulfate and concentrated in vacuo. The residue was purified by silica gel column chromatography (dichloromethane:methanol (V/V)=40:1) to give the title compound 14 as yellow oil (350 mg, 31.3%, HPLC: 96.2%). The compound was characterized by the following spectroscopic data:

MS m/z (ESI): 332.2 (M+1); and $^1$H NMR (400 MHz, CDCl$_3$) δ: 4.77-4.74 (m, 1H), 3.94 (m, 1H), 3.58 (m, 1H), 3.38 (m, 1H), 3.34 (m, 2H), 3.20 (m, 1H), 2.60 (m, 2H), 2.16 (m, 4H), 1.94 (m, 4H), 1.40 (m, 4H), 1.19 (s, 3H), 0.51 (m, 2H), 0.41 (m, 2H).

Example 15

(2S,4S)-1-(2-(((2s,3aR,6aS)-5-Cyano-2-methyloctahydropentalen-2-yl)amino)acetyl)-4-fluoropyrrolidine-2-carbonitrile

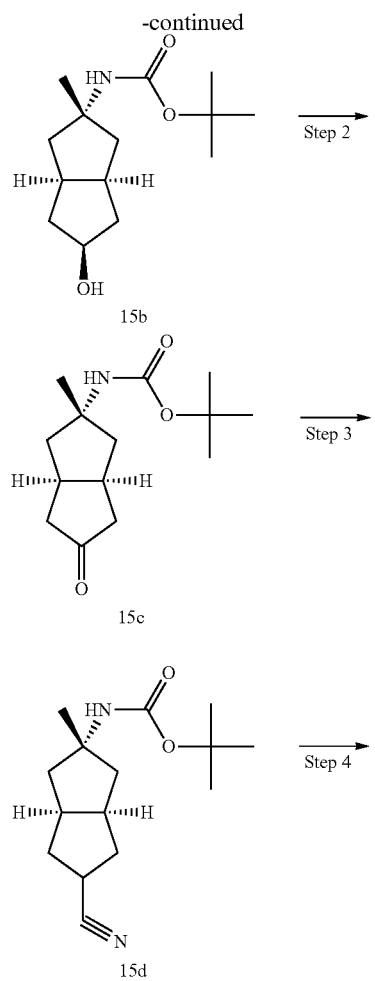

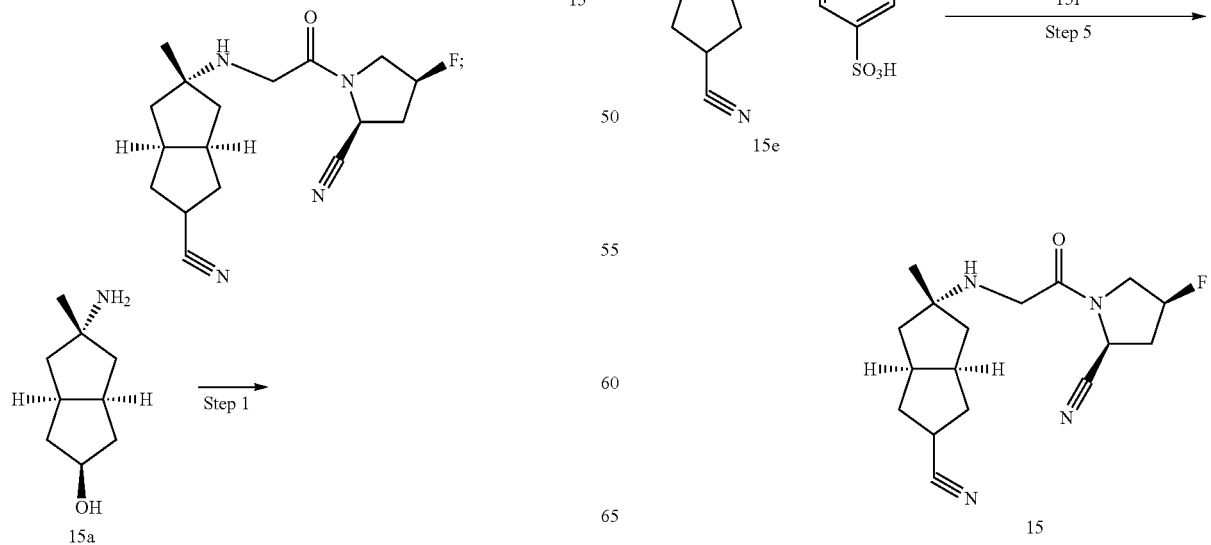

Step 1) tert-butyl ((2r,3aR,5r,6aS)-5-hydroxy-2-methyloctahydropentalen-2-yl)carbamate To a solution of (2r,3aR,5r,6aS)-5-amino-5-methyloctahydropentalen-2-ol 15a (4.32 g, 28.3 mmol, prepared in step 4 of example 3) in methanol (50 mL) were added di-tert-butyl dicarbonate (9.26 g, 42.5 mmol), triethylamine (4.29 g, 42.5 mmol) and 4-dimethylaminopyridine (345 mg, 2.83 mmol). The mixture was refluxed for 8 hours and concentrated in vacuo. The residue was was purified by silica gel column chromatography (petroleum ether:ethyl acetate (V/V)=6:1) to give the title compound 15b as a white solid (5.12 g, 70.8%). The compound was characterized by the following spectroscopic data:

MS m/z (ESI): 278.2 (M+23); and $^1$H NMR (400 MHz, DMSO-d$_6$) δ: 6.33 (s, 1H), 4.43 (d, 1H), 4.06 (m, 1H), 2.32-2.40 (m, 4H), 1.81 (m, 2H), 1.36 (s, 9H), 1.31 (m, 2H), 1.26 (s, 3H), 1.24 (m, 2H).

Step 2) tert-butyl ((2r,3aR,6aS)-2-methyl-5-oxooctahydropentalen-2-yl)carbamate To a solution of tert-butyl ((2r,3aR,5r,6aS)-5-hydroxy-2-methyloctahydropentalen-2-yl) carbamate 15b (11.3 g, 44.3 mmol) in dichloromethane (20 mL) was added Dess-Martin periodinane (37.5 g, 88.6 mmol). The mixture was stirred at rt for 3 hours and concentrated in vacuo. The residue was dissolved in ethyl acetate (80 mL). The solution was washed with saturated aqueous sodium bicarbonate (80 mL). The organic layer was dried over anhydrous sodium sulfate and concentrated in vacuo to give the title compound 15c as oil (8.05 g, 71.7%). The compound was characterized by the following spectroscopic data:

MS m/z (ESI): 276.2 (M+23); and $^1$H NMR (400 MHz, DMSO-d$_6$) δ: 6.54 (s, 1H), 2.72 (m, 2H), 2.41 (m, 4H), 1.97 (d, 2H), 1.37 (s, 9H), 1.30 (s, 3H), 1.17 (m, 2H).

Step 3) tert-butyl ((2s,3aR,6aS)-5-cyano-2-methyloctahydropentalen-2-yl)carbamate To a solution of tert-butyl ((2r,3aR,6aS)-2-methyl-5-oxooctahydropentalen-2-yl) carbamate 15c (6.04 g, 23.7 mmol) in 1,2-dimethoxyethane (240 mL) was added a solution of p-tosylmethyl isocyanide (13.86 g, 71.1 mmol) and potassium tert-butoxide (10.62 g, 94.8 mmol) in ethanol (60 mL). The mixture was stirred at rt for 5 hours, quenched with water (50 mL), and concentrated in vacuo. The residue was extracted with ethyl acetate (500 mL). The organic layer was washed with saturated aqueous sodium chloride (200 mL x 3), dried over anhydrous sodium sulfate and concentrated in vacuo. The residue was purified by silica gel column chromatography (petroleum ether:ethyl acetate (V/V)=100:1 to give the title compound 15d as pale yellow oil (3.01 g, 47.9%). The compound was characterized by the following spectroscopic data:

MS m/z (ESI): 287.2 (M+23); and $^1$H NMR (400 MHz, CDCl$_3$) δ: 4.37 (d, 1H), 2.76 (m, 2H), 2.34 (brs, 1H), 2.19 (m, 2H), 1.91 (m, 2H), 1.70 (m, 2H), 1.43 (s, 9H), 1.38 (s, 3H), 1.27 (m, 2H).

Step 4) (3aR,5s,6aS)-5-amino-5-methyloctahydropentalene-2-carbonitrile-4-methylbenzenesulfonate To a solution of tert-butyl ((2s,3aR,6aS)-5-cyano-2-methyloctahydropentalen-2-yl) carbamate 15d (2.51 g, 9.47 mmol) in acetonitrile (10 mL) was added p-toluenesulfonic acid monohydrate (2.69 g, 14.2 mmol). The mixture was stirred at rt overnight and concentrated in vacuo. To the residue was added cold ethyl acetate (50 mL) at 0° C. and solid precipitated out. The mixture was filtered to give the title compound 15e as a yellow solid (2.92 g, 91.5%). The compound was characterized by the following spectroscopic data:

MS m/z (ESI): 165.3 (M+1); and $^1$H NMR (400 MHz, CD$_3$OD-d$_4$) δ: 7.70 (d, 2H), 7.24 (d, 2H), 2.93 (m, 1H), 2.83 (m, 2H), 2.36 (s, 3H), 2.22 (m, 2H), 2.12 (m, 2H), 1.88 (m, 2H), 1.69 (m, 2H), 1.43 (s, 3H).

Step 5) (2S,4S)-1-(2-(((2s,3aR,6aS)-5-cyano-2-methyloctahydropentalen-2-yl)amino)acetyl)-4-fluoropyrrolidine-2-carbonitrile To a solution of (3 aR,5s,6 aS)-5-amino-5-methyloctahydropentalene-2-carbonitrile 4-methylbenzenesulfonate 15e (1.5 g, 4.46 mmol) in N,N-dimethylformamide (10 mL) were added potassium iodide (0.740 g, 4.46 mmol), potassium carbonate (1.85 g, 13.4 mmol) and (2S,4S)-1-(2-chloroacetyl)-4-fluoropyrrolidine-2-carbonitrile (0.849 g, 4.46 mmol). The mixture was stirred at rt overnight. To the mixture was added water (100 mL). The resulting mixture was extracted with dichloromethane (100 mL×3). The combined organic layers were washed with saturated aqueous sodium chloride (100 mL), dried over anhydrous sodium sulfate and concentrated in vacuo. The residue was purified by silica gel column chromatography (ethyl acetate:methanol (V/V)=10:1) to give the title compound 15 as a white solid (0.98 g, 69.0%). The compound was characterized by the following spectroscopic data:

MS m/z (ESI): 319.2 (M+1); and $^1$H NMR (400 MHz, CD$_3$OD-d$_4$) δ: 5.50 (m, 1H), 4.97 (m, 1H), 3.96 (m, 1H), 3.73 (m, 2H), 2.83 (m, 2H), 2.56 (m, 2H), 2.22 (m, 2H), 2.01 (m, 2H), 1.86 (d, 2H), 1.68 (t, 2H), 1.43 (m, 2H), 1.22 (m, 3H).

Example 16

(2S)-1-(2-(((2s,3aR,6aS)-5-Cyano-2-methyloctahydropentalen-2-yl)amino)acetyl)pyrrolidine-2-carbonitrile

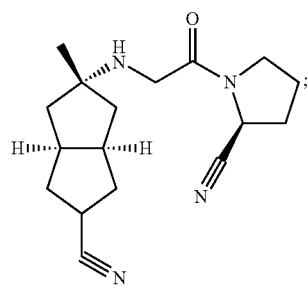

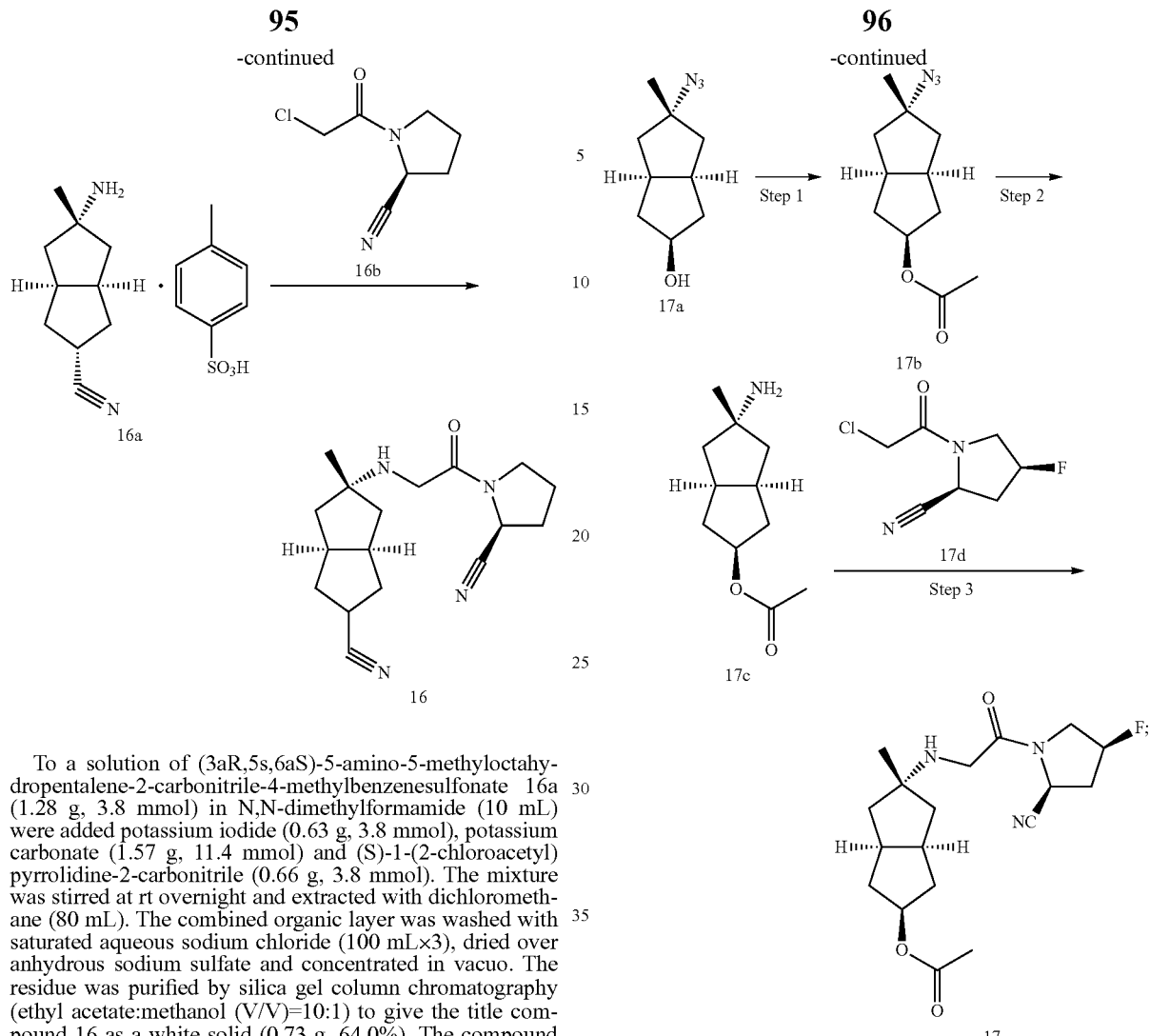

To a solution of (3aR,5s,6aS)-5-amino-5-methyloctahydropentalene-2-carbonitrile-4-methylbenzenesulfonate 16a (1.28 g, 3.8 mmol) in N,N-dimethylformamide (10 mL) were added potassium iodide (0.63 g, 3.8 mmol), potassium carbonate (1.57 g, 11.4 mmol) and (S)-1-(2-chloroacetyl)pyrrolidine-2-carbonitrile (0.66 g, 3.8 mmol). The mixture was stirred at rt overnight and extracted with dichloromethane (80 mL). The combined organic layer was washed with saturated aqueous sodium chloride (100 mL×3), dried over anhydrous sodium sulfate and concentrated in vacuo. The residue was purified by silica gel column chromatography (ethyl acetate:methanol (V/V)=10:1) to give the title compound 16 as a white solid (0.73 g, 64.0%). The compound was characterized by the following spectroscopic data:

MS m/z (ESI): 301.3 (M+1); and $^1$H NMR (400 MHz, CD$_3$OD-d$_4$) δ: 4.76 (t, 1H), 3.65 (m, 1H), 3.48 (m, 1H), 3.35 (m, 2H), 2.93 (m, 1H), 2.83 (m, 2H), 2.23 (m, 2H), 2.15 (m, 2H), 2.03 (m, 2H), 1.86 (d, 2H), 1.66 (m, 1H), 1.44 (m, 1H), 1.22 (m, 3H), 1.10 (m, 1H).

Example 17

(2S,3aR,5r,6aS)-5-((2-((2S,4S)-2-Cyano-4-fluoropyrrolidin-1-yl)-2-oxoethyl)amino)-5-methyloctahydropentalen-2-yl acetate

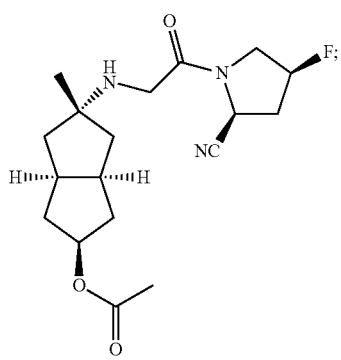

Step 1) (2r,3aR,5r,6aS)-5-azido-5-methyloctahydropentalen-2-yl acetate

To a solution of (2r,3aR,5r,6aS)-5-azido-5-methyloctahydropentalen-2-ol 17a (1.23 g, 6.79 mmol, prepared in step 4 of example 3) in dichloromethane (20 mL) were added acetic anhydride (7.38 mL, 82.8 mmol), triethylamine (23.09 mL, 165.7 mmol) and 4-dimethylaminopyridine (0.168 g, 1.38 mmol). The mixture was stirred at rt for 8 hours and 100 mL of water was added. The organic layer was washed with saturated aqueous sodium chloride (100 mL×3), dried over anhydrous sodium sulfate and concentrated in vacuo. The residue was purified by silica gel column chromatography (petroleum ether:ethyl acetate (V/V)=50:1) to give the title compound 17b as yellow oil (0.99 g, 65.2%). The compound was characterized by the following spectroscopic data:

MS m/z (ESI): 181.1 (M-42); and $^1$H NMR (400 MHz, CDCl$_3$) δ: 5.18 (m, 1H), 2.71 (m, 2H), 2.02 (m, 4H), 1.98 (s, 3H), 1.62 (d, 2H), 1.49 (m, 2H), 1.39 (s, 3H).

Step 2) (2r,3aR,5r,6aS)-5-amino-5-methyloctahydropentalen-2-yl acetate

To a solution of (2r,3aR,5r,6aS)-5-azido-5-methyloctahydropentalen-2-yl acetate 17b (4.02 g, 17.9 mmol) in methanol (50 mL) was added Pd/C (0.5 g, 10%, ~W/W=55%, Shaanxi kai da chemical reagent Co., Ltd). The mixture was stirred under H₂ for 14 hours. The reaction mixture was filtered. The filtrate was concentrated in vacuo. The residue was purified by silica gel column chromatography (ethyl acetate:methanol (V/V)=6:1) to give the title compound 17c as pale yellow oil (2.79 g, 79.0%). The compound was characterized by the following spectroscopic data:

MS m/z (ESI): 198.2 (M+1); and $^1$H NMR (400 MHz, CDCl₃) δ: 5.11 (m, 1H), 2.71 (t, 2H), 2.01 (m, 2H), 1.95 (s, 3H), 1.75 (m, 2H), 1.69 (s, 2H), 1.54 (m, 2H), 1.45 (m, 2H), 1.21 (s, 3H).

Step 3) (2S,3aR,5r,6aS)-5-((2-((2S,4S)-2-cyano-4-fluoropyrrolidin-1-yl)-2-oxoethyl)amino)-5-methyl-octahydropentalen-2-yl acetate To a solution of (2r,3aR,5r,6aS)-5-amino-5-methyloctahydropentalen-2-yl acetate 17c (0.964 g, 5.076 mmol) in N,N-dimethylformamide (20 mL) were added (2S,4S)-1-(2-chloroacetyl)-4-fluoropyrrolidine-2-carbonitrile 17d (0.964 g, 5.076 mmol), potassium iodide (0.837 g, 5.076 mmol) and triethylamine (0.7 mL, 5.076 mmol). The mixture was stirred at rt overnight and extracted with dichloromethane (50 mL×3). The combined organic layers were washed with saturated aqueous sodium chloride (100 mL), dried over anhydrous sodium sulfate and concentrated in vacuo. The residue was purified by silica gel column chromatography (ethyl acetate:methanol (V/V)=15:1) to give the title compound 17 as yellow oil (0.92 g, 51.7%, HPLC: 98.71%). The compound was characterized by the following spectroscopic data:

MS m/z (ESI): 352.2 (M+1); and $^1$H NMR (400 MHz, CDCl₃) δ: 5.50 (m, 1H), 5.15 (t, 2H), 4.94 (d, 1H), 3.97-3.67 (m, 2H), 3.48 (t, 1H), 3.34 (m, 2H), 2.70 (m, 4H), 2.40 (m, 1H), 2.00 (s, 3H), 1.86 (s, 2H), 1.60 (t, 2H), 1.41 (t, 2H), 1.18 (s, 3H).

Example 18

(2S,3aR,5r,6aS)-5-((2-((S)-2-Cyanopyrrolidin-1-yl)-2-oxoethyl)amino)-5-methyloctahydropentalen-2-yl acetate

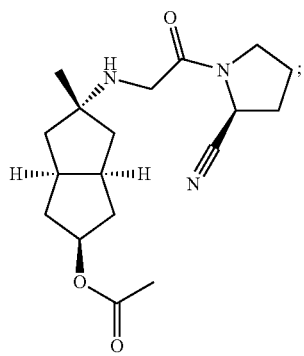

18

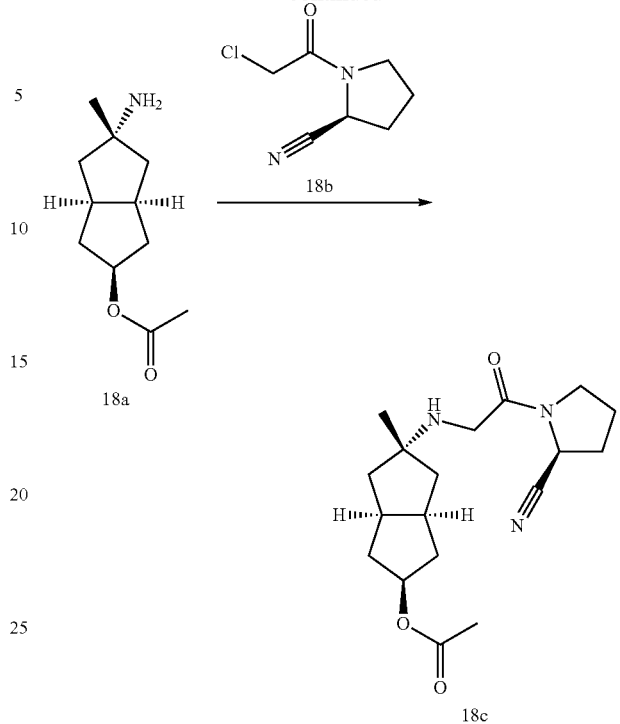

To a solution of (2r,3aR,5r,6aS)-5-amino-5-methyloctahydropentalen-2-yl acetate 18a (1.00 g, 5.076 mmol, prepared in step 2 of example 17) in N,N-dimethylformamide (10 mL) were added (S)-1-(2-chloroacetyl) pyrrolidine-2-carbonitrile 18b (0.873 g, 5.076 mmol), potassium iodide (0.837 g, 5.076 mmol) and triethylamine (0.7 mL, 5.076 mmol). The mixture was stirred at rt overnight and extracted with dichloromethane (20 mL×3). The combined organic layers were washed with saturated aqueous sodium chloride (50 mL), dried over anhydrous sodium sulfate and concentrated in vacuo. The residue was purified by silica gel column chromatography (ethyl acetate:methanol (V/V)=15:1) to give the title compound 18 as yellow oil (0.75 g, 44.3%, HPLC: 98.28%). The compound was characterized by the following spectroscopic data:

MS m/z (ESI): 334.2 (M+1); and $^1$H NMR (400 MHz, CDCl₃) δ: 5.16 (m, 1H), 4.75 (m, 1H), 3.60 (m, 1H), 3.46 (m, 2H), 2.72 (d, 2H), 2.24 (m, 2H), 2.17 (m, 2H), 2.05 (d, 4H), 1.99 (s, 3H), 1.59 (d, 2H), 1.41 (m, 2H), 1.25 (m, 2H), 1.20 (s, 3H).

Example 19

(2S,4S)-4-Fluoro-1-(2-(((3a'R,5'r,6a'S)-5'-methyl-hexahydro-1'H-spiro[oxetane-2,2'-pentalen]-5'-yl)amino)acetyl)pyrrolidine-2-carbonitrile

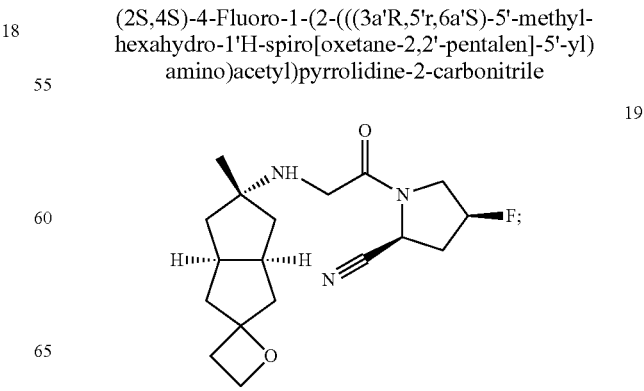

19

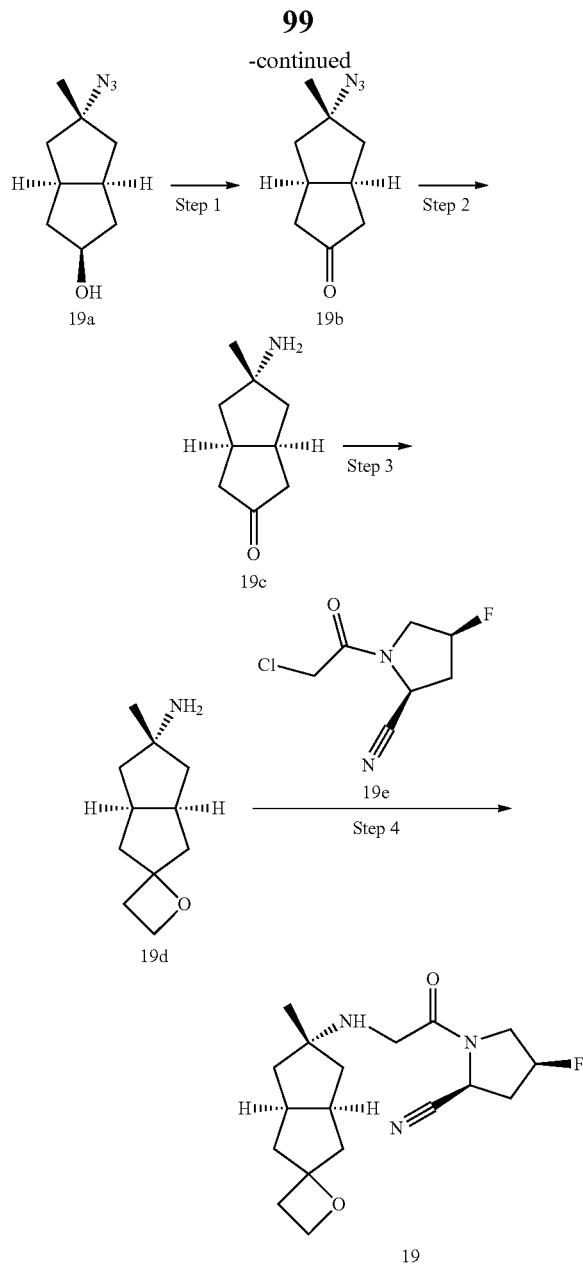

Step 1) (3aR,5r,6aS)-5-azido-5-methylhexahydropentalen-2(1H)-one

To a solution of (2r,3aR,5r,6aS)-5-azido-5-methyloctahydropentalen-2-ol 19a (0.200 g, 1.10 mmol) in dichloromethane (50 mL) was added Dess-Martin periodinane (0.94 g, 2.21 mmol) at 0° C. The mixture was stirred at 0° C. for 0.5 hour and rt for 2 hours. To the mixture was added saturated aqueous sodium bicarbonate (50 mL). The aqueous layer was extracted with ethyl acetate (20 mL×3). The combined organic layers were washed with saturated aqueous sodium chloride (100 mL), dried over anhydrous magnesium sulfate and concentrated in vacuo. The residue was purified by silica gel column chromatography (petroleum ether:ethyl acetate (V/V)=10:1) to give the title compound 19b as yellow oil (90 mg, 45%). The compound was characterized by the following spectroscopic data:

GC-MS m/z (EI): 179.1 (M);
$^1$H NMR (400 MHz, DMSO-$d_6$) δ: 2.78 (m, 2H), 2.42 (m, 2H), 2.00 (m, 4H), 1.47 (m, 2H), 1.41 (s, 3H).

Step 2) (3aR,5r,6aS)-5-amino-5-methylhexahydropentalen-2(1H)-one

To a solution of (3aR,5r,6aS)-5-azido-5-methylhexahydropentalen-2(1H)-one 19b (1.00 g, 5.59 mmol) in methanol (50 mL) was added Pd/C (0.2 g, 10%, ~W/W=55%, Shaanxi kai da chemical reagent Co., Ltd). The mixture was stirred under $H_2$ overnight. The reaction mixture was filtered. The filtrate was concentrated in vacuo to give the title compound 19c as a white solid (0.82 g, 95.3%). The compound was characterized by the following spectroscopic data:

MS m/z (ESI): 154.3 (M+1).

Step 3) (3a'R,5'r,6a'S)-5'-methylhexahydro-1'H-spiro[oxetane-2,2'-pentalen]-5'-amine To a solution of trimethylsulfoxonium iodide (54.8 g, 249 mmol) in tert-butanol (100 mL) was added a solution of potassium tert-butanolate (27.9 g, 249 mmol) in tert-butanol (200 mL) dropwise. The reaction mixture was stirred at 50° C. for 1 hour and a solution of (3 aR,5 r,6 aS)-5-amino-5-methylhexahydropentalen-2(1H)-one 19c (9.53 g, 62.3 mmol) in tert-butanol (60 mL) was added. The resulting mixture was further stirred at 50° C. for 3 days, cooled and filtered. The filter cake was washed with ethyl acetate (50 mL). The combined filtrates were concentrated in vacuo. The residue was purified by silica gel column chromatography (dichloromethane:methanol (V/V)=20:1) to give the title compound 19d as yellow oil (4.35g, 38.5%). The compound was characterized by the following spectroscopic data:

MS m/z (ESI): 182.2 (M+1); and
$^1$H NMR (400 MHz, $CD_3Cl$) δ: 4.44 (m, 2H), 2.70 (m, 2H), 2.52 (m, 2H), 1.91 (m, 2H), 1.74 (m, 6H), 1.49 (m, 2H), 1.25 (s, 3H)

Step 4) (2S,4S)-4-fluoro-1-(2-(((3a'R,5'r,6a'S)-5'-methylhexahydro-1'H-spiro[oxetane-2,2'-pentalen]-5'-yl)amino)acetyl)pyrrolidine-2-carbonitrile To a solution of (3a'R,5'r,6a'S)-5'-methylhexahydro-1'H-spiro[oxetane-2,2'-pentalen]-5'-amine 19d (1.68 g, 9.28 mmol) in tetrahydrofuran (100 mL) were added (2S,4S)-1-(2-chloroacetyl)-4-fluoropyrrolidine-2-carbonitrile 19e (1.77 g, 9.28 mmol), potassium iodide (154 mg, 0.928 mmol) and potassium carbonate (6.40 g, 46.4 mmol). The mixture was stirred at rt for 2 days and concentrated in vacuo. The residue was dissolved in dichloromethane (100 mL). The solution was washed with saturated aqueous sodium chloride (100 mL) and concentrated in vacuo. The residue was purified by silica gel column chromatography (dichloromethane:methanol (V/V)=40:1) to give the title compound 19 as a white solid (0.70 g, 22.5%, HPLC: 97.6%). The compound was characterized by the following spectroscopic data:

MS m/z (ESI): 336.3 (M+1); and
$^1$H NMR (400 MHz, $CDCl_3$) δ: 5.48 (m, 1H), 4.94 (m, 1H), 4.44 (t, 2H), 4.02-3.66 (m, 2H), 3.28 (m, 2H), 2.73 (m, 2H), 2.58 (t, 2H), 2.23 (m, 2H), 1.93 (m, 4H), 1.54 (m, 2H), 1.26 (m, 2H), 1.18 (s, 3H).

Example 20

(2S,4S)-1-(2-(((2s,3aR,6aS)-5-Ethynyl-2-methyloctahydropentalen-2-yl)amino)acetyl)-4-fluoropyrrolidine-2-carbonitrile

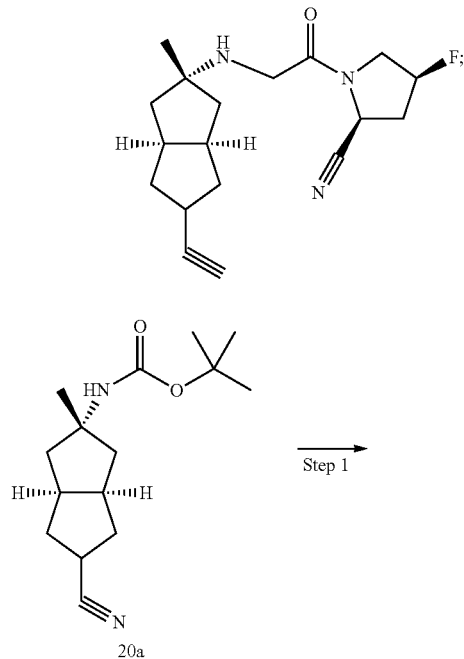

20a

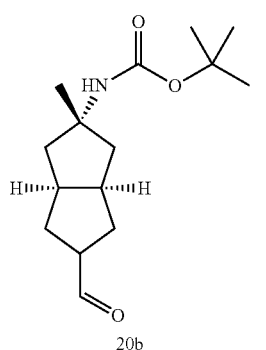

20b

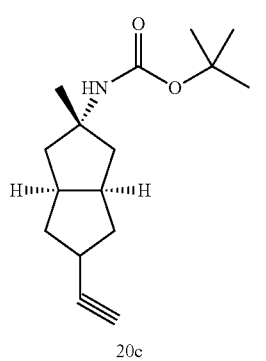

20c

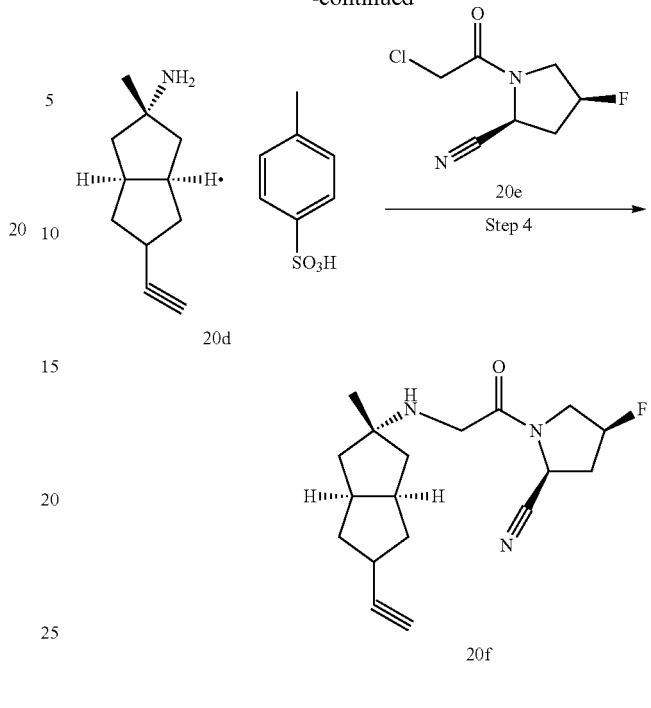

Step 1) tert-butyl ((2s,3aR,6aS)-5-formyl-2-methyloctahydropentalen-2-yl)carbamate To a solution of tert-butyl ((2s,3aR,6aS)-5-cyano-2-methyloctahydropentalen-2-yl) carbamate 20a (1.0 g, 3.79 mmol) in dichloromethane (40 mL) was added diisobutylaluminium hydride (5.7 mL, 1 M in hexane) at −78° C. over a period of 30 min. The mixture was stirred at −78° C. for 3 hours and quenched with saturated aqueous ammonium chloride (50 mL). The mixture was stirred vigorously for 40 min and ethyl acetate (20 mL) was added. The aqueous layer was extracted with ethyl acetate (20 mL×3). The combined organic layers were washed with saturated aqueous sodium chloride (80 mL), dried over anhydrous magnesium sulfate and concentrated in vacuo. The residue was purified by silica gel column chromatography (petroleum ether:ethyl acetate (V/V)=20:1) to give the title compound 20b as yellow oil (0.317 mg, 31.4%). The compound was characterized by the following spectroscopic data:

MS M/z (ESI): 212.2 (M-55); and $^1$H NMR (400 MHz, CD$_3$Cl) δ: 9.61 (dd, 1H), 4.36 (m, 1H), 2.84 (m, 1H), 2.69 (m, 2H), 2.32 (m, 2H), 2.03 (m, 2H), 1.79 (m, 2H), 1.58 (m, 2H), 1.43 (s, 9H), 1.40 (s, 3H).

Step 2) tert-butyl ((2s,3aR,6aS)-5-ethynyl-2-methyloctahydropentalen-2-yl)carbamate To a solution of tert-butyl ((2s,3aR,6aS)-5-formyl-2-methyloctahydropentalen-2-yl)carbamate 20b (0.285 g, 1.07 mmol) in methanol/dichloromethane (25 mL, V/V=4:1) were added potassium carbonate (0.188 g, 1.36 mmol) and (1-diazo-2-oxo-propyl)-phosphonic acid dimethyl ester (0.51 g, 2.67 mmol) in turn at rt. The mixture was further stirred for 8 hours and 10 mL of saturated aqueous sodium bicarbonate was added. The resulting mixture was extracted with ethyl acetate (15 mL×2). The combined organic layers were washed with saturated aqueous sodium chloride (10 mL), dried over anhydrous magnesium sulfate and concentrated in vacuo. The residue was purified by silica gel column chromatography (petroleum ether:ethyl acetate (V/V)=50:1) to give the title compound 20c as a white solid (0.244 g, 87.1%). The compound was characterized by the following spectroscopic data:

MS m/z (ESI): 208.2 (M-55); and $^1$H NMR (400 MHz, CDCl$_3$) δ: 4.31 (m, 1H), 2.60 (m, 4H), 2.28 (m, 2H), 2.14 (m, 1H), 2.01 (m, 2H), 1.66 (m, 2H), 1.43 (s, 9H), 1.38 (s, 3H).

Step 3) (2s,3aR,6aS)-5-ethynyl-2-methyloctahydro-pentalen-2-amine-4-methylbenzenesulfonate To a solution of tert-butyl ((2s,3aR,6aS)-5-ethynyl-2-methyloctahydropentalen-2-yl) carbamate 20c (0.244 g, 0.928 mmol) in dichloromethane (40 mL) was added p-toluenesulfonic acid monohydrate (0.264 g, 1.39 mmol) at rt. The mixture was stirred at rt for 5 hours and filtered. The filter cake was washed with cold ethyl acetate several times to give the title compound 20d as a white solid (0.208 g, 66.9%). The compound was characterized by the following spectroscopic data:

MS m/z (ESI): 164.3 (M+1); and $^1$H NMR (400 MHz, D$_2$O-d$_2$) δ: 7.59 (d, 2H), 7.27 (d, 2H), 2.61 (m, 2H), 2.36 (m, 1H), 2.31 (s, 3H), 2.09 (m, 1H), 1.98 (m, 2H), 1.62 (m, 4H), 1.41 (m, 2H), 1.33 (s, 3H).

Step 4) (2S,4S)-1-(2-(((2s,3aR,6aS)-5-ethynyl-2-methyloctahydropentalen-2-yl)amino) acetyl)-4-fluoropyrrolidine-2-carbonitrile To a solution of (2s,3aR,6aS)-5-ethynyl-2-methyloctahydropentalen-2-amine 4-methylbenzenesulfonate 20d (0.208g, 0.621 mmol) in N,N-dimethylformamide (20 mL) were added (2S,4S)-1-(2-chloroacetyl)-4-fluoropyrrolidine-2-carbonitrile 20e (0.118 g, 0.621 mmol), potassium iodide (10 mg, 0.0621 mmol) and potassium carbonate (0.257 g, 1.86 mmol). The mixture was stirred at rt for 1 day and concentrated in vacuo. The residue was dissolved in dichloromethane (20 mL). The solution was washed with saturated aqueous sodium chloride (20 mL) and concentrated in vacuo. The residue was purified by silica gel column chromatography (dichloromethane:methanol (V/V)=40:1) to give the title compound 20 as a white solid (0.124 g, 62.0%, HPLC: 97.0%). The compound was characterized by the following spectroscopic data:

MS m/z (ESI): 318.2 (M+1); and $^1$H NMR (400 MHz, CDCl$_3$) δ: 5.36 (m, 1H), 4.95 (m, 1H), 4.00-3.52 (m, 4H), 3.23 (m, 2H), 2.75 (m, 1H), 2.64 (m, 4H), 2.16 (m, 2H), 2.06 (m, 1H), 1.71 (m, 2H), 1.43 (m, 2H), 1.25 (s, 3H).

BIOLOGICAL ASSAYS

Active Inhibition DPP IV, DPP-8 and DPP-9 Assays

Tests and Operations:

The following methods were used for testing the inhibitive action of the compound disclosed herein against DPP-IV, DPP-8 and DPP-9 enzymatic activity. The inhibitive ability of the compound disclosed herein against enzymatic activity of DPP-IV, DPP-8 and DPP-9 was tested. The measurements of the inhibition ratio or the 50% inhibiting concentration $IC_{50}$ of every compound were based on a fixed quantity of enzyme-substrate mixtures and different concentrations of the test compounds.

Materials and Methods:

Materials:

DPP-IV enzyme was purchased from R&D, Catalog No. 1180-SE.

DPP-8 enzyme was purchased from Biomol, Catalog No. SE-827.

DPP-9 enzyme was purchased from Bioscience, Catalog No. 80090.

Methods:

The test compound was dissolved in an appropriate amount of DMSO to prepare 100 mM mother liquor, which was divided into EP tubes and preserved at −20° C. The mother liquor was diluted with an assay buffer to prepare solutions with required concentrations. Sample solutions with different concentrations (4 μL) and certain concentration of DPP-IV (DPP-8 or DPP-9) solution (4 μL) were added into 384-well plates in turn. Referred to the instruction manual, Gly-Pro-AMC was selected as a substrate and the concentration thereof was 10 μM. The 16 mM mother liquor was prepared from the substrate and preserved at −20° C. for use. The 16 mM mother liquor was diluted with an assay buffer to a solution of known concentration. The assay buffer of DPP-IV was 25 mM Tris, and its pH was 8.0. The assay buffers of DPP-8 and DPP-9 were 50 mM Tris, and their pH was 7.5. The substrate mother liquor was diluted with an assay buffer, and the mixture (4 μL) was added into 384-well plates to prepare final solution concentration. The whole process was carried out in an ice bath. After the addition of the components of the assay system was completed, the system was centrifuged. The supernatant was then transferred to an Infinite F200 multifunctional microplate reader, and 20 fluorescence values were recorded every 30 sec. And then Slope (V$_0$) was calculated directly by the software of microplate reader, fetching the data in the linear range. The measured reaction rate and the corresponding inhibition concentration were analyzed. Percent inhibition is I(%)=(V$_0$−V$_i$)/V$_0$×100%. V$_i$ represents the initial reaction rate at different inhibition concentrations. V$_0$ represents the initial reaction rate without inhibitor. V$_i$/V$_0$ represents the inhibition level of inhibitor. Relevant curve chart was made with inhibition concentration as a horizontal coordinate and the value of V$_i$/V$_0$ as a vertical coordinate. The IC$_{50}$ values were calculated by Graph Pad Prism statistical analysis software.

The IC$_{50}$ values of the test compounds against DPP-IV, DPP-8 and DPP-9 were shown in table 1.

TABLE 1

The IC$_{50}$ values of examples

| Example | IC$_{50}$(DPP-IV)/nM | IC$_{50}$(DPP-8)/nM | IC$_{50}$(DPP-9)/nM |
|---|---|---|---|
| 1 | 11.3 | 50530 | 4600 |
| 2 | 4.03 | 1580 | 54 |
| 3 | 2.49 | 3920 | 93 |
| 4 | 2.50 | 900 | 12.4 |
| 5 | 27.43 | — | 4333 |
| 6 | 4.52 | 18250 | 193 |
| 7 | 4.29 | 2669 | 27 |
| 8 | 6.91 | 3800 | 31 |
| 9 | 4.01 | 2850 | 29 |
| 10 | 2.43 | 5980 | 62 |
| 11 | 105.4 | 14240 | 916 |
| 12 | 171.3 | — | — |
| 13 | 9.25 | — | — |
| 14 | 9.23 | — | — |
| 15 | 1.56 | 1260 | 20 |
| 16 | 1.37 | 12850 | 340 |
| 17 | 2.72 | 3700 | 48 |

TABLE 1-continued

The IC$_{50}$ values of examples

| Example | IC$_{50}$(DPP-IV)/nM | IC$_{50}$(DPP-8)/nM | IC$_{50}$(DPP-9)/nM |
|---|---|---|---|
| 18 | 2.53 | 20150 | 242 |
| 19 | 25.8 | — | — |
| 20 | 4.18 | 2073 | 91 |

Conclusions: The compounds of the present invention have significant inhibitory effects on DPP-IV, and different selectivities on DPP-8 and DPP-9.

The Effects of DPP-IV Inhibitors on the Blood Glucose of Normal C57BL/6 Mice The effects of the test compounds on the oral glucose tolerance of normal C57BL/6 mice were observed, and the hypoglycemic activities of these compounds in vivo were evaluated preliminarily.
Experimental Animals:
  Mouse strain C57BL was used.
  Source was from Hunan si lai ke jing da laboratory animal Co., Ltd with certification number SCXK(xiang)2009-0004.
  Weight was 18~22 g.
  Male mice were used.
  Number of animals used was 35.
  Feeding Conditions: The mice were feeded under SPF condition. The room temperature was from 22 to 24° C. The illuminance was from 150 to 300 Lx, and the light cycle was 12 hours of light and 12 hours of dark.
Test Drugs:
  Preparation procedure: Drugs were accurately weighed, and 5 mg of compounds of examples 3, 9 15, 16 and 17 were dissolved respectively in 20 mL of normal saline to obtain 0.25 mg/mL solutions.
  Administrated Dose: The oral dose was 5 mg/kg and the gavage dose was 0.02 mL/g.
  Test Method: The normal male C57BL/6 mice were grouped randomly into a blank control group, a positive control group, and treatment groups having 7 mice each group.
  Administration and Serum Glucose Determination: C57BL/6 mice of each group were fasted for 18 hours before the experiment. The blood was drawn from the caudal vein of the mice and the glucose level was measured by using a blood-glucose meter. After detection, 0.25 mg/mL of positive control, 0.25 mg/mL of examples 3, 9, 15, 16 and 17 and normal saline were respectively administered to the positive control group, treatment groups and blank control group by intragastric administration. The blood glucose level (0 min) of positive control group was measured in 60 min after administration. The blood glucose levels (0 min) of the other groups were measured in 30 min after administration, and then glucose (2.5 g/kg) was administered to the mice through gavage. The blood was drawn from the caudal vein of the mice in 15 min, 30 min, 45 min, 60 min, 120 min after administration. The blood glucose levels of C57BL/6 mice were measured continuously by blood-glucose meter.
Data Processing and Statistical Analysis:
  1. Glucose concentration-time curve was plotted, and AUC from 0 to 120 min and hypoglycemic rate of each dosage group at blood glucose peak were calculated.
  2. Experimental data were represented in x̄±SD. The data were analyzed by SPSS 16.0 software. The data were compared between multiple groups using nonparametric Kruskal-Wallis H test method.

TABLE 2

The results of experiments of examples 3, 9, 15, 16 and 17

| Example | Nor-sugar rate % (5 mg/kg) |
|---|---|
| 3 | 35.96 |
| 9 | 18.7 |
| 15 | 24.72 |
| 16 | 24.69 |
| 17 | 30.4 |

Conclusions: The test compounds of examples 3, 9, 15, 16 and 17 have good hypoglycemic activities for C57BL/6 mice.

The above description of the embodiment is used to aid in understanding the invention and the core idea. It should be noted that a number of modifications and variations can be made in the present invention without departing from the inventive principle of the invention for those skilled in the art. These modifications and variations should be regarded as the scope of the present invention.

What is claimed is:
1. A compound having formula (I), or a stereoisomer, a geometric isomer, a tautomer, a racemate, an N-oxide, a hydrate, a solvate, or a pharmaceutically acceptable salt thereof,

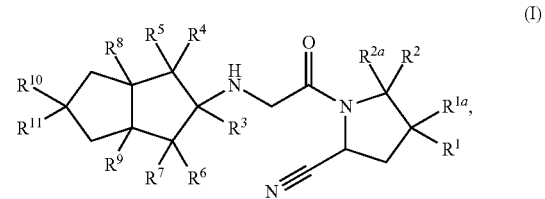

(I)

wherein each of R$^1$ and R$^{1a}$ is independently H, F, Cl or C$_{1-4}$ alkyl;
each of R$^2$ and R$^{2a}$ is independently H or C$_{1-4}$ alkyl; when each of R$^2$ and R$^{2a}$ is H, each of R$^1$ and R$^{1a}$ is independently H or F, or
R$^2$ and R$^{1a}$, together with the carbon atoms to which they are attached, form a 3-6 membered ring; each of R$^1$ and R$^{2a}$ is H, wherein the 3-6 membered ring optionally contains one or more heteroatoms independently selected from N, O and S, and wherein the 3-6 membered ring is optionally substituted with one or more substituents independently selected from H, C$_{1-4}$ alkyl, aryl, heteroaryl, haloalkyl, haloalkoxy, hydroxy, amino, alkyamino, R$^{14}$C(=O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, F, Cl, Br and I, or
R$^1$ and R$^{1a}$, together with the carbon atom to which they are attached, form a 3-6 membered ring, and R$^2$ and R$^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from C$_{1-4}$ alkyl, aryl, heteroaryl, haloalkyl, haloalkoxy, hydroxy, amino, alkylamino, R$^{14}$C(=O) NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$alkyl, F, Cl, Br and I;
wherein R$^3$ is C$_{1-4}$ alkyl;
each of R$^4$, R$^5$, R$^6$ and R$^7$ is independently H, hydroxy, C$_{1-4}$ alkyl, cycloalkyl or heterocyclyl, and wherein optionally each of the C$_{1-4}$ alkyl, cycloalkyl and heterocyclyl is substituted with one or more substituents independently selected from H, C$_{1-4}$ alkyl, F, Cl, Br, I, aryl, hydroxy, nitro, cyano, amino, C$_{1-3}$ alkylamino, R$^{14}$C(=O)NH—, alkoxy, aryloxy, heterocyclyl, carboxy and —C(=O)O—C$_{1-4}$ alkyl;
wherein each of R$^8$ and R$^9$ is independently H or methyl;
wherein each of R$^{10}$ and R$^{11}$ is independently H, hydroxy, C$_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_r$O—heteroaryl, alkenyl, alkynyl, cyano, —OR$^{14}$, —(CH$_2$)$_p$C(=O)OR$^{14}$, —(CH$_2$)$_p$OC(=O)R$^{14}$, —(CH$_2$)$_p$C(=O)NR$^{14}$R$^{15}$, —(CH$_2$)$_p$OC(=O)NR$^{14}$R$^{15}$, —C(=O)R$^{14}$, —N(R$^{14}$)C(=O)R$^{15}$, —N(R$^{15}$)C(=O)OR$^{15}$, —OC(=O)OR$^{14}$, —OC(=O)NR$^{14}$R$^{15}$ or —NR$^{14}$R$^{15}$, and wherein each of the C$_{1-6}$ alkyl, cycloalkyl, heterocyclyl, aryl, heteroaryl, —(CH$_2$)$_r$-aryl, —(CH$_2$)$_r$O-aryl, —(CH$_2$)$_r$-heteroaryl, —(CH$_2$)$_r$O-heteroaryl, alkenyl and alkynyl is optionally substituted with one or more substituents independently selected from H, C$_{1-6}$ alkyl, aryl, heteroaryl, haloalkyl, haloalkoxy, hydroxy, amino, alkylamino, R$^{14}$C(=O)NH—, R$^{14}$R$^{15}$NC(=O)—, cyano, alkoxy, aryloxy, aminoalkyl, hydroxyalkyl, heterocyclyl, carboxy, —C(=O)O—C$_{1-4}$ alkyl, halogen and —NR$^{12}$R$^{13}$, or
R$^{10}$ and R$^{11}$, together with the carbon atom to which they are attached, form a 3-8 membered ring, wherein the 3-8 membered ring optionally contains one or more heteroatoms independently selected from N, O and S, and wherein the 3-8 membered ring is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, R$^{14}$C(=O)NH—, R$^{14}$R$^{15}$NC(=O)—, cyano, aminoalkyl, hydroxyalkyl, heterocyclyl, trifluoromethyl, carboxy, —C(=O)O—C$_{1-4}$ alkyl and —NR$^{12}$R$^{13}$;
wherein each R$^{12}$, R$^{13}$, R$^{14}$ and R$^{15}$ is independently H, C$_{1-6}$ alkyl, —(CH$_2$)$_p$—C$_{3-6}$ cycloalkyl, aryl, heteroaryl or heterocyclyl, and wherein each of the C$_{1-6}$ alkyl, —(CH$_2$)$_p$—C$_{3-6}$ cycloalkyl, aryl, heteroaryl and heterocyclyl is optionally substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, heterocycloalkoxy, trifluoromethyl, carboxy, —C(=O)O—C$_{1-4}$ alkyl and —NR$^{12'}$R$^{13'}$, or
R$^{12}$ and R$^{13}$, together with the nitrogen atom to which they are attached, form a 3-8 membered heterocyclic ring; R$^{14}$ and R$^{15}$, together with the nitrogen atom to which they are attached, form a 3-8 membered heterocyclic ring, wherein each of the 3-8 membered heterocyclic rings optionally and independently contains one or more heteroatoms independently selected from N, O and S, and wherein each of the 3-8 membered heterocyclic rings is optionally and independently substituted with one or more substituents independently selected from H, C$_{1-4}$ alkyl, cycloalkyl, aryl, heteroaryl, alkoxy, cycloalkoxy, aryloxy, heteroaryloxy, halogen, hydroxy, amino, alkylamino, cyano, aminoalkyl, hydroxyalkyl, heterocyclyl, trifluoromethyl, carboxy and —C(=O)O—C$_{1-4}$ alkyl;
wherein each of R$^{12'}$ and R$^{13'}$ is independently H, C$_{1-4}$ alkyl, cycloalkyl, heterocyclyl, aryl or heteroaryl;
wherein r is 1, 2, 3 or 4; and
wherein p is 0, 1, 2, 3 or 4.

2. The compound of claim 1 having formula (IA) or a stereoisomer, a geometric isomer, a tautomer, a racemate, an N-oxide, a hydrate, a solvate, or a pharmaceutically acceptable salt thereof, (IA)

wherein each of R$^1$ and R$^{1a}$ independently H, F, Cl or C$_{1-4}$ alkyl;
each of R$^2$ and R$^{2a}$ is independently H or C$_{1-4}$ alkyl; when each of R$^2$ and R$^{2a}$ is H, each of R$^1$ and R$^{1a}$ is independently H or F, or
R$^2$ and R$^{1a}$, together with the carbon atoms to which they are attached, form a 3-6 membered ring; each of R$^1$ and R$^{2a}$ is H, wherein the 3-6 membered ring optionally contains one or more heteroatoms independently selected from N, O and S, and wherein the 3-6 membered ring is optionally substituted with one or more substituents independently selected from H, C$_{1-4}$ alkyl, C$_{6-10}$ aryl, C$_{1-9}$ heteroaryl, C$_{1-3}$ haloalkyl, C$_{1-3}$ haloalkoxy, hydroxy, amino, C$_{1-3}$ alkyamino, R$^{14}$C(=O)NH—, R$^{14}$R$^{15}$NC(=O)—, cyano, C$_{1-3}$ alkoxy, C$_{6-10}$ aryloxy, C$_{1-3}$ aminoalkyl, C$_{1-3}$ hydroxyalkyl, C$_{2-5}$ heterocyclyl, carboxy, —C(=O)O—C$_{1-4}$ alkyl, F, Cl, Br and I, or
R$^1$ and R$^{1a}$, together with the carbon atom to which they are attached, form a 3-6 membered ring, and R$^2$ and R$^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from H, C$_{1-4}$ alkyl, C$_{6-10}$ aryl, C$_{1-9}$ heteroaryl, C$_{1-3}$ haloalkyl, C$_{1-3}$ haloalkoxy, hydroxy, amino, C$_{1-3}$ alkylamino, R$^{14}$C(=O)NH—, R$^{14}$R$^{15}$NC(=O)—, cyano, C$_{1-3}$ alkoxy, C$_{6-10}$ aryloxy, C$_{1-3}$ aminoalkyl, C$_{1-3}$ hydroxyalkyl, C$_{2-5}$ heterocyclyl, carboxy, —C(=O)O—C$_{1-4}$ alkyl, F, Cl, Br and I;
wherein R$^3$ is C$_{1-4}$ alkyl;
each of R$^4$ and R$^5$ is independently H, hydroxy, C$_{1-4}$ alkyl, C$_{3-6}$ cycloalkyl or C$_{2-5}$ heterocyclyl, and wherein each of the C$_{1-4}$ alkyl, C$_{3-6}$ cycloalkyl and C$_{2-5}$ heterocyclyl is optionally substituted with one or more substituents independently selected from H, C$_{1-4}$ alkyl, F, Cl, Br, I, C$_{6-10}$ aryl, hydroxy, nitro, cyano, amino, C$_{1-3}$ alkylamino, R$^{14}$C(=O)NH—, C$_{1-3}$ alkoxy, C$_{6-10}$ aryloxy, C$_{2-5}$ heterocyclyl, carboxy and —C(=O)O—C$_{1-4}$ alkyl;
wherein each of R$^{10}$ and R$^{11}$ is independently H, hydroxy, C$_{1-6}$ alkyl, C$_{3-6}$ cycloalkyl, C$_{2-5}$ heterocyclyl, C$_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkenyl, $C_{2-4}$ alkynyl, cyano, —$OR^{14}$, —$(CH_2)_pC(=O)OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$, —$OC(=O)NR^{14}R^{15}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —$C(=O)O$—$C_{1-4}$ alkyl, halogen and —$NR^{12}R^{13}$, or $R^{10}$ and $R^{11}$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy, —$C(=O)O$—$C_{1-4}$ alkyl and —$NR^{12}R^{13}$;

wherein each $R^{12}$, $R^{13}$, $R^-$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —$C(=O)O$—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —$C(=O)O$—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and wherein p is 0, 1, 2, 3 or 4.

3. The compound of claim 2, wherein each of $R^1$ and $R^{1a}$ is independently H, F, Cl or $C_{1-4}$ alkyl;

each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-5 membered carboatomic ring; each of $R^1$ and $R^{2a}$ is H, wherein the 3-5 membered carboatomic ring is optionally substituted with one or more substituents independently selected from H, $C_{1-4}$ alkyl, $C_{1-3}$ haloalkyl, hydroxy, amino, F, Cl, Br and I;

wherein $R^3$ is $C_{1-4}$ alkyl;

each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C(=O)NH—$, $C_{1-3}$ alkoxy, $C_{6-10}$ aryloxy, $C_{2-5}$ heterocyclyl, carboxy and —$C(=O)O$—$C_{1-4}$ alkyl;

wherein each of $R^{10}$ and $R^{11}$ is independently H, hydroxy, $C_{1-6}$ alkyl, $C_{3-6}$ cycloalkyl, $C_{2-5}$ heterocyclyl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkynyl, cyano, —$OR^{14}$, —$(CH_2)_pOC(=O)R^{14}$, —$(CH_2)_pC(=O)NR^{14}R^{15}$, —$(CH_2)_pOC(=O)NR^{14}R^{15}$, —$C(=O)R^{14}$, —$N(R^{14})C(=O)R^{15}$, —$N(R^{15})C(=O)OR^{15}$, —$OC(=O)OR^{14}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —$C(=O)O$—$C_{1-4}$ alkyl, halogen and —$NR^{12}R^{13}$, or $R^{10}$ and $R^{11}$, together with the carbon atom to which they are attached, form a 3-5 membered ring, wherein the 3-5 membered ring optionally contains one or more heteroatoms independently selected from N, O and S, and wherein the 3-5 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy and —$C(=O)O$—$C_{1-4}$ alkyl;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —$C(=O)O$—$C_{1-4}$ alkyl and —$NR^{12'}R^{13'}$, or R[12] and R[13], together with the nitrogen atom to which they are attached, form a 3-6 membered heterocyclic ring, and R[14] and R[15], together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of R[12′] and R[13′] is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4; and wherein p is 0, 1, 2, 3 or 4.

4. The compound of claim 2, wherein each of R[1] and R[1a] is independently H, F or $C_{1-4}$ alkyl;

each of R[2] and R[2a] is independently H or $C_{1-4}$ alkyl; when each of R[2] and R[2a] is H, each of R[1] and R[1a] is independently H or F, or R[2] and R[1a], together with the carbon atoms to which they are attached, form a 3 membered unsubstituted carboatomic ring; each of R[1] and R[2a] is H;

wherein R[3] is $C_{1-4}$ alkyl;

each of R[4] and R[5] is independently H, hydroxy or $C_{1-4}$ alkyl, and wherein the $C_{1-4}$ alkyl is optionally substituted with one or more substituents independently selected from H, $C_{1-4}$ alkyl, F, Cl, Br or I;

wherein each of R[10] and R[11] is independently H, hydroxy, $C_{1-6}$ alkyl, $C_{2-4}$ alkynyl, cyano, —OR[14], —(CH$_2$)$_p$OC(=O)R[14], —(CH$_2$)$_p$C(=O)NR[14]R[15], —(CH$_2$)$_p$OC(=O)NR[14]R[15] or —C(=O)R[14], and wherein each of the $C_{1-6}$ alkyl and $C_{2-4}$ alkynyl is optionally substituted with one or more substituents independently selected from H, $C_{1-6}$ alkyl, $C_{6-10}$ aryl, $C_{1-3}$ haloalkyl, hydroxy, amino, $C_{1-3}$ alkylamino, cyano, $C_{1-3}$ alkoxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br, I and —NR[12]R[13], or R[10] and R[11], together with the carbon atom to which they are attached, form a 3-4 membered ring, wherein the 3-4 membered ring optionally contains one or more heteroatoms independently selected from N, O and S, and wherein the 3-4 membered ring is optionally substituted with one or more substituents independently selected from H, $C_{1-4}$ alkyl, F, Cl, Br, I, hydroxy, amino, $C_{1-3}$ alkylamino, R[14]C(=O)NH—, R[14]R[15]NC(=O)—, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —NR[12]R[13];

wherein each R[12], R[13], R[14] and R[15] is independently H, $C_{1-4}$ alkyl or —(CH$_2$)$_p$—$C_{3-6}$ cycloalkyl, and wherein each of the $C_{1-4}$ alkyl and —(CH$_2$)$_p$—$C_{3-6}$ cycloalkyl is optionally substituted with one or more substituents independently selected from H, $C_{1-4}$ alkyl, $C_{3-6}$ cycloalkyl, F, Cl, Br, I, hydroxy, amino, $C_{1-3}$ alkylamino, cyano, $C_{1-3}$ aminoalkyl, $C_{1-3}$ hydroxyalkyl, trifluoromethyl, carboxy and —C(=O)O—$C_{1-4}$ alkyl;

wherein r is 1, 2, 3 or 4; and wherein p is 0, 1, 2, 3 or 4.

5. The compound of claim 1 having a pharmaceutically acceptable salt thereof, wherein the pharmaceutically acceptable salt is hydrochloride, sulfate, nitrate, phosphate, metaphosphate, mesilate, ethyl sulfonate, citrate, benzene sulfonate, p-toluene sulfonate, malate, tartrate, succinate, fumarate, acetate, glycollate, hydroxyethyl sulfonate, maleate, lactate, lactobionate, trifluoroacetate or a combination thereof.

6. The compound of claim 1 having one of the following structures:

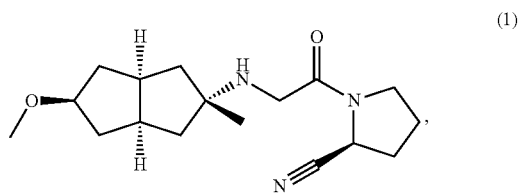

(1)

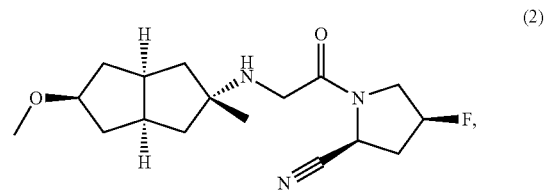

(2)

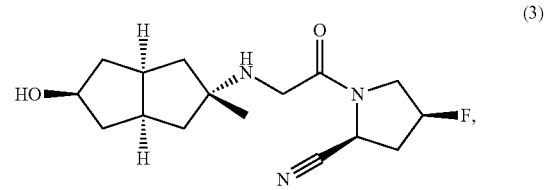

(3)

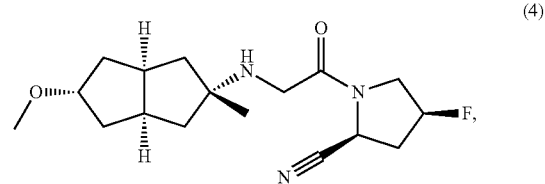

(4)

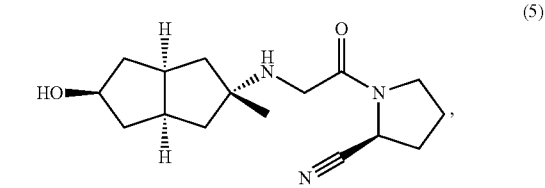

(5)

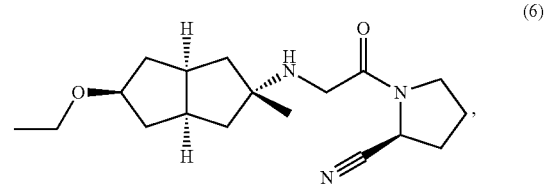

(6)

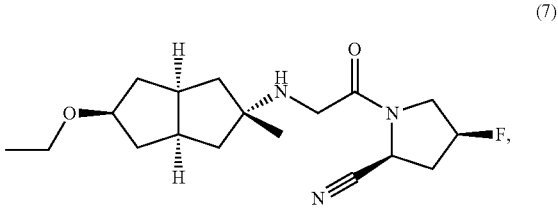

(7)

(8) 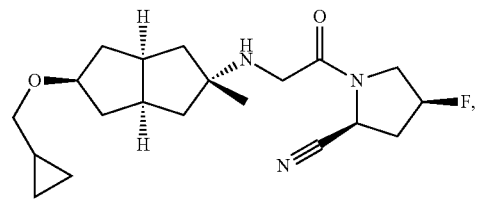

(9) 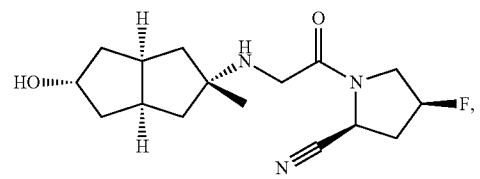

(10) 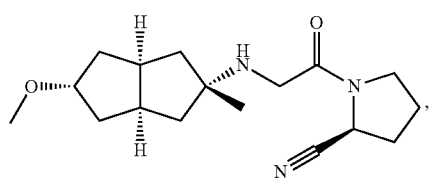

(12) 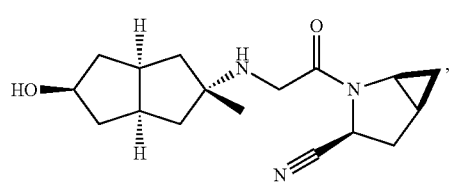

(13) 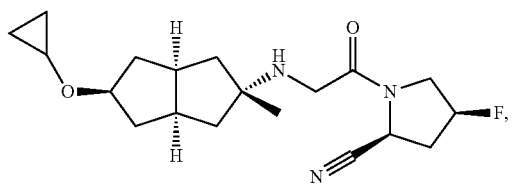

(14) 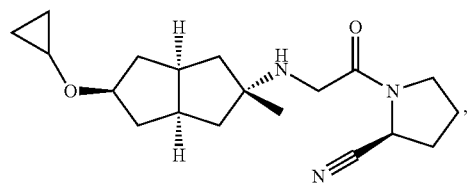

(15) 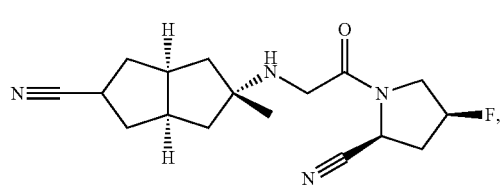

(16) 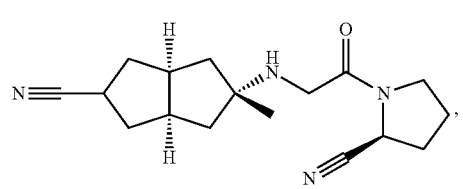

(17) 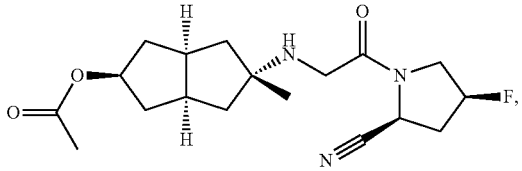

(18) 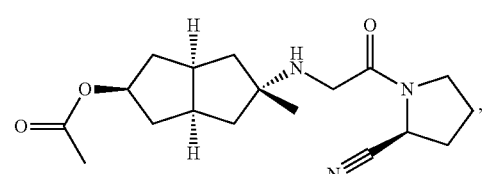

(19) 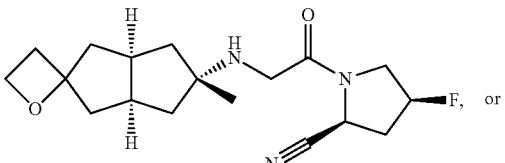

, or

(20) 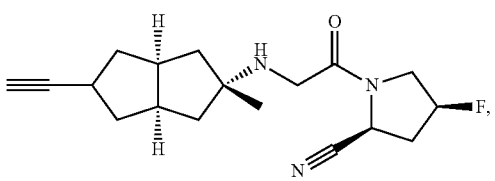

or a stereoisomer, a geometric isomer, a tautomer, a racemate, an N-oxide, a hydrate, a solvate, or a pharmaceutically acceptable salt thereof.

7. A pharmaceutical composition comprising a compound of claim 1, and a pharmaceutically acceptable carrier, excipient, diluent, adjuvant, vehicle or a combination thereof.

8. The pharmaceutical composition of claim 7 further comprising an additional therapeutic agent, wherein the additional therapeutic agent is an anti-diabetic agent other than a DPP-IV inhibitor, an antihyperglycemic agent, an antiadipositas drug, an antihypertensive agent, an antiplatelet agent, an antiatherosclerotic drug, a lipid-lowering agent, an anti-inflammatory or a combination thereof
wherein the anti-diabetic agent other than a DPP-IV inhibitor or an antihyperglycemic agent is a biguanide, a sulfonylurea, a glucosidase inhibitor, a PPAR agonist, an αP2 inhibitor, a PPARα/γ dual agonist, a SGLT-2 inhibitor, a nateglinide agent, insulin, a glucagon like peptide-1(GLP-1) inhibitor, a PTP1B inhibitor, a glycogen phosphorylase inhibitor, a glucose-6-phosphatase inhibitor or a combination thereof; and
wherein the lipid-lowering agent is an MTP inhibitor, an HMGCoA reductase inhibitor, a squalene synthase inhibitor, a fabric acid derivative, an ACAT inhibitor, a lipoxygenase inhibitor, a cholesterol absorption inhibitor, an ileal Na(+)/bile acid cotransporter inhibitor, an upregulator of LDL receptor activity, a bile acid sequestrant or a combination thereof; or wherein the lipid-lowering agent is pravastatin, simvastatin, atorvastatin, fluvastatin, cerivastatin, atavastatin, rosuvastatin or a combination thereof.

9. A process for preparing the compound of claim 2, comprising the step of reacting a compound of formula (1-1d) or a stereoisomer thereof with an N-haloacetyl-2- cyano-pyrrolidine derivative having formula (II) in the presence of a base in a polar solvent to give the compound of formula (IA);

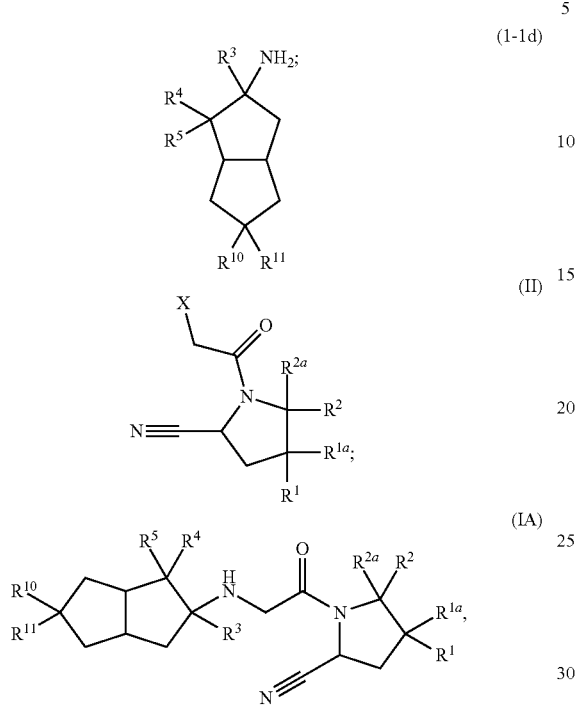

wherein each of $R^1$ and $R^{1a}$ is independently H, F, Cl or $C_{1-4}$ alkyl;

each of $R^2$ and $R^{2a}$ is independently H or $C_{1-4}$ alkyl; when each of $R^2$ and $R^{2a}$ is H, each of $R^1$ and $R^{1a}$ is independently H or F, or $R^2$ and $R^{1a}$, together with the carbon atoms to which they are attached, form a 3-6 membered ring; each of $R^1$ and $R^{2a}$ is H, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkyamino, $R^{14}C$ (=O)NH—, $R^{14}R^{15}NC$(=O)—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br and I, or $R^1$ and $R^{1a}$, together with the carbon atom to which they are attached, form a 3-6 membered ring, and $R^2$ and $R^{2a}$, together with the carbon atom to which they are attached, form a 3-6 membered ring, wherein each of the 3-6 membered rings optionally and independently contains one or more heteroatoms independently selected from N, O and S, and wherein each of the 3-6 membered rings is optionally and independently substituted with one or more substituents independently selected from H, $C_{1-4}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C$(=O)NH—, $R^{14}R^{15}NC$(=O)—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, F, Cl, Br and I;

wherein X is halogen;

wherein $R^3$ is $C_{1-4}$ alkyl;

each of $R^4$ and $R^5$ is independently H, hydroxy, $C_{1-4}$ alkyl, $C_{3-6}$ cycloalkyl or $C_{2-5}$ heterocyclyl and wherein each of the $C_{1-4}$ alkyl, $C_{3-6}$ cycloalkyl and $C_{2-5}$ heterocyclyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}C$(=O)NH—, $C_{1-3}$ alkoxy, $C_{6-10}$ aryloxy, $C_{2-5}$ heterocyclyl, carboxy and —C(=O)O—$C_{1-4}$ alkyl;

wherein each of $R^{10}$ and $R^{11}$ is independently H, hydroxy, $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkenyl, $C_{2-4}$ alkynyl, cyano, —$OR^{14}$, —$(CH_2)_pC$(=O)$OR^{14}$, —$(CH_2)_pOC$(=O)$R^{14}$, —$(CH_2)_pC$(=O)$NR^{14}R^{15}$, —$(CH_2)_pOC$(=O)$NR^{14}R^{15}$, —C(=O)$R^{14}$, —N($R^{14}$)C(=O)$R^{15}$, —N($R^{15}$)C(=O)$OR^{15}$, —OC(=O)$OR^{14}$, —OC(=O)$NR^{14}R^{15}$ or —$NR^{14}R^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —$(CH_2)_r$—$C_{6-10}$ aryl, —$(CH_2)_r$O—$C_{6-10}$ aryl, —$(CH_2)_r$—$C_{1-9}$ heteroaryl, —$(CH_2)_r$O—$C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C$(=O)NH—, $R^{14}R^{15}NC$(=O)—, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, —C(=O)O—$C_{1-4}$ alkyl, halogen and —$NR^{12}R^{13}$, or $R^{10}$ and $R^{11}$, together with the carbon atom to which they are attached, form a 3-6 membered ring, wherein the 3-6 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C$(=O)NH—, $R^{14}R^{15}NC$(=O)—, cyano, $C_{1-3}$ aminoalkyl, $C_{1-3}$ hydroxyalkyl, $C_{2-5}$ heterocyclyl, trifluoromethyl, carboxy, —C(=O)O—$C_{1-4}$ alkyl and —$NR^{12}R^{13}$;

wherein each $R^{12}$, $R^{13}$, $R^{14}$ and $R^{15}$ is independently H, $C_{1-6}$ alkyl, —$(CH_2)_p$—$C_{3-6}$ cycloalkyl, $C_{6-10}$ aryl, $C_{1-9}$ heteroaryl or $C_{2-5}$ heterocyclyl, and wherein each of the $C_{1-6}$ alkyl, —$(CH_2)_p$—$C_{3-6}$ cycloalkyl, $C_{6-10}$ aryl, $C_{1-9}$ heteroaryl and $C_{2-5}$ heterocyclyl is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, —C(=O)O—$C_{1-4}$ alkyl and —$NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and —C(=O)O—$C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4;

wherein p is 0, 1, 2, 3 or 4;

wherein the N-haloacetyl-2-cyano-pyrrolidine derivative is N-(2-chloroacetyl)pyrrolidine-2-carbonitrile, N-(2-bromoacetyl)pyrrolidine-2-carbonitrile, N-(2-chloroacetyl)-4-fluoropyrrolidine-2-carbonitrile, N-(2-bromoacetyl)-4-fluoropyrrolidine-2-carbonitrile, N-(2-chloroacetyl)-2-azabicyclo[3.1.0]hexane-3-carbonitrile, N-(2-bromoacetyl)-2-azabicyclo[3.1.0]hexane-3-carbonitrile;

wherein the polar solvent is water, formamide, dimethyl sulfoxide, acetonitrile, N,N-dimmethylformamide, methanol, ethanol, i-propanol or a combination thereof;

wherein the base is sodium hydride, potassium hydride, tert-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof; and wherein the process further comprises reacting the compound of formula (IA) with an acid to give an addition salt thereof, and wherein the addition salt is a hydrochloride, a sulfate, a nitrate, a phosphate, a metaphosphate, a mesilate, a ethyl sulfonate, a citrate, a benzene sulfonate, a p-toluene sulfonate, a malate, a tartrate, a succinate, a fumarate, a acetate, a glycollate, a hydroxyethyl sulfonate, a maleate, a lactate, a lactobionate or a trifluoroacetate.

10. The process of claim 9, wherein the compound of formula (1-1d) is prepared by the following steps:

(a) reacting a compound of formula (1-1a) with a Grignard reagent having formula $R^3$-MgX to give a compound of formula (1-1b):

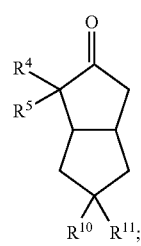

(1-1a)

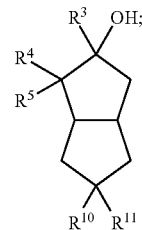

(1-1b)

(b) azidating the compound of formula (1-1b) with sodium azide in a halohydrocarbon solvent in the presence of an acid to obtain a compound of formula (1-1c):

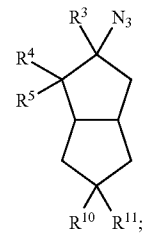

(1-1c)

and (c) reducing the compound of formula (1-1c) or a stereoisomer thereof in a reducing system in a solvent to obtain the compound of formula (1-1d):

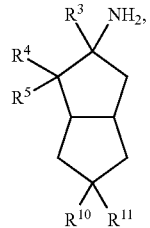

(1-1d)

wherein $R^3$ is $C_{1-4}$ alkyl; each of $R^4$ and $R^5$ is independently H, hydroxy or $C_{1-4}$ alkyl, and wherein the $C_{1-4}$ alkyl is optionally substituted with one or more substituents independently selected from H, $C_{1-4}$ alkyl, F, Cl, Br, I, $C_{6-10}$ aryl, hydroxy, nitro, cyano, amino, $C_{1-3}$ alkylamino, $R^{14}$C(=O)NH—, $C_{1-3}$ alkoxy, $C_{6-10}$ aryloxy, $C_{2-5}$ heterocyclyl, carboxy and —C(=O)O—$C_{1-4}$ alkyl;

wherein each of $R^{10}$ and $R^{11}$ is independently H, hydroxy, $C_{1-6}$ alkyl, $C_{3-6}$ cycloalkyl, $C_{2-5}$ heterocyclyl, —(CH$_2$)$_r$—$C_{6-10}$ aryl, —(CH$_2$)$_r$O—$C_{6-10}$ aryl, —(CH$_2$)$_r$—$C_{1-9}$ heteroaryl, —(CH$_2$)$_r$O—$C_{1-9}$ heteroaryl, $C_{2-4}$ alkenyl, $C_{2-4}$ alkynyl, cyano, —OR$^{14}$, —(CH$_2$)$_p$OC(=O)R$^{14}$, —(CH$_2$)$_p$C(=O)NR$^{14}$R$^{15}$, —(CH$_2$)$_p$OC(=O)NR$^{14}$R$^{15}$, —C(=O)R$^{14}$, —N(R$^{14}$)C(=O)OR$^{15}$, —N(R$^{15}$)C(=O)OR$^{15}$, —OC(=O)OR$^{14}$ or —NR$^{14}$R$^{15}$, and wherein each of the $C_{1-6}$ alkyl, $C_{3-6}$ cycloalkyl, $C_{2-5}$ heterocyclyl, $C_{6-10}$ aryl, $C_{1-9}$ heteroaryl, —(CH$_2$)$_r$—$C_{6-10}$ aryl, —(CH$_2$)$_r$O—$C_{6-10}$ aryl, —(CH$_2$)$_r$—$C_{1-9}$ heteroaryl, —(CH$_2$)$_r$O—$C_{1-9}$ heteroaryl, $C_{2-4}$ alkenyl and $C_{2-4}$ alkynyl is optionally substituted with one or more substituents independently selected from H, $C_{1-6}$ alkyl, $C_{6-10}$ aryl, $C_{1-9}$ heteroaryl, $C_{1-3}$ haloalkyl, $C_{1-3}$ haloalkoxy, hydroxy, amino, $C_{1-3}$ alkylamino, $R^{14}C(=O)NH—$, $R^{14}R^{15}NC(=O)—$, cyano, $C_{1-3}$ alkoxy, $C_{6-10}$ aryloxy, $C_{1-3}$ aminoalkyl, $C_{1-3}$ hydroxyalkyl, $C_{2-5}$ heterocyclyl, carboxy, $—C(=O)O—C_{1-4}$ alkyl, halogen and $—NR^{12}R^{13}$, or $R^{10}$ and $R^{11}$, together with the carbon atom to which they are attached, form a 3-6 membered ring, wherein the 3-5 membered ring optionally contains one or more heteroatoms independently selected from N, O and S, and wherein the 3-6 membered ring is optionally substituted with one or more substituents independently selected from H, $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, $R^{14}C(=O)NH—$, $R^{14}R^{15}NC(=O)—$, cyano, $C_{1-3}$ aminoalkyl, $C_{1-3}$ hydroxyalkyl, $C_{2-5}$ heterocyclyl, trifluoromethyl, carboxy, $—C(=O)O—C_{1-4}$ alkyl and $—NR^{12}R^{13}$;

wherein each $R^{12}R^{13}$, $R^{14}$ and $R^{15}$ is independently H, $C_{1-6}$ alkyl, $—(CH_2)_p—C_{3-6}$ cycloalkyl, $C_{6-10}$ aryl, $C_{1-9}$ heteroaryl or $C_{2-5}$ heterocyclyl, and wherein each of the $C_{1-6}$ alkyl, $—(CH_2)_p—C_{3-6}$ cycloalkyl, $C_{6-10}$ aryl, $C_{1-9}$ heteroaryl and $C_{2-5}$ heterocyclyl is optionally substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, $C_{2-5}$ heterocycloalkoxy, trifluoromethyl, carboxy, $—C(=O)O—C_{1-4}$ alkyl and $—NR^{12'}R^{13'}$, or $R^{12}$ and $R^{13}$, together with the nitrogen atom to which they are attached, form a 3-6 membered heterocyclic ring, and $R^{14}$ and $R^{15}$, together with the nitrogen atom to which they are attached, form a 3-6 membered heterocyclic ring, wherein each of the 3-6 membered heterocyclic rings optionally and independently contains one or more heteroatoms independently selected from N, O and S, and wherein each of the 3-6 membered heterocyclic rings is optionally and independently substituted with one or more substituents independently selected from $C_{1-4}$ alkyl, $C_{3-6}$ cycloalkyl, $C_{6-10}$ aryl, $C_{1-9}$ heteroaryl, $C_{1-3}$ alkoxy, $C_{3-6}$ cycloalkoxy, $C_{6-10}$ aryloxy, $C_{1-9}$ heteroaryloxy, halogen, hydroxy, amino, $C_{1-3}$ alkylamino, cyano, $C_{1-3}$ aminoalkyl, $C_{1-3}$ hydroxyalkyl, $C_{2-5}$ heterocyclyl, trifluoromethyl, carboxy and $—C(=O)O—C_{1-4}$ alkyl;

wherein each of $R^{12'}$ and $R^{13'}$ is independently H, $C_{1-4}$ alkyl, $C_{3-6}$ cycloalkyl, $C_{2-5}$ heterocyclyl, $C_{6-10}$ aryl or $C_{1-9}$ heteroaryl;

wherein r is 1, 2, 3 or 4;

wherein p is 0, 1, 2, 3 or 4;

wherein X is Cl, Br or I;

wherein the solvent is a nonpolar solvent, a weak polar solvent or a polar solvent;

wherein the halohydrocarbon solvent is methyl chloride, dichloromethane, trichloromethane, tetrachloromethane, tribromethane, trichloroethylene, tetrachloroethylene, 1,1,1,2-tetrachloroethane, 1,1,1-trichloroethane, 1,1,2,2-tetrachloroethane, 1,1,2-trichloroethane, 1,1-dichloro-l-fluoroethane, 1,2,3-trichloropropane or 1,2-dichloroethane;

wherein the reducing system is hydrogen with a platinum on activated carboncatalyst, a sodium borohydride-copper sulfate system, lithium aluminium hydride, sodium borohydride or a combination thereof;

wherein the polar solvent is water, formamide, dimethyl sulfoxide, acetonitrile, N,N-dimethylformamide, methanol, ethanol, isopropanol or a combination thereof; and wherein the acid is sulfuric acid, hydrochloric acid, nitric acid, phosphoric acid, formic acid, acetic acid, trifluoroacetic acid, methyl sulfonic acid, benzenesulfonic acid, p-toluene sulfonic acid, 4-nitro benzoic acid or a combination thereof;

wherein when $R^{10}$ or $R^{11}$ of formula (1-1c) is hydroxy, the process further comprises the steps of:

(a) condensing the compound of formula (1-1c) with an aromatic acid in the presence of triphenylphosphine and diethyl azodicarboxylate to give an ester; and (b) hydrolyzing the ester in the presence of a base in a polar solvent to give a stereoisomer of the compound of formula (1-1c);

wherein the base is sodium hydride, potassium hydride, tent-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the aromatic acid is benzoic acid, p-nitrobenzoic acid, 4-methoxybenzoic acid or 4-methylbenzoic acid; and wherein the polar solvent is water, formamide, dimethyl sulfoxide, acetonitrile, N,N-dimethylformamide, methanol, ethanol, isopropanol or a combination thereof.

11. The process of claim 9, wherein the compound of formula (1-1d) is prepared by the following steps:

(a) reacting a compound of formula (1-1e) with a Grignard reagent having formula $R^3—MgX$ to give a compound of formula (1-1f):

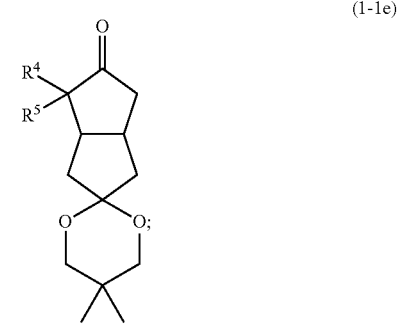
(1-1e)

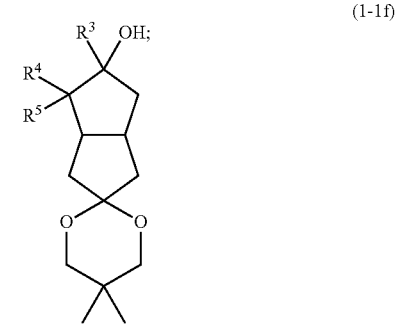
(1-1f)

(b) removing the protecting group of the compound of formula (1-1f) in the presence of an acid in a polar solvent to give a compound of formula (1-1g):

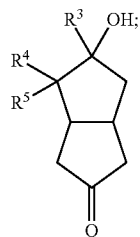

(1-1g)

(c) reducing the compound of formula (1-1g) in the presence of a reducing agent in a polar solvent to give a compound of formula (1-1h):

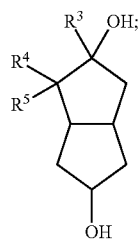

(1-1h)

(d) azidating the compound of formula (1-1h) with sodium azide in a halohydrocarbon solvent in the presence of an acid to obtain a compound of formula (1-1i):

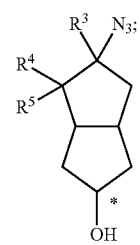

(1-1i)

and
(e) reducing the compound of formula (1-1i) or a stereoisomer thereof with a reducing system in a solvent to obtain the compound of formula (1-1d):

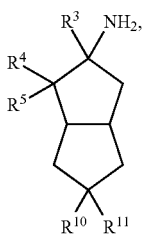

(1-1d)

wherein $R^3$ is $C_{1-4}$ alkyl;
each of $R^4$ and $R^5$ is independently H, hydroxy, $C_{1-4}$ alkyl, cycloalkyl or heterocyclyl, and wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)NH—$, alkoxy, aryloxy, heterocyclyl, carboxy and $—C(=O)O—C_{1-4}$ alkyl;
wherein each of $R^{10}$ and $R^{11}$ is independently H or hydroxyl;
wherein each $R^{14}$ and $R^{15}$ is independently H, $C_{1-6}$ alkyl, $—(CH_2)_p—C_{3-6}$ cycloalkyl, aryl, heteroaryl or heterocyclyl, and wherein each of the $C_{1-6}$ alkyl, $—(CH_2)_p—C_{3-6}$ cycloalkyl, aryl, heteroaryl and heterocyclyl is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH—$, $R^{14}R^{15}NC(=O)—$, cyano, aminoalkyl, hydroxyalkyl, heterocyclyl, heterocycloalkoxy, trifluoromethyl, carboxy, $—C(=O)O—C_{1-4}$ alkyl and $—NR^{12'}R^{13'}$;
wherein each of $R^{12'}$ and $R^{13'}$ is independently H, $C_{1-4}$ alkyl, cycloalkyl, heterocyclyl, aryl or heteroaryl;
wherein r is 1, 2, 3 or 4;
wherein p is 0, 1, 2, 3 or 4;
wherein X is Cl, Br or I;
wherein the halohydrocarbon solvent is methyl chloride, dichloromethane, trichloromethane, tetrachloromethane, tribromethane, trichloroethylene, tetrachloroethylene, 1,1,1,2-tetrachloroethane, 1,1,1-trichloroethane, 1,1,2,2-tetrachloroethane, 1,1,2-trichloroethane, 1,1-dichloro-1-fluoroethane, 1,2,3-trichloropropane or 1,2-dichloroethane;
wherein the reducing system is hydrogen with a platinum on activated carbon catalyst, a sodium borohydride-copper sulfate system, lithium aluminium hydride, sodium borohydride or a combination thereof;
wherein the reducing agent is hydrogen, sodium borohydride, lithium aluminium, tri-tert Butoxyaluminum hydride or a combination thereof;
wherein the polar solvent is water, formamide, dimethyl sulfoxide, acetonitrile, N,N-dimethylformamide, methanol, ethanol, isopropanol or a combination thereof; and
wherein the acid is sulfuric acid, hydrochloric acid, nitric acid, phosphoric acid, formic acid, acetic acid, trifluoroacetic acid, methyl sulfonic acid, benzenesulfonic acid, p-toluene sulfonic acid, 4-nitro benzoic acid or a combination thereof;
wherein the process further comprises the steps of:
(a) condensing the compound of formula (1-1i) with an aromatic acid in the presence of triphenylphosphine and diethyl azodicarboxylate to give an ester; and
(b) hydrolyzing the ester in the presence of a base in a polar solvent to give a stereoisomer of the compound of formula (1-1i);
wherein the base is sodium hydride, potassium hydride, tent-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the aromatic acid is benzoic acid, p-nitrobenzoic acid, 4-methoxybenzoic acid or 4-methylbenzoic acid;

wherein the polar solvent is water, formamide, dimethyl sulfoxide, acetonitrile, NN-dimethylformamide, methanol, ethanol, isopropanol or a combination thereof;

wherein the process further comprises the steps of:

(a) reacting the compound of fomula (1-1i) or a stereoisomer thereof with haloalkane, acyl halide or anhydride in the presence of a base to give a compound of formula (1-1C):

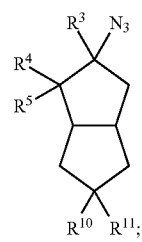

(1-1c)

and (b) reducing the compound of formula (1-1c) in a solvent to obtain the compound of formula (1-1d):

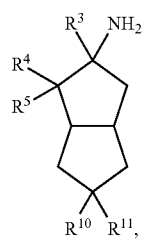

(1-1d)

wherein the solvent is a nonpolar solvent, a weak polar solvent or a polar solvent;

wherein the base is sodium hydride, potassium hydride, tent-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof;

wherein the acyl halide is acetylchloride, propionyl chloride, methylsulfonyl chloride or paratoluensulfonyl chloride; the haloalkane is fluoromethane, chloroethane, bromoethane, iodomethane, iodoethane, chlorocyclopropane or (bromomethyl)cyclopropane;

wherein the anhydride is acetic anhydride, propionic anhydride, acetic formic anhydride, acetic benzoic anhydride or maleic anhydride; and wherein the polar solvent is water, formamide, dimethyl sulfoxide, acetonitrile, N,N-dimethylformamide, methanol, ethanol, isopropanol or a combination thereof.

12. The process for preparing the compound of claim 9, wherein the compound of formula (1-1d) is prepared by the following steps:

(a) reducing a compound of formula (1-1i) to give a compound of formula (1-1q):

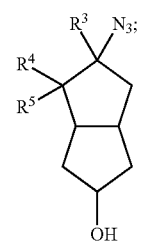

(1-1i)

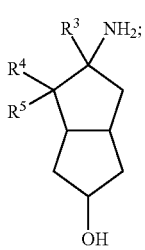

(1-1q)

(b) reacting the compound of formula (1-1q) with di-tent-butyl dicarbonate in the presence of a base to give a compound of formula (1-1r):

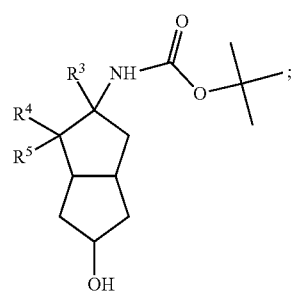

(1-1r)

(c) oxidizing the compound of formula (1-1r) with an oxidizing agent to give a compound of formula (1-1s):

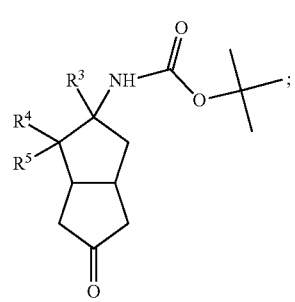

(1-1s)

(d) reacting the compound of formula (1-1s) with tosyl isocyanate in the presence of a base to give a compound of formula (1-1t):

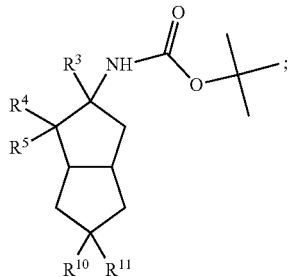

(1-1t)

and (e) reducing the compound of formula (Mt) with a reducing system in a polar solvent to give the compound of formula (1-1d):

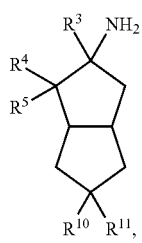

(1-1d)

wherein $R^3$ is $C_{1-4}$ alkyl; each of $R^4$ and $R^5$ is independently H, hydroxy, $C_{1-4}$ alkyl, cycloalkyl or heterocyclyl, wherein each of the $C_{1-4}$ alkyl, cycloalkyl and heterocyclyl is optionally substituted with one or more substituents independently selected from H, $C_{1-4}$ alkyl, F, Cl, Br, I, aryl, hydroxy, nitro, cyano, amino, $C_{1-3}$ alkylamino, $R^{14}C(=O)NH-$, alkoxy, aryloxy, heterocyclyl, carboxy and $-C(=O)O-C_{1-4}$ alkyl;

wherein each of $R^{10}$ and $R^{11}$ is independently H, hydroxy, -or cyano;

wherein each $R^{14}$ and $R^{15}$ is independently H, $C_{1-6}$ alkyl, $-(CH_2)_p-C_{3-6}$ cycloalkyl, aryl, heteroaryl or heterocyclyl, and wherein each of the $C_{1-6}$ alkyl, $-(CH_2)_p-C_{3-6}$ cycloalkyl, aryl, heteroaryl and heterocyclyl is optionally substituted with one or more substituents independently selected from H, $C_{1-4}$ alkyl, cycloalkyl, aryl, heteroaryl, alkoxy, cycloalkoxy, aryloxy, heteroaryloxy, halogen, hydroxy, amino, alkylamino, $R^{14}C(=O)NH-$, $R^{14}R^{15}NC(=O)-$, cyano, aminoalkyl, hydroxyalkyl, heterocyclyl, heterocycloalkoxy, trifluoromethyl, carboxy, $-C(=O)O-C_{1-4}$ alkyl and $-NR^{12'}R^{13'}$;

wherein each of $R^{12'}$ and $R^{13'}$ is independently H, $C_{1-4}$ alkyl, cycloalkyl, heterocyclyl, aryl or heteroaryl;

wherein r is 1, 2, 3 or 4;

wherein p is 0, 1, 2, 3 or 4;

wherein the reducing system is hydrogen with a platinum on activated carbon catalyst, a sodium borohydride-copper sulfate system, lithium aluminium hydride, sodium borohydride or a combination thereof;

wherein the polar solvent is water, formamide, dimethyl sulfoxide, acetonitrile, N,N-dimethylformamide, methanol, ethanol, isopropanol or a combination thereof;

wherein the base is sodium hydride, potassium hydride, tent-butyl lithium, lithium bis(trimethylsilyl)amide, sodium bis(trimethylsilyl)amide, sodium hydroxide, potassium hydroxide, potassium tert-butanolate, lithium hydride, lithium aluminium hydride, lithium tri-tert-butoxyaluminum hydride, potassium carbonate, sodium carbonate, pyridine, N-methyl-4-pyridinamine, triethylamine, morpholine or a combination thereof; and wherein the oxidizing agent is Dess-Martin periodinane, 2-iodoxybenzoic acid, oxalyl chloride, chromium trioxide-pyridine complex, sodium hypochlorite, pyridine sulfur trioxide, sodium periodate, hydrogen peroxide, 2,2,6,6-tetramethylpiperidinooxy, potassium permanganate or a combination thereof.

13. A method for inhibiting the activity of DPP-IV, comprising administering to the patient in need thereof a therapeutically effective amount of the compound of claim 1.

14. A method for treating a disease, lessening a disease symptoms, delaying the progression or onset of a disease or increasing HDL level, comprising administering to the patient in need thereof a therapeutically effective amount of the compound of claim 1, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis, hypertension, acute anemia or neutropenia.

15. A method for inhibiting the activity of DPP-IV, comprising administering to the patient in need thereof a therapeutically effective amount of the pharmaceutical composition of claim 7.

16. A method for treating a disease, lessening a disease symptoms, delaying the progression or onset of a disease or increasing HDL level, comprising administering to the patient in need thereof a therapeutically effective amount of the pharmaceutical composition of claim 7, wherein the disease is diabetes, diabetic retinopathy, diabetic neuropathy, diabetic nephropathy, insulin resistance, hyperglycemia, hyperinsulinemia, elevated blood levels of fatty acids or glycerol, hyperlipidemia, obesity, hypertriglyceridemia, syndrome X, a diabetic complication, atherosclerosis, hypertension, acute anemia or neutropenia.

* * * * *